United States Patent
Shields et al.

(10) Patent No.: US 11,472,758 B2
(45) Date of Patent: Oct. 18, 2022

(54) METHODS FOR OBTAINING COMPOUNDS FROM A PLANT OR FUNGUS MATERIAL, RESPECTIVE COMPOSITIONS, AND USES THEREOF

(71) Applicant: Real Isolates, LLC, Woburn, MA (US)

(72) Inventors: Christina Miyabe Shields, Boston, MA (US); Andrew Michiel Westerkamp, Charlestown, MA (US)

(73) Assignee: Real Isolates, LLC, Beverly, MA (US)

( * ) Notice: Subject to any disclaimer, the term of this patent is extended or adjusted under 35 U.S.C. 154(b) by 0 days.

(21) Appl. No.: 17/552,134

(22) Filed: Dec. 15, 2021

(65) Prior Publication Data

US 2022/0112147 A1    Apr. 14, 2022

Related U.S. Application Data

(63) Continuation of application No. PCT/US2021/012778, filed on Jan. 8, 2021.
(Continued)

(51) Int. Cl.
*C07C 37/68* (2006.01)
*B01D 53/04* (2006.01)
(Continued)

(52) U.S. Cl.
CPC .............. *C07C 37/685* (2013.01); *B01D 3/10* (2013.01); *B01D 11/0219* (2013.01);
(Continued)

(58) Field of Classification Search
CPC ....... C07C 37/685; C07C 37/82; C07C 27/34; B01D 3/10; B01D 11/0219;
(Continued)

(56) References Cited

U.S. PATENT DOCUMENTS 1,679,728 A    8/1928  Fe
4,136,206 A    1/1979  Kulesza et al.
(Continued)

FOREIGN PATENT DOCUMENTS

CA    3036154 A1    3/2018
CA    3115179 A1    6/2020
(Continued)

OTHER PUBLICATIONS

Anonymous, "Cannabinoid," Wikipedia (16 pages) (retrieved from URL https://en.wikipedia.org/wiki/Cannabinoid on Jul. 16, 2021).
(Continued)

*Primary Examiner* — Gabriel E Gitman
(74) *Attorney, Agent, or Firm* — Foley Hoag LLP

(57) ABSTRACT

Disclosed herein is a method for obtaining compounds and compositions from plant and fungus materials by thermal treatment, affinity capture, filtration, and release through multi-phasic transitions between gas, solid, and liquid states. The compounds of interest are obtained by manipulating the temperature and pressure of the heating chamber. The compounds in gas phase are passed through an affinity medium which captures the compounds of interest in either solid or liquid phase by exposing the compound of interest to the localized micro-affinity environment of the medium. The compounds are separated from the medium using direct competition with solvent or buffers optimized for the specific chemical properties of compounds.

30 Claims, 10 Drawing Sheets

Related U.S. Application Data

(60) Provisional application No. 62/959,632, filed on Jan. 10, 2020.

(51) Int. Cl.

| | | |
|---|---|---|
| B01D 3/10 | (2006.01) | |
| B01D 11/02 | (2006.01) | |
| B01D 15/12 | (2006.01) | |
| B01D 53/22 | (2006.01) | |
| C07C 37/82 | (2006.01) | |
| C07D 311/80 | (2006.01) | |
| B01D 46/00 | (2022.01) | |
| B01D 11/00 | (2006.01) | |
| B01J 20/10 | (2006.01) | |
| B01J 20/28 | (2006.01) | |
| B01J 20/283 | (2006.01) | |
| B01J 20/284 | (2006.01) | |
| B01J 20/285 | (2006.01) | |
| B01J 20/287 | (2006.01) | |

(52) U.S. Cl.
CPC .......... *B01D 11/0288* (2013.01); *B01D 15/12* (2013.01); *B01D 53/04* (2013.01); *B01D 53/228* (2013.01); *C07C 37/82* (2013.01); *C07D 311/80* (2013.01); *B01D 46/00* (2013.01); *B01D 2011/007* (2013.01); *B01D 2253/20* (2013.01); *B01D 2253/25* (2013.01); *B01D 2257/70* (2013.01); *B01D 2259/4533* (2013.01); *B01J 20/103* (2013.01); *B01J 20/283* (2013.01); *B01J 20/284* (2013.01); *B01J 20/285* (2013.01); *B01J 20/287* (2013.01); *B01J 20/28078* (2013.01)

(58) Field of Classification Search
CPC .. B01D 11/0288; B01D 15/12; B01D 15/325; B01D 53/04; B01D 53/228; B01D 2011/007; B01D 2253/20; B01D 2253/25; B01D 2257/70; B01D 2259/4533; B01D 2257/708; B01D 53/1487; B01J 20/282; C07D 311/80; C11B 1/10
See application file for complete search history.

(56) References Cited

U.S. PATENT DOCUMENTS

| | | | |
|---|---|---|---|
| 4,596,259 A | 6/1986 | White et al. | |
| 5,154,822 A * | 10/1992 | Simpson | B01J 20/103 |
| | | | 502/402 |
| 5,516,923 A | 5/1996 | Hebert et al. | |
| 5,535,746 A | 7/1996 | Hoover et al. | |
| 6,258,264 B1 | 7/2001 | Gjerde et al. | |
| 6,403,126 B1 | 6/2002 | Webster et al. | |
| 7,285,219 B2 | 10/2007 | Kolesinski et al. | |
| 7,291,250 B1 | 11/2007 | Popp et al. | |
| 7,622,140 B2 | 11/2009 | Whittle et al. | |
| 8,445,034 B1 | 5/2013 | Coles, Jr. | |
| 9,351,953 B2 | 5/2016 | Stodola | |
| 9,504,723 B2 | 11/2016 | Kolsky | |
| 9,669,326 B2 | 6/2017 | Todosiev et al. | |
| 9,669,328 B2 | 6/2017 | Jones | |
| 9,724,622 B2 | 8/2017 | Anwer | |
| 9,901,843 B2 | 2/2018 | Todosiev et al. | |
| 9,974,820 B2 | 5/2018 | Ablett | |
| 10,189,762 B1 | 1/2019 | Oroskar et al. | |
| 10,195,159 B2 | 2/2019 | Whittle et al. | |
| 10,272,360 B2 | 4/2019 | Lopa | |
| 10,376,657 B2 | 8/2019 | Jones | |
| 10,512,856 B1 | 12/2019 | Jackson et al. | |
| 10,517,320 B2 | 12/2019 | Leo | |
| 10,669,248 B2 | 6/2020 | Thomas et al. | |
| 10,799,812 B2 | 10/2020 | Gildrien | |
| 10,843,991 B2 | 11/2020 | Oroskar et al. | |
| 10,919,828 B1 | 2/2021 | Roa-Espinosa et al. | |
| 10,946,329 B2 * | 3/2021 | Kolesinski | B01D 3/40 |
| 11,078,145 B2 | 8/2021 | Oroskar et al. | |
| 2002/0045157 A1 * | 4/2002 | Hirai | B01D 15/00 |
| | | | 435/2 |
| 2003/0102260 A1 | 6/2003 | Gjerde et al. | |
| 2004/0147767 A1 | 7/2004 | Whittle et al. | |
| 2006/0153941 A1 | 7/2006 | Musty et al. | |
| 2011/0034712 A1 | 2/2011 | Lin | |
| 2014/0298511 A1 | 10/2014 | Lewis et al. | |
| 2015/0190780 A1 * | 7/2015 | Huang | B01D 15/08 |
| | | | 556/417 |
| 2015/0265720 A1 | 9/2015 | Levine et al. | |
| 2016/0106705 A1 | 4/2016 | Verzura et al. | |
| 2016/0228787 A1 | 8/2016 | Payack | |
| 2016/0303263 A1 * | 10/2016 | Engell | C07B 59/008 |
| 2016/0346339 A1 * | 12/2016 | Finley | B01D 11/0288 |
| 2017/0049830 A1 | 2/2017 | Raderman | |
| 2018/0116131 A1 * | 5/2018 | Leo | A01G 24/00 |
| 2018/0125777 A1 | 5/2018 | Lindsay | |
| 2018/0140965 A1 * | 5/2018 | Flora | C11B 1/10 |
| 2018/0178140 A1 * | 6/2018 | Todosiev | B01D 11/0292 |
| 2018/0344661 A1 * | 12/2018 | Finley | A61K 31/355 |
| 2019/0010106 A1 | 1/2019 | Oroskar et al. | |
| 2019/0069309 A1 | 2/2019 | Nilsson | |
| 2019/0189427 A1 * | 6/2019 | Thorum | H01L 21/02063 |
| 2019/0232190 A1 | 8/2019 | Rivas | |
| 2019/0255461 A1 | 8/2019 | Lopa | |
| 2019/0276420 A1 * | 9/2019 | Tegen | C07D 301/32 |
| 2019/0360903 A1 * | 11/2019 | Wilks | B01J 20/286 |
| 2019/0382327 A1 * | 12/2019 | McGrane | B01D 9/005 |
| 2020/0289599 A1 | 9/2020 | Meloul | |

FOREIGN PATENT DOCUMENTS

| | | |
|---|---|---|
| IL | 255268 A | 1/2019 |
| WO | WO-2002/089945 A2 | 11/2002 |
| WO | WO-2013/165251 A1 | 11/2013 |
| WO | WO-2016/064987 A1 | 4/2016 |
| WO | WO-2018/051346 A1 | 3/2018 |
| WO | WO-2019/010419 A1 | 1/2019 |
| WO | WO-2019/227199 A1 | 12/2019 |
| WO | WO-2020/033859 A1 | 2/2020 |
| WO | WO-2020/046822 A1 | 3/2020 |
| WO | WO-2020/106920 A1 | 5/2020 |
| WO | WO-2021/142322 A1 | 7/2021 |

OTHER PUBLICATIONS

Anonymous, "Medical cannabis research," Wikipedia (9 pages) (retrieved from URL https://en.wikipedia.org/wiki/Medical_cannabis on Jul. 16, 2021).

Carrara et al., "Development of a Vaping Machine for the Sampling of THC and CBD Aerosols Generated by Two Portable Dry Herb Cannabis Vaporisers," Medical Cannabis and Cannabinoids, 3: 84-93 (2020).

Gieringer et al., "Cannabis Vaporizer Combines Efficient Delivery of THC with Effective Suppression of Pyrolytic Compounds," Journal of Cannabis Therapeutics: 7-27 (2004).

Gieringer., "Cannabis "Vaporization" A Promising Strategy for Smoke Harm Reduction," Cannabis Therapeutics in HIV/AIDS: 153-170 (2001).

Gieringer., "Marijuana Water Pipe and Vaporizer Study," MAPS, 6(3): 7 pages (1996).

Hanus et al., "Phytocannabinoids: a unified critical inventory," Natural Product Reports, 33: 1357-1392 (2016).

Hazekamp et al., "Evaluation of a Vaporizing Device (Volcano®) for the Pulmonary Administration of Tetrahydrocannabinol," Journal of Pharmaceutical Sciences:11 pages (2006).

International Search Report and Written Opinion for International Application No. PCT/US2021/012778 dated Jun. 22, 2021.

Kuppers et al., "Cannabis—VIII: Pyrolysis of Cannabidiol. Structure elucidation of the main pyrolytic product," Tetrahedron, 29: 2797-2802 (1973).

(56) References Cited

OTHER PUBLICATIONS

Lanz et al., "Medicinal Cannabis: In Vitro Validation of Vaporizers for the Smoke-Free Inhalation of Cannabis," Plos One 11(1): e0147286 pp. 1-18 (2016).
Osman et al., "Analysis of Cannabis Using Tenax-GC," Journal of the Forensic Science Society, 25(5): 377-384 (1985).
Pomahacova et al., "Cannabis smoke condensate III: The cannabinoid content of vaporised Cannabis sativa," Inhalation Toxicology, 21(13): 1108-1112 (2009).
Repetto et al., "Separation of Cannabinoids," Bulletin on Narcotics, 28(4): 69-74 (1976).
Sheehan et al., "Chemical and physical variations of cannabis smoke from a variety of cannabis samples in New Zealand," Forensic Sciences Research, 4(2): 168-178 (2019).
Spronck et al., "Pyrolysis of cannabinoids: a model experiment in the study of cannabis smoking," UNODC—Bulletin of Narcotics, 3-006: 4 pages (1978).
Vita et al., "Comparison of different methods for the extraction of cannabinoids from cannabis," Natural Product Research: 9 pages (2019).

* cited by examiner

METHODS FOR OBTAINING COMPOUNDS FROM A PLANT OR FUNGUS MATERIAL, RESPECTIVE COMPOSITIONS, AND USES THEREOF

CROSS-REFERENCE TO RELATED APPLICATIONS

This application is a continuation of International Application No. PCT/US2021/012778, which designated the United States and was filed on Jan. 8, 2021, published in English, which claims the benefit of U.S. Provisional Application No. 62/959,632, filed Jan. 10, 2020. The entire teachings of the above application(s) are incorporated herein by reference.

BACKGROUND OF THE INVENTION

Humans have harnessed the therapeutic potential of smoke extracts derived from specific plants for thousands of years; nearly every organ and regulatory system in the human body has been manipulated with smoke extracts for medicinal purposes. There are over a thousand documented medicinal uses for smoke extracts.

Though many remain uncharacterized, the therapeutic benefits of plant-derived smoke extracts can be attributed to unique combinations of secondary metabolites, or phytochemicals, present in various physiological structures of the parent plant. The primary method of ingestion for personal use has historically been by inhalation of combusted and/or vaporized plant matter. However, the extraction of desired compounds in a bioavailable, topically or orally ingestible form increases the range of therapeutic application, enables consistency and precision of dosing, has a longer duration of action, and decreases potential negative effects of inhaling the non-desirable combusted plant matter or pollutants.

Extraction systems and methods using aqueous solvents, non-aqueous solvents, or gases under high pressure (supercritical conditions) have been documented. These procedures create crude extracts that contain varying amounts of non-desirable plant matter solubilized along with the compounds of interest. The crude extract is further refined into a partially purified or fully purified form, typically requiring multiple steps involving a form of column chromatography.

Existing methods are disadvantageous from multiple angles, but namely in complexity of processing (the total number of manipulations and/or reactions that yield a final product) relative to purity of the specific compound(s) of interest from parent plant matter or fungal matter, and in limitations in extracted formulations that do not reflect the full therapeutic potential of the plant or fungal matter. New methodology reducing the complexity of the processing and improving the purity and/or efficacy of compound(s) of interest is needed.

SUMMARY OF THE INVENTION

A first embodiment of the present disclosure relates to a method for obtaining compounds from a plant or fungus material, comprising
(a) forming a gaseous composition by thermally treating the plant or fungus material;
(b) contacting the gaseous composition with an affinity medium; and
(c) separating the compounds from the affinity medium.

A second embodiment of the present disclosure relates to an apparatus for obtaining compounds from a plant or fungus material, comprising a) an enclosure configured for thermal treatment of the plant or fungus material and for enclosing a gaseous composition resulting from the thermal treatment; b) an affinity medium; c) a porous membrane positioned such that the gaseous composition contacts the porous membrane before contacting the affinity medium; and d) a vacuum source configured to lower pressure within the affinity medium.

A third embodiment of the present disclosure relates to an apparatus for obtaining compounds from a plant or fungus material, comprising a) an enclosure configured for thermal treatment of the plant or fungus material and for enclosing a gaseous composition resulting from the thermal treatment; b) an affinity medium in fluid communication with the enclosure; c) a vacuum source configured to provide negative pressure to the affinity medium; and d) an exhaust filter in fluid communication with the affinity medium and the vacuum source.

The methods, apparatus and systems of the present disclosure can be used to obtain compounds from plant or fungus material. Accordingly, the present disclosure further relates to compounds and compositions comprising such compounds.

A fourth embodiment is a composition comprising cannabidiol and one or more cannabidiol derivatives prepared by thermally treating the cannabidiol, and a solvent.

A fifth embodiment is a composition comprising cannabidiol and one or more cannabidiol derivatives prepared by thermally treating the cannabidiol, and a carrier, e.g., a pharmaceutically acceptable carrier.

A sixth embodiment is a composition comprising cannabidiol and one or more cannabidiol derivatives, wherein a first cannabidiol derivative of the one or more cannabidiol derivatives is characterized by a relative retention time (relative to the cannabidiol's retention time) selected from about 0.677, about 0.892, about 0.951, about 1.087, and about 1.111.

A seventh embodiment is a composition obtained by the method embodiments described herein, comprising cannabidiol, cannabinodiol, and at least one compound selected from o-methylcannabidiol, o-methylcannabinol, o-propylcannabinol, and o-pentylcannabinol.

A eighth embodiments is a liquid or solid composition comprising cannabidiol, cannabinodiol, and at least one compound selected from o-methylcannabidiol, o-methylcannabinol, o-propylcannabinol, and o-pentylcannabinol.

A ninth embodiment is a liquid or solid composition, comprising $\Delta 9$-tetrahydrocannabinol, cannabinol, and at least one compound selected from o-methylcannabinol, o-propylcannabinol, and o-pentylcannabinol.

A tenth embodiment is a composition obtained by the method embodiments described herein, comprising $\Delta 9$-tetrahydrocannabinol, cannabinol, and at least one compound selected from o-methylcannabinol, o-propylcannabinol, and o-pentylcannabinol.

An eleventh embodiment is a solid or liquid composition comprising cannabinol, $\Delta 9$-tetrahydrocannabinol and exo-tetrahydrocannabinol, wherein the cannabinol is present in the composition from about 5 wt. % to about 50 wt. %, the $\Delta 9$-tetrahydrocannabinol is present in the composition from about 1 wt. % to about 15 wt. %, and the exo-tetrahydrocannabinol is present in the composition from about 1 wt. % to about 5 wt. %.

A twelfth embodiment is a solid or liquid composition comprising cannabinol, $\Delta 9$-tetrahydrocannabinol, and $\Delta 10$-tetrahydrocannabinol, wherein the cannabinol is present in the composition from about 5 wt. % to about 50 wt. %, the Δ9-tetrahydrocannabinol is present in the composition from about 1 wt. % to about 15 wt. %, and the Δ10-tetrahydrocannabinol is present in the composition from about 1 wt. % to about 5 wt. %.

The compositions and compounds of the present disclosure can be used for treating diseases or disorders. Accordingly, the present disclosure further relates to methods of treatment of diseases and disorders comprising administering such compositions and compounds.

A thirteenth embodiment a method of treating an autoimmune disorder, an inflammatory disorder, chronic pain, a mood disorder, or a developmental disorder, comprising administering a therapeutically effective amount of a liquid or solid composition comprising cannabidiol, cannabinodiol, and at least one compound selected from o-methylcannabidiol, o-methylcannabinol, o-propylcannabinol, and o-pentylcannabinol; a liquid or solid composition comprising Δ9-tetrahydrocannabinol, cannabinol, and at least one compound selected from o-methylcannabinol, o-propylcannabinol, and o-pentylcannabinol; a liquid or solid composition comprising cannabinol, Δ9-tetrahydrocannabinol and exo-tetrahydrocannabinol; or a liquid or solid composition comprising cannabinol, Δ9-tetrahydrocannabinol, and Δ10-tetrahydrocannabinol. Alternatively, the method comprises administering a therapeutically effective amount of a composition prepared by the method embodiments described herein, for example, a composition comprising cannabidiol, cannabinodiol, and at least one compound selected from o-methylcannabidiol, o-methylcannabinol, o-propylcannabinol, and o-pentylcannabinol; a composition comprising Δ9-tetrahydrocannabinol, cannabinol, and at least one compound selected from o-methylcannabinol, o-propylcannabinol, and o-pentylcannabinol; a composition comprising cannabinol, Δ9-tetrahydrocannabinol and exo-tetrahydrocannabinol; or a composition comprising cannabinol, Δ9-tetrahydrocannabinol, and Δ10-tetrahydrocannabinol.

A fourteenth embodiment is a method of treating disease or disorder selected from fibromyalgia, an Ehlers-Danlos syndrome, multiple sclerosis, epilepsy, Parkinson's disease, Huntington's disease, Alzheimer's disease, stroke, hypertension, atherosclerosis, muscle spasms, an inherited neuropathy, Crohn's disease, psoriasis, arthritis, Lyme disease, anxiety, post-traumatic stress disorder, an autism spectrum disorder, a schizophrenia spectrum disorder, and chronic migraine, comprising administering a therapeutically effective amount of a liquid or solid composition comprising cannabidiol, cannabinodiol, and at least one compound selected from o-methylcannabidiol, o-methylcannabinol, o-propylcannabinol, and o-pentylcannabinol; a liquid or solid composition comprising Δ9-tetrahydrocannabinol, cannabinol, and at least one compound selected from o-methylcannabinol, o-propylcannabinol, and o-pentylcannabinol; a liquid or solid composition comprising cannabinol, Δ9-tetrahydrocannabinol and exo-tetrahydrocannabinol; or a liquid or solid composition comprising cannabinol, Δ9-tetrahydrocannabinol, and Δ10-tetrahydrocannabinol. Alternatively, the method comprises administering a therapeutically effective amount of a composition prepared by the method embodiments described herein, for example, a composition comprising cannabidiol, cannabinodiol, and at least one compound selected from o-methylcannabidiol, o-methylcannabinol, o-propylcannabinol, and o-pentylcannabinol; a composition comprising Δ9-tetrahydrocannabinol, cannabinol, and at least one compound selected from o-methylcannabinol, o-propylcannabinol, and o-pentylcannabinol; a composition comprising cannabinol, Δ9-tetrahydrocannabinol and exo-tetrahydrocannabinol; or a composition comprising cannabinol, Δ9-tetrahydrocannabinol, and Δ10-tetrahydrocannabinol.

A fifteenth embodiment is a method of reducing anxiety comprising administering a therapeutically effective amount of a liquid or solid composition comprising cannabidiol, cannabinodiol, and at least one compound selected from o-methylcannabidiol, o-methylcannabinol, o-propylcannabinol, and o-pentylcannabinol; a liquid or solid composition comprising Δ9-tetrahydrocannabinol, cannabinol, and at least one compound selected from o-methylcannabinol, o-propylcannabinol, and o-pentylcannabinol; a liquid or solid composition comprising cannabinol, Δ9-tetrahydrocannabinol and exo-tetrahydrocannabinol; or a liquid or solid composition comprising cannabinol, Δ9-tetrahydrocannabinol, and Δ10-tetrahydrocannabinol. Alternatively, the method comprises administering a therapeutically effective amount of a composition prepared by the method embodiments described herein, for example, a composition comprising cannabidiol, cannabinodiol, and at least one compound selected from o-methylcannabidiol, o-methylcannabinol, o-propylcannabinol, and o-pentylcannabinol; a composition comprising Δ9-tetrahydrocannabinol, cannabinol, and at least one compound selected from o-methylcannabinol, o-propylcannabinol, and o-pentylcannabinol; a composition comprising cannabinol, Δ9-tetrahydrocannabinol and exo-tetrahydrocannabinol; or a composition comprising cannabinol, Δ9-tetrahydrocannabinol, and Δ10-tetrahydrocannabinol.

A sixteenth embodiment is a method of increasing sleep quality in a subject in need thereof, comprising administering a therapeutically effective amount of a liquid or solid composition comprising cannabidiol, cannabinodiol, and at least one compound selected from o-methylcannabidiol, o-methylcannabinol, o-propylcannabinol, and o-pentylcannabinol; a liquid or solid composition comprising Δ9-tetrahydrocannabinol, cannabinol, and at least one compound selected from o-methylcannabinol, o-propylcannabinol, and o-pentylcannabinol; a liquid or solid composition comprising cannabinol, Δ9-tetrahydrocannabinol and exo-tetrahydrocannabinol; or a liquid or solid composition comprising cannabinol, Δ9-tetrahydrocannabinol, and Δ10-tetrahydrocannabinol. Alternatively, the method comprises administering a therapeutically effective amount of a composition prepared by the method embodiments described herein, for example, a composition comprising cannabidiol, cannabinodiol, and at least one compound selected from o-methylcannabidiol, o-methylcannabinol, o-propylcannabinol, and o-pentylcannabinol; a composition comprising Δ9-tetrahydrocannabinol, cannabinol, and at least one compound selected from o-methylcannabinol, o-propylcannabinol, and o-pentylcannabinol; a composition comprising cannabinol, Δ9-tetrahydrocannabinol and exo-tetrahydrocannabinol; or a composition comprising cannabinol, Δ9-tetrahydrocannabinol, and Δ10-tetrahydrocannabinol.

The invention also relates to the use of a compound or composition described herein for the manufacture of a medicament for treating a subject having any of the disorders or conditions described herein.

The invention also relates to the compound or composition described herein for treating a subject having a disorder or indication described herein.

BRIEF DESCRIPTION OF THE DRAWINGS

The foregoing will be apparent from the following more particular description of example embodiments of the inven

DETAILED DESCRIPTION OF THE INVENTION

Figure 1:
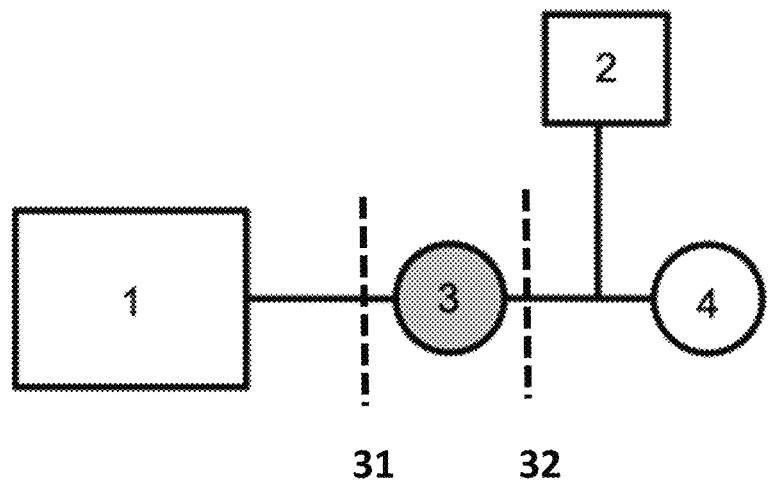
- FIG. 1 is a schematic representation of the apparatus for obtaining compounds from a plant or fungus material (1—enclosure for thermal treatment of the plant or fungus material; 2—vacuum source; 3—affinity medium; 31—optional porous membrane; 32—optional structural support for the affinity medium which can be a porous membrane; 4—optional exhaust filter).

In some embodiments, the present disclosure relates to a method for obtaining compounds from a plant or fungus material. For example, the present disclosure relates to a method for obtaining cannabidiol (CBD) from plants of the *Cannabis* genus of flowering plants in the family Cannabaceae. CBD is a lipophilic compound produced by *Cannabis sativa, Cannabis indica,* and *Cannabis ruderalis. Cannabis* material is defined as "hemp" if it contains less than 0.3% of the total amount of Δ9-tetrahydrocannabinol (Δ9THC) and tetrahydrocannabinolic acid (THCA). Any *Cannabis* material that contains more than 0.3% of the total amount of Δ9THC and THCA is considered to be medical *Cannabis*. The plant varieties contain different amounts of CBD, with hemp producing higher concentrations of CBD and lower concentrations of the psychoactive cannabinoids, for example, Δ9-tetrahydrocannabinol (THC). CBD is known to have a wide scope of applications to multiple medical conditions. CBD use is attractive, since it has little or no side effects and does not interfere with psychomotor, learning, and/or psychological functions of users.

The most prevalent mode of use of *cannabis* is by smoking. However, smoking *cannabis* has serious disadvantages, since *cannabis* smoke carries more tar and other particulate matter than tobacco smoke. Therefore, direct inhalation of *cannabis* smoke can contribute to development of lung diseases including lung cancer. Moreover, since inhaled *cannabis* is short acting in pain reduction, it has to be smoked several times a day to maintain the physiological benefits. Therefore, methods of isolation and concentration of *cannabis* smoke components, which can then be ingested in a safe and controlled manner, are needed.

A description of example embodiments of the invention follows.

In some embodiments, the present disclosure relates to a method for obtaining compounds from a plant or fungus material, comprising
(a) forming a gaseous composition by thermally treating the plant or fungus material;
(b) contacting the gaseous composition with an affinity medium; and
(c) separating the compounds from the affinity medium.

In some embodiments, the method comprises further purifying the isolated compounds, for example, by vacuum distillation or column chromatography.

In some embodiments, the gaseous composition is contacted with two or more affinity media.

In some embodiments, contacting the gaseous composition with the affinity medium comprises passing the gaseous composition through the affinity medium.

In some embodiments, the gaseous composition is contacted with the affinity medium at least two times.

In some embodiments, the plant or fungus material is a raw plant or fungus material, a dried plant or fungus material, a raw biomass, a dried biomass, or a plant or fungus material concentrate.

In some embodiments, the plant material is a whole plant or parts of a plant.

In some embodiments, the plant material is a plant stem, plant leaf, plant flower, plant root, plant trichome, plant seed, plant fruit, or a mixture thereof.

In some embodiments, the plant material is a plant flower.

In some embodiments, the plant material is a whole plant.

In some embodiments, the plant material concentrate is a plant wax, a plant extract, a plant resin, a plant distillate, or a mixture thereof.

In some embodiments, the plant material is raw *Cannabis sativa* biomass, dried *Cannabis sativa* biomass, raw *Cannabis sativa* flower, dried *Cannabis sativa* flower, *Cannabis sativa* trichomes, *Cannabis sativa* concentrate, cannabidiol (CBD) isolate, cannabigerol (CBG) isolate, or cannabichromene (CBC) isolate.

In some embodiments, thermally treating the plant or fungus material comprises heating the plant or fungus material to a temperature from about 50° C. to about 1000° C.

In some embodiments, the temperature is from about 100° C. to about 600° C.

In some embodiments, the temperature is from about 200° C. to about 500° C.

In some embodiments, thermally treating the plant or fungus material comprises heating the plant or fungus material for a period of time from about 1 minute to about 10 hours.

In some embodiments, the time period is from about 5 minutes to about 8 hours.

In some embodiments, the time period is from about 15 minutes to about 4 hours.

In some embodiments, forming the gaseous composition comprises heating the plant or fungus material in a sealed vessel.

In some embodiments, forming the gaseous composition comprises heating the plant or fungus material in a vessel equipped with a gas flow opening.

In some embodiments, the method comprises applying reduced pressure from about 250 Torr to about 0.1 Torr to a vessel in which the plant or fungus material is being thermally treated.

In some embodiments, the affinity medium is a lipophilic affinity medium.

In some embodiments, the lipophilic affinity medium comprises particles; the particles comprise a core and a plurality of lipophilic groups; and each lipophilic group of the plurality of lipophilic groups is attached to the core.

In some embodiments, each lipophilic group of the plurality of lipophilic groups independently comprises $C_{2-30}$ alkyl, $C_{6-12}$ aryl, $C_{2-24}$ alkyl($C_{6-12}$ aryl), tri($C_{1-12}$ alkyl)silyl, di($C_{1-12}$ alkyl)silyl($C_{2-24}$ alkyl).

In some embodiments, the affinity medium is a hydrophilic affinity medium.

In some embodiments, the hydrophilic affinity medium comprises particles; the particles comprise a core and a plurality of hydrophilic groups; and each hydrophilic of the plurality of hydrophilic groups is attached to the core.

In some embodiments, each hydrophilic group of the plurality of hydrophilic groups independently comprises —$NH_2$, —$C_6H_5SO_3H$, ($C_{1-12}$ alkyl)($C_6F_5$), diol, silanol, or zwitterion.

In some embodiments, the gaseous composition is contacted with two or more affinity media and at least one affinity medium is a hydrophilic affinity medium and at least one affinity medium is a hydrophobic affinity medium.

In some embodiments, the affinity medium comprises a molecularly imprinted polymer.

In some embodiments, the molecularly imprinted polymer comprises polyacrylamide, polystyrene, polyisoprene, or polymethacrylic acid.

In some embodiments, each affinity medium comprises pores.

In some embodiments, the pore size of the affinity medium is from about 90 Å to about 200 Å.

In some embodiments, the gaseous composition contacts at least one porous membrane prior to contacting the affinity medium.

In some embodiments, each porous membrane comprises pores, wherein the size of the pores of each porous membrane is independently from about 5 µm to about 50 µm.

In some embodiments, the size of the pores of each porous membrane is about 20 µm.

In some embodiments, the core of the affinity medium comprises silica, a polymer, or a combination thereof.

In some embodiments, the longest dimension of the affinity medium is no more than twice the size of the shortest dimension of the affinity medium.

In some embodiments, the affinity medium is heated to a temperature from about 25° C. to about 50° C.

In some embodiments, the affinity medium is cooled to a temperature from about 15° C. to about 0° C.

In some embodiments, the method further comprises passing the gaseous composition through an aqueous solution.

In some embodiments, the aqueous solution comprises NaCl, KCl, $MgSO_4$, $NaHCO_3$, $K_2CO_3$, LiCl, $Na_2CO_3$, $H_3PO_4$, HCl, LiOH, KOH, NaOH, detergent, purified protein, or recombinant protein.

In some embodiments, the aqueous solution comprises a buffer.

In some embodiments, the buffer is a citric buffer, a phosphate buffer, an acetate buffer, or a borate buffer.

In some embodiments, the aqueous solution has pH from about 1 to about 8.

In some embodiments, the aqueous solution is heated to a temperature from about 30° C. to about 70° C.

In some embodiments, the aqueous solution is cooled to a temperature from about 15° C. to about 5° C.

In some embodiments, the method further comprises contacting the affinity medium with a washing solution after the affinity medium is contacted with the gaseous composition.

In some embodiments, the washing solution comprises water, NaCl, KCl, $MgSO_4$, $NaHCO_3$, $K_2CO_3$, LiCl, $Na_2CO_3$, $H_3PO_4$, HCl, LiOH, KOH, NaOH, detergent, purified protein, recombinant protein, or mixtures thereof.

In some embodiments, the washing solutions is an aqueous composition including one or more of NaCl, KCl, $MgSO_4$, $NaHCO_3$, $K_2CO_3$, LiCl, $Na_2CO_3$, $H_3PO_4$, HCl, LiOH, KOH, NaOH, detergent, and purified protein, recombinant protein.

In some embodiments, the washing solution further comprises water, methanol, ethanol, propanol, isopropanol, acetonitrile, or mixtures thereof.

In some embodiments, the washing solution comprises a buffer.

In some embodiments, the buffer is a citric buffer, a phosphate buffer, an acetate buffer, or a borate buffer.

In some embodiments, the washing solution has pH from about 1 to about 8.

In some embodiments, the washing solution is heated to a temperature from about 30° C. to about 70° C.

In some embodiments, washing solution is cooled to a temperature from about 15° C. to about 5° C.

In some embodiments, the volume of the washing solution is from about 5 to about 50 times larger than the volume of the affinity medium.

In some embodiments, separating the compounds from the affinity medium comprises contacting the affinity medium with an elution solution, thereby providing an elution mixture.

In some embodiments, the elution solution comprises a solvent, wherein the solvent is methanol, ethanol, a methanol/water mixture, an ethanol/water mixture, pentane, hexane, heptane, cyclohexane, acetone, tetrahydrofuran, ethyl acetate, diethyl ether, chloroform, or mixtures thereof.

In some embodiments, the elution solution is heated to a temperature from about 25° C. to about 50° C.

In some embodiments, the elution solution is cooled to a temperature from about 15° C. to about 5° C.

In some embodiments, the method further comprises removing the solvent from the elution mixture.

In some embodiments, the solvent is removed by evaporation.

In some embodiments, the solvent is removed by lyophilization.

In some embodiments, separating the compounds from the affinity medium further comprises separating the elution mixture by chromatography.

In some embodiments, separating the compounds from the affinity medium further comprises separating the elution mixture by fractionation, e.g. fractionation by solubility.

In some embodiments, the compounds comprise one or more natural compounds.

In some embodiments, the natural compound is CBD or THC.

In some embodiments, the method further comprises adiabatically expanding the gaseous composition prior to contacting the gaseous composition with the affinity medium, thereby producing a first fraction of the compounds.

In some embodiments, the volume of the gaseous composition is increased by about 100 fold to about 1000 fold as compared to the volume prior to adiabatically expanding. For example, the volume of the gaseous composition is increased by about 100 fold, about 200 fold, about 300 fold, about 400 fold, about 500 fold, or about 1000 fold as compared to the volume prior to adiabatically expanding.

In some embodiments, the volume of the gaseous compositions is increased by about 250 fold.

In some embodiments, the ratio by weight of the first fraction to the compounds separated from the affinity medium is from about 1:10 to about 10:1, e.g., 1:10, 1:5, 1:2.5, 1:1, 2.5:1, 5:1, or 10:1.

In some embodiments, the ratio by weight of the first fraction to the compounds separated from the affinity medium is 1:1.

In some embodiments, the plant material is raw *Cannabis sativa* biomass, dried *Cannabis sativa* biomass, raw *Cannabis sativa* flower, dried *Cannabis sativa* flower or *Cannabis sativa* trichomes.

In some embodiments, the present disclosure relates to an apparatus for obtaining compounds from a plant or fungus material, comprising a) an enclosure configured for thermal treatment of the plant or fungus material and for enclosing a gaseous composition resulting from the thermal treatment;

b) an affinity medium;

c) a porous membrane positioned such that the gaseous composition contacts the porous membrane before contacting the affinity medium; and d) a vacuum source configured to lower pressure within the affinity medium.

In some embodiments, the porous membrane contacts the affinity medium.

In some embodiments, the porous membrane encapsulates the affinity medium.

In some embodiments, the enclosure comprises at least one gas flow opening.

In some embodiments, the apparatus further comprises a cleaning medium positioned such that the gaseous composition contacts the cleaning medium before contacting the affinity medium.

In some embodiments, the cleaning medium comprises is a liquid.

In some embodiments, the cleaning medium is a liquid comprising water, NaCl, KCl, $MgSO_4$, $NaHCO_3$, $K_2CO_3$, LiCl, $Na_2CO_3$, $H_3PO_4$, HCl, LiOH, KOH, NaOH, detergent, purified protein, recombinant protein, or mixtures thereof.

In some embodiments, the liquid is selected from water, methanol, ethanol, propanol, isopropanol, or acetonitrile.

A further embodiment is an apparatus for obtaining compounds from a plant or fungus material, comprising a) an enclosure configured for thermal treatment of the plant or fungus material and for enclosing a gaseous composition resulting from the thermal treatment;

b) an affinity medium in fluid communication with the enclosure;

c) a vacuum source configured to provide negative pressure to the affinity medium; and d) an optional exhaust filter in fluid communication with the affinity medium and the vacuum source.

In some embodiments, the enclosure is connected to the affinity medium by a variable diameter connector.

In some embodiments, the variable diameter connector has a first portion proximal to the enclosure and having a first inner diameter and a second portion distal to the enclosure and having a second inner diameter different from the first inner diameter wherein the ratio of the first inner diameter to the second inner diameter is from about 1:10 to about 1:30. For example, the ratio of the first inner diameter to the second inner diameter is 1:10, 1:15, 1:20, 1:25 or 1:30, such as 1:15.

A further embodiment is a composition comprising one or more compounds obtained by the method of any one of the method embodiments disclosed herein.

In some embodiments, the one or more compounds in the composition include cannabidiol.

In some embodiments, the one or more compounds in the composition include cannabidiol and one or more cannabidiol derivatives.

In some embodiments, the one or more compounds in the composition include cannabidiol and at least two cannabidiol derivatives.

In some embodiments, the one or more compounds in the composition include cannabidiol and at least three cannabidiol derivatives.

In some embodiments, the one or more compounds in the composition include cannabidiol and at least one cannabidiol derivative, wherein the at least one cannabidiol derivative is characterized by one relative retention time (relative to the cannabidiol's retention time) selected from about 0.677, about 0.892, about 0.951, about 1.087, and about 1.111.

In some embodiments, the one or more compounds in the composition include cannabidiol and at least two cannabidiol derivatives, wherein the at least two cannabidiol derivative are each characterized by one relative retention time (relative to the cannabidiol's retention time) selected from about 0.677, about 0.892, about 0.951, about 1.087, and about 1.111.

In some embodiments, the one or more compounds in the composition include cannabidiol and at least three cannabidiol derivatives, wherein the at least three cannabidiol derivative are each characterized by one relative retention time (relative to the cannabidiol's retention time) selected from about 0.677, about 0.892, about 0.951, about 1.087, and about 1.111.

In some embodiments, the one or more compounds in the composition comprise cannabidiol and at least four cannabidiol derivatives, wherein a first of the at least four cannabidiol derivatives is characterized by a relative retention time (relative to the cannabidiol's retention time) of about 0.677, a second of the at least four cannabidiol derivatives is characterized by a relative retention time (relative to the cannabidiol's retention time) of about 0.892, a third of the at least four cannabidiol derivatives is characterized by a relative retention time (relative to the cannabidiol's retention time) of about 1.087, and a fourth of the at least four cannabidiol derivatives is characterized by a relative retention time (relative to the cannabidiol's retention time) of about 1.111.

In some embodiments, the one or more compounds in the composition comprise cannabidiol and at least four cannabidiol derivatives, wherein a first of the at least five cannabidiol derivatives is characterized by a relative retention time (relative to the cannabidiol's retention time) of about 0.677, a second of the at least five cannabidiol derivatives is characterized by a relative retention time (relative to the cannabidiol's retention time) of about 0.892, a third of the at least five cannabidiol derivatives is characterized by a relative retention time (relative to the cannabidiol's retention time) of about 1.087, a fourth of the at least five cannabidiol derivatives is characterized by a relative retention time (relative to the cannabidiol's retention time) of about 1.111, and a fifth of the at least five cannabidiol derivatives is characterized by a relative retention time (relative to the cannabidiol's retention time) of about 0.951.

In some embodiments, the cannabidiol derivatives result from oxidation, isomerization and/or transformation of cannabidiol due to the thermal treatment of plant material containing the cannabidiol.

Another embodiment is a composition comprising cannabidiol and one or more cannabidiol derivatives prepared by thermally treating the cannabidiol, and a solvent.

In some embodiments, the composition comprises cannabidiol and one or more cannabidiol derivatives that are dissolved in a solvent.

Another embodiment is a composition comprising cannabidiol and one or more cannabidiol derivatives prepared by thermally treating the cannabidiol, and a carrier, e.g., a pharmaceutically acceptable carrier.

In some embodiments, the one or more cannabidiol derivatives in the composition were prepared by thermally treating the cannabidiol at a temperature above about 150° C.

In some embodiments, the one or more cannabidiol derivatives in the composition were prepared by thermally treating the cannabidiol at a temperature above about 300° C.

Another embodiment is a composition comprising cannabidiol and one or more cannabidiol derivatives, wherein a first cannabidiol derivative of the one or more cannabidiol derivatives is characterized by a relative retention time (relative to the cannabidiol's retention time) selected from about 0.677, about 0.892, about 0.951, about 1.087, and about 1.111.

In some embodiments, the composition comprises an amount of the first cannabidiol derivative which is at least about 2% of the amount of cannabidiol in the composition.

In some embodiments, a first cannabidiol derivative of the one or more cannabidiol derivatives is characterized by a relative retention time (relative to the cannabidiol's retention time) selected from about 0.677, about 0.892, about 0.951, about 1.087, and about 1.111, and a second cannabidiol derivative of the one or more cannabidiol derivatives is characterized by a relative retention time (relative to the cannabidiol's retention time) selected from about 0.677, about 0.892, about 0.951, about 1.087, and about 1.111, wherein the first and second cannabidiol derivatives are characterized by different relative retention times.

In some embodiments, the composition comprises an amount of a first cannabidiol derivative which is at least about 2% of the amount of cannabidiol in the composition, and an amount of a second cannabidiol derivative which is at least about 2% of the amount of cannabidiol in the composition.

In some embodiments, a first cannabidiol derivative of the one or more cannabidiol derivatives in the composition is characterized by a relative retention time (relative to the cannabidiol's retention time) selected from about 0.677, about 0.892, about 0.951, about 1.087, and about 1.111, a second cannabidiol derivative of the one or more cannabidiol derivatives is characterized by a relative retention time (relative to the cannabidiol's retention time) selected from about 0.677, about 0.892, about 0.951, about 1.087, and about 1.111, and a third cannabidiol derivative of the one or more cannabidiol derivatives is characterized by a relative retention time (relative to the cannabidiol's retention time) selected from about 0.677, about 0.892, about 0.951, about 1.087, and about 1.111, wherein the first, second and third cannabidiol derivatives are characterized by different relative retention times.

In some embodiments, the composition comprises an amount of a first cannabidiol derivative which is at least about 2% of the amount of cannabidiol in the composition, an amount of a second cannabidiol derivative which is at least about 2% of the amount of cannabidiol in the composition, and an amount of a third cannabidiol derivative which is at least about 2% of the amount of cannabidiol in the composition.

In some embodiments, a first cannabidiol derivative of the one or more cannabidiol derivatives in the composition is characterized by a relative retention time (relative to the cannabidiol's retention time) of about 0.677, a second cannabidiol derivative of the one or more cannabidiol derivatives is characterized by a relative retention time (relative to the cannabidiol's retention time) of about 0.892, a third cannabidiol derivative of the one or more cannabidiol derivatives is characterized by a relative retention time (relative to the cannabidiol's retention time) of about 1.087, and a fourth cannabidiol derivative of the one or more cannabidiol derivatives is characterized by a relative retention time (relative to the cannabidiol's retention time) of about 1.111.

In some embodiments, the composition comprises an amount of a first cannabidiol derivative which is at least about 2% of the amount of cannabidiol in the composition, an amount of a second cannabidiol derivative which is at least about 2% of the amount of cannabidiol in the composition, an amount of the a cannabidiol derivative which is at least about 2% of the amount of cannabidiol in the composition, and an amount of a fourth cannabidiol derivative which is at least about 2% of the amount of cannabidiol in the composition.

In some embodiments, a first cannabidiol derivative of the one or more cannabidiol derivatives in the composition is characterized by a relative retention time (relative to the cannabidiol's retention time) of about 0.677, a second cannabidiol derivative of the one or more cannabidiol derivatives is characterized by a relative retention time (relative to the cannabidiol's retention time) of about 0.892, a third cannabidiol derivative of the one or more cannabidiol derivatives is characterized by a relative retention time (relative to the cannabidiol's retention time) of about 1.087, a fourth cannabidiol derivative of the one or more cannabidiol derivatives is characterized by a relative retention time (relative to the cannabidiol's retention time) of about 1.111, and a fifth cannabidiol derivative of the one or more cannabidiol derivatives is characterized by a relative retention time (relative to the cannabidiol's retention time) of about 0.951.

In some embodiments, the composition comprises an amount of a first cannabidiol derivative which is at least about 2% of the amount of cannabidiol in the composition, an amount of a second cannabidiol derivative which is at least about 2% of the amount of cannabidiol in the composition, an amount of a third cannabidiol derivative which is at least about 2% of the amount of cannabidiol in the composition, an amount of a fourth cannabidiol derivative which is at least about 2% of the amount of cannabidiol in the composition, and an amount of a fifth cannabidiol derivative which is at least about 2% of the amount of cannabidiol in the composition.

In some embodiments, the composition is not a gas mixture.

In some embodiments, the composition is a liquid or solid composition.

In some embodiments, the composition is a pharmaceutical composition.

A further embodiment is a cannabidiol derivative obtained by the method embodiments described herein, characterized by a relative retention time of selected from about 0.677, about 0.892, about 0.951, about 1.087, and about 1.111.

Another embodiment is a method of treating spasticity, anorexia, nausea, pain, tobacco addiction, acne, fibromyalgia, anxiety, inflammation, schizophrenia or insomnia in a subject in need thereof, comprising administering a therapeutically effective amount of a liquid or solid composition comprising cannabidiol, cannabinodiol, and at least one compound selected from o-methylcannabidiol, o-methylcannabinol, o-propylcannabinol, and o-pentylcannabinol; a liquid or solid composition comprising Δ9-tetrahydrocannabinol, cannabinol, and at least one compound selected from o-methylcannabinol, o-propylcannabinol, and o-pentylcannabinol; a liquid or solid composition comprising cannabinol, Δ9-tetrahydrocannabinol and exo-tetrahydrocannabinol; or a liquid or solid composition comprising cannabinol, Δ9-tetrahydrocannabinol, and Δ10-tetrahydrocannabinol. Alternatively, the method comprises administering a therapeutically effective amount of a composition prepared by the method embodiments described herein, for example, a composition comprising cannabidiol, cannabinodiol, and at least one compound selected from o-methylcannabidiol, o-methylcannabinol, o-propylcannabinol, and o-pentylcannabinol; a composition comprising Δ9-tetrahydrocannabinol, cannabinol, and at least one compound selected from o-methylcannabinol, o-propylcannabinol, and o-pentylcannabinol; a composition comprising cannabinol, Δ9-tetrahydrocannabinol and exo-tetrahydrocannabinol; or a composition comprising cannabinol, Δ9-tetrahydrocannabinol, and Δ10-tetrahydrocannabinol.

In some embodiments, the present disclosure relates to a method of treating an autoimmune disorder, an inflammatory disorder, chronic pain, a mood disorder, or a developmental disorder, comprising administering a therapeutically effective amount of a liquid or solid composition comprising cannabidiol, cannabinodiol, and at least one compound selected from o-methylcannabidiol, o-methylcannabinol, o-propylcannabinol, and o-pentylcannabinol; a liquid or solid composition comprising Δ9-tetrahydrocannabinol, cannabinol, and at least one compound selected from o-methylcannabinol, o-propylcannabinol, and o-pentylcannabinol; a liquid or solid composition comprising cannabinol, Δ9-tetrahydrocannabinol and exo-tetrahydrocannabinol; or a liquid or solid composition comprising cannabinol, Δ9-tetrahydrocannabinol, and Δ10-tetrahydrocannabinol. Alternatively, the method comprises administering a therapeutically effective amount of a composition prepared by the method embodiments described herein, for example, a composition comprising cannabidiol, cannabinodiol, and at least one compound selected from o-methylcannabidiol, o-methylcannabinol, o-propylcannabinol, and o-pentylcannabinol; a composition comprising Δ9-tetrahydrocannabinol, cannabinol, and at least one compound selected from o-methylcannabinol, o-propylcannabinol, and o-pentylcannabinol; a composition comprising cannabinol, Δ9-tetrahydrocannabinol and exo-tetrahydrocannabinol; or a composition comprising cannabinol, Δ9-tetrahydrocannabinol, and Δ10-tetrahydrocannabinol.

In some embodiments, the present disclosure relates to a method of treating disease or disorder selected from fibromyalgia, an Ehlers-Danlos syndrome, multiple sclerosis, epilepsy, Parkinson's disease, Huntington's disease, Alzheimer's disease, stroke, hypertension, atherosclerosis, muscle spasms, an inherited neuropathy, Crohn's disease, psoriasis, arthritis, Lyme disease, anxiety, post-traumatic stress disorder, an autism spectrum disorder, a schizophrenia spectrum disorder, and chronic migraine, comprising administering a therapeutically effective amount of a liquid or solid composition comprising cannabidiol, cannabinodiol, and at least one compound selected from o-methylcannabidiol, o-methylcannabinol, o-propylcannabinol, and o-pentylcannabinol; a liquid or solid composition comprising Δ9-tetrahydrocannabinol, cannabinol, and at least one compound selected from o-methylcannabinol, o-propylcannabinol, and o-pentylcannabinol; a liquid or solid composition comprising cannabinol, Δ9-tetrahydrocannabinol and exo-tetrahydrocannabinol; or a liquid or solid composition comprising cannabinol, Δ9-tetrahydrocannabinol, and Δ10-tetrahydrocannabinol. Alternatively, the method comprises administering a therapeutically effective amount of a composition prepared by the method embodiments described herein, for example, a composition comprising cannabidiol, cannabinodiol, and at least one compound selected from o-methylcannabidiol, o-methylcannabinol, o-propylcannabinol, and o-pentylcannabinol; a composition comprising Δ9-tetrahydrocannabinol, cannabinol, and at least one compound selected from o-methylcannabinol, o-propylcannabinol, and o-pentylcannabinol; a composition comprising cannabinol, Δ9-tetrahydrocannabinol and exo-tetrahydrocannabinol; or a composition comprising cannabinol, Δ9-tetrahydrocannabinol, and Δ10-tetrahydrocannabinol.

In some embodiments, the disease or disorder is selected from an inherited neuropathy, Crohn's disease, psoriasis, arthritis, Lyme disease, anxiety, post-traumatic stress disorder, an autism spectrum disorder, a schizophrenia spectrum disorder, and chronic migraine.

In some embodiments, the disease or disorder is an inherited neuropathy selected from hereditary motor and sensory neuropathy (HMSN, also known as Charcot-Marie-Tooth (CMT) Hereditary Neuropathy), hereditary sensory and autonomic neuropathy (HSAN), hereditary sensory neuropathy (HSN), distal hereditary motor neuropathy (dHMN), hereditary brachial plexus neuropathy (HBPN), and hereditary neuropathy with liability to pressure palsies (HNPP).

In some embodiments, the present disclosure relates to a method of reducing anxiety and promoting relaxation in a subject in need thereof, comprising administering a therapeutically effective amount of a composition prepared by the method embodiments described herein.

In some embodiments, the present disclosure relates to a method of increasing sleep quality in a subject in need thereof, comprising administering a therapeutically effective amount of a liquid or solid composition comprising cannabidiol, cannabinodiol, and at least one compound selected from o-methylcannabidiol, o-methylcannabinol, o-propylcannabinol, and o-pentylcannabinol; a liquid or solid composition comprising Δ9-tetrahydrocannabinol, cannabinol, and at least one compound selected from o-methylcannabinol, o-propylcannabinol, and o-pentylcannabinol; a liquid or solid composition comprising cannabinol, Δ9-tetrahydrocannabinol and exo-tetrahydrocannabinol; or a composition comprising cannabinol, Δ9-tetrahydrocannabinol, and Δ10-tetrahydrocannabinol. Alternatively, the method comprises administering a therapeutically effective amount of a composition prepared by the method embodiments described herein, for example, a composition comprising cannabidiol, cannabinodiol, and at least one compound selected from o-methylcannabidiol, o-methylcannabinol, o-propylcannabinol, and o-pentylcannabinol; a composition comprising Δ9-tetrahydrocannabinol, cannabinol, and at least one compound selected from o-methylcannabinol, o-propylcannabinol, and o-pentylcannabinol; a composition comprising cannabinol, Δ9-tetrahydrocannabinol and exo-tetrahydrocannabinol; or a composition comprising cannabinol, Δ9-tetrahydrocannabinol, and Δ10-tetrahydrocannabinol.

In some embodiments, the subject is administered from 5 mg to 50 mg of a liquid or solid composition comprising cannabidiol, cannabinodiol, and at least one compound selected from o-methylcannabidiol, o-methylcannabinol, o-propylcannabinol, and o-pentylcannabinol; a liquid or solid composition comprising Δ9-tetrahydrocannabinol, cannabinol, and at least one compound selected from o-methylcannabinol, o-propylcannabinol, and o-pentylcannabinol; a liquid or solid composition comprising cannabinol, Δ9-tetrahydrocannabinol and exo-tetrahydrocannabinol; or a liquid or solid composition comprising cannabinol, Δ9-tetrahydrocannabinol, and Δ10-tetrahydrocannabinol. Alternatively, the administered composition is prepared by the method embodiments described herein, for example, a composition comprising cannabidiol, cannabinodiol, and at least one compound selected from o-methylcannabidiol, o-methylcannabinol, o-propylcannabinol, and o-pentylcannabinol; a composition comprising Δ9-tetrahydrocannabinol, cannabinol, and at least one compound selected from o-methylcannabinol, o-propylcannabinol, and o-pentylcannabinol; a composition comprising cannabinol, Δ9-tetrahydrocannabinol and exo-tetrahydrocannabinol; or a composition comprising cannabinol, Δ9-tetrahydrocannabinol, and Δ10-tetrahydrocannabinol.

The subject can be administered the solid or liquid composition or composition prepared according to the methods described herein from 7.5 mg to 45 mg, from 10 mg to 40 mg, from 10 mg to 30 mg, from 15 mg to 45 mg, from 20 mg to 40 mg, from 20 mg to 30 mg, from 25 mg to 30 mg, from 25 mg to 50 mg, or from 10 mg to 50 mg of the composition. In some embodiments, the subject is administered from 2 mg to 100 mg of the composition. In some embodiments, the subject is administered about 2 mg, about 5 mg, about 10 mg, about 15 mg, about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, or about 100 mg of the composition. In some embodiments, the subject is administered from 10 mg to 50 mg of the composition. In some embodiments, the subject is administered 15 mg of the composition.

In some embodiments, the liquid or solid composition comprises cannabidiol, cannabinodiol, and at least one compound selected from o-methylcannabidiol, o-methylcannabinol, o-propylcannabinol, and o-pentylcannabinol; Δ9-tetrahydrocannabinol, cannabinol, and at least one compound selected from o-methylcannabinol, o-propylcannabinol, and o-pentylcannabinol; cannabinol, Δ9-tetrahydrocannabinol, and exo-tetrahydrocannabinol; or cannabinol, Δ9-tetrahydrocannabinol, and Δ10-tetrahydrocannabinol. In other embodiment, the composition is prepared by the method embodiments described herein, for example, a composition comprising cannabidiol, cannabinodiol, and at least one compound selected from o-methylcannabidiol, o-methylcannabinol, o-propylcannabinol, and o-pentylcannabinol; a composition comprising Δ9-tetrahydrocannabinol, cannabinol, and at least one compound selected from o-methylcannabinol, o-propylcannabinol, and o-pentylcannabinol; a composition comprising cannabinol, Δ9-tetrahydrocannabinol and exo-tetrahydrocannabinol; or a composition comprising cannabinol, Δ9-tetrahydrocannabinol, and Δ10-tetrahydrocannabinol is administered once daily. In some embodiments, the composition is administered twice daily.

In some embodiments, the composition described herein (liquid or solid, or prepared according to the methods described herein) is administered three to five times a day. In some embodiments, the composition is administered every hour, every 2 hours, every 3 hours, every 4 hours, every 5 hours, every 6 hours, every 8 hours, or every 12 hours.

In further embodiments, the plant material comprises one or more cannabinoids.

In some embodiments, the plant material comprises cannabidiol.

In some embodiments, the plant material comprises tetrahydrocannabinol.

In some embodiments, the plant material comprises cannabidiol and tetrahydrocannabinol.

In some embodiments, the compositions comprise cannabidiol, one or more cannabidiol derivatives, tetrahydrocannabinol, and/or tetrahydrocannabinol derivatives.

In further embodiments, the composition comprises cannabidiol and at least one cannabidiol derivative with a retention time, determined from an HPLC trace of the composition, shorter than cannabidiol's retention time, determined from the HPLC trace, and the cannabidiol derivative is present in the composition in an amount which is at least about 2% of the amount of cannabidiol in the composition. In an aspect of these embodiments, shorter refers to up to 3 minutes smaller retention time than the retention time of cannabidiol. In another aspect of these embodiments, shorter refers to up to 2 minutes smaller retention time than the retention time of cannabidiol.

In further embodiments, the composition comprises cannabidiol and at least two cannabidiol derivatives with respective retention times, determined from an HPLC trace of the composition, shorter than cannabidiol's retention time, determined from the HPLC trace, and the cannabidiol derivatives are present in the composition in an amount which is at least about 2% of the amount of cannabidiol in the composition. In an aspect of these embodiments, shorter refers to up to 3 minutes smaller retention time than the retention time of cannabidiol. In another aspect of these embodiments, shorter refers to up to 2 minutes smaller retention time than the retention time of cannabidiol.

In further embodiments, the composition comprises cannabidiol and at least three cannabidiol derivatives with respective retention times, determined from an HPLC trace of the composition, shorter than cannabidiol's retention time, determined from the HPLC trace, and the cannabidiol derivatives are present in the composition in an amount which is at least about 2% of the amount of cannabidiol in the composition. In an aspect of these embodiments, shorter refers to up to 3 minutes smaller retention time than the retention time of cannabidiol. In another aspect of these embodiments, shorter refers to up to 2 minutes smaller retention time than the retention time of cannabidiol.

In further embodiments, the composition comprises cannabidiol and at least one cannabidiol derivative with respective retention time, determined from an HPLC trace of the composition, longer than cannabidiol's retention time, determined from the HPLC trace, and the cannabidiol derivatives are present in the composition in an amount which is at least about 2% of the amount of cannabidiol in the composition. In an aspect of these embodiments, longer refers to up to 3 minutes greater retention time than the retention time of cannabidiol. In another aspect of these embodiments, longer refers to up to 2 minutes greater retention time than the retention time of cannabidiol.

In further embodiments, the composition comprises cannabidiol and at least two cannabidiol derivatives with respective retention times, determined from an HPLC trace of the composition, longer than cannabidiol's retention time, determined from the HPLC trace, and the cannabidiol derivatives are present in the composition in an amount which is at least about 2% of the amount of cannabidiol in the composition. In an aspect of these embodiments, longer refers to up to 3 minutes greater retention time than the retention time of cannabidiol. In another aspect of these embodiments, longer refers to up to 2 minutes greater retention time than the retention time of cannabidiol.

In further embodiments, the composition comprises cannabidiol and (i) at least one cannabidiol derivative with respective retention time, determined from an HPLC trace of the composition, longer than cannabidiol's retention time, determined from the HPLC trace, (ii) at least one cannabidiol derivative with respective retention time, determined from an HPLC trace of the composition, shorter than cannabidiol's retention time, determined from the HPLC trace and the cannabidiol derivatives are present in the composition in an amount which is at least about 2% of the amount of cannabidiol in the composition. In an aspect of these embodiments, longer refers to up to 3 minutes greater retention time than the retention time of cannabidiol, and shorter refers to up to 3 minutes smaller retention time than the retention time of cannabidiol. In another aspect of these embodiments, longer refers to up to 2 minutes greater retention time than the retention time of cannabidiol, and shorter refers to up to 2 minutes smaller retention time than the retention time of cannabidiol.

In further embodiments, the composition comprises cannabidiol and (i) at least one cannabidiol derivatives with respective retention time, determined from an HPLC trace of the composition, longer than cannabidiol's retention time, determined from the HPLC trace, (ii) at least two cannabidiol derivatives with respective retention times, determined from an HPLC trace of the composition, shorter than cannabidiol's retention time, determined from the HPLC trace and the cannabidiol derivatives are present in the composition in an amount which is at least about 2% of the amount of cannabidiol in the composition. In an aspect of these embodiments, longer refers to up to 3 minutes greater retention time than the retention time of cannabidiol, and shorter refers to up to 3 minutes smaller retention time than the retention time of cannabidiol. In another aspect of these embodiments, longer refers to up to 2 minutes greater retention time than the retention time of cannabidiol, and shorter refers to up to 2 minutes smaller retention time than the retention time of cannabidiol.

In further embodiments, the composition comprises cannabidiol and (i) at least two cannabidiol derivatives with respective retention time, determined from an HPLC trace of the composition, longer than cannabidiol's retention time, determined from the HPLC trace, (ii) at least one cannabidiol derivatives with respective retention times, determined from an HPLC trace of the composition, shorter than cannabidiol's retention time, determined from the HPLC trace and the cannabidiol derivatives are present in the composition in an amount which is at least about 2% of the amount of cannabidiol in the composition. In an aspect of these embodiments, longer refers to up to 3 minutes greater retention time than the retention time of cannabidiol, and shorter refers to up to 3 minutes smaller retention time than the retention time of cannabidiol. In another aspect of these embodiments, longer refers to up to 2 minutes greater retention time than the retention time of cannabidiol, and shorter refers to up to 2 minutes smaller retention time than the retention time of cannabidiol.

In further embodiments, the composition comprises cannabidiol and (i) at least two cannabidiol derivatives with respective retention time, determined from an HPLC trace of the composition, longer than cannabidiol's retention time, determined from the HPLC trace, (ii) at least two cannabidiol derivatives with respective retention times, determined from an HPLC trace of the composition, shorter than cannabidiol's retention time, determined from the HPLC trace and the cannabidiol derivatives are present in the composition in an amount which is at least about 2% of the amount of cannabidiol in the composition. In an aspect of these embodiments, longer refers to up to 3 minutes greater retention time than the retention time of cannabidiol, and shorter refers to up to 3 minutes smaller retention time than the retention time of cannabidiol. In another aspect of these embodiments, longer refers to up to 2 minutes greater retention time than the retention time of cannabidiol, and shorter refers to up to 2 minutes smaller retention time than the retention time of cannabidiol.

In further embodiments, the composition comprises cannabidiol and (i) at least two cannabidiol derivatives with respective retention time, determined from an HPLC trace of the composition, longer than cannabidiol's retention time, determined from the HPLC trace, (ii) at least three cannabidiol derivatives with respective retention times, determined from an HPLC trace of the composition, shorter than cannabidiol's retention time, determined from the HPLC trace and the cannabidiol derivatives are present in the composition in an amount which is at least about 2% of the amount of cannabidiol in the composition. In an aspect of these embodiments, longer refers to up to 3 minutes greater retention time than the retention time of cannabidiol, and shorter refers to up to 3 minutes smaller retention time than the retention time of cannabidiol. In another aspect of these embodiments, longer refers to up to 2 minutes greater retention time than the retention time of cannabidiol, and shorter refers to up to 2 minutes smaller retention time than the retention time of cannabidiol.

In aspects of these embodiments, a first cannabidiol derivative is characterized by a relative retention time of about 0.677, about 0.891, about 0.951, about 1.087, or about 1.111.

In aspects of these embodiments, a first cannabidiol derivative is characterized by a relative retention time selected from about 0.677, about 0.891, about 0.951, about 1.087, and about 1.111, and a second cannabidiol derivative is characterized by a relative retention time selected from about 0.677, about 0.891, about 0.951, about 1.087, and about 1.111, the first and second cannabidiol derivatives having different relative retention times.

In aspects of these embodiments, a first cannabidiol derivative is characterized by a relative retention time selected from about 0.677, about 0.891, about 0.951, about 1.087, and about 1.111, a second cannabidiol derivative is characterized by a relative retention time selected from about 0.677, about 0.891, about 0.951, about 1.087, and about 1.111, and a third cannabidiol derivative is characterized by a relative retention time selected from about 0.677, about 0.891, about 0.951, about 1.087, and about 1.111, the first, second and third cannabidiol derivatives having different relative retention times.

In aspects of these embodiments, a first cannabidiol derivative is characterized by a relative retention time selected from about 0.677, about 0.891, about 0.951, about 1.087, and about 1.111, a second cannabidiol derivative is characterized by a relative retention time selected from about 0.677, about 0.891, about 0.951, about 1.087, and about 1.111, a third cannabidiol derivative is characterized by a relative retention time selected from about 0.677, about 0.891, about 0.951, about 1.087, and about 1.111, and a fourth cannabidiol derivative is characterized by a relative retention time selected from about 0.677, about 0.891, about 0.951, about 1.087, and about 1.111, the first, second, third and fourth cannabidiol derivatives having different relative retention times.

In aspects of these embodiments, a first cannabidiol derivative is characterized by a relative retention time selected from about 0.677, about 0.891, about 0.951, about 1.087, and about 1.111, a second cannabidiol derivative is characterized by a relative retention time selected from about 0.677, about 0.891, about 0.951, about 1.087, and about 1.111, a third cannabidiol derivative is characterized by a relative retention time selected from about 0.677, about 0.891, about 0.951, about 1.087, and about 1.111, a fourth cannabidiol derivative is characterized by a relative retention time selected from about 0.677, about 0.891, about 0.951, about 1.087, and about 1.111, and a fifth cannabidiol derivative is characterized by a relative retention time selected from about 0.677, about 0.891, about 0.951, about 1.087, and about 1.111, the first, second, third, fourth and fifth cannabidiol derivatives having different relative retention times.

In further embodiments, each of the cannabidiol derivatives characterized by a relative retention time of about 0.677, about 0.891, about 0.951, about 1.087, or about 1.111, is present in the composition at an amount, independently selected from, of at least about 2%, at least about 3%, at least about 4%, at least about 5%, at least about 2% to about 5%, at least about 3% to about 5%, and at least about 4% to about 5%.

Figure 16:
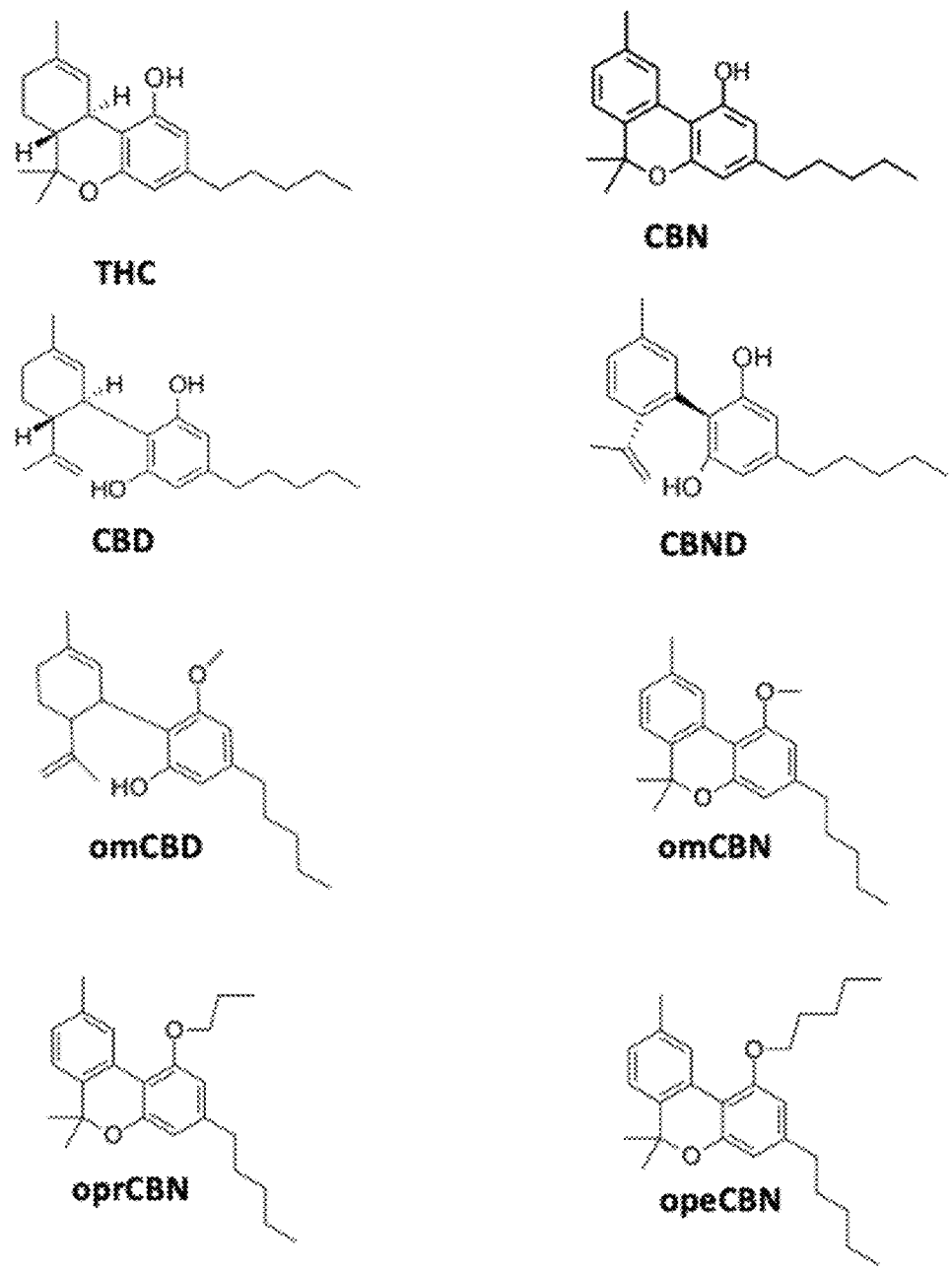
FIG. 16 is a schematic representation of chemical structures of selected cannabinoids.

In some embodiments, a method of any one of the method embodiments disclosed herein can be used to obtain a composition from hemp *Cannabis*. The composition obtained from hemp *Cannabis* comprises cannabidiol (CBD), cannabinodiol (CBND), and at least one compound selected from o-methylcannabidiol, o-methylcannabinol, o-propylcannabinol, and o-pentylcannabinol (FIG. 16). The data in Tables 3 and 4 in Example 8 confirm the presence of CBND (Table 4, lines 46, 49), o-methylcannabidiol (Table 3, line 23), o-methylcannabinol (Table 4, line 18), o-propylcannabinol (Table 4, line 26), and o-pentylcannabinol (Table 4, line 35) in the composition isolated from hemp *Cannabis*. The chemical identity of CBND in the composition was further confirmed by LCMS and $^1$H NMR (see FIG. 12). CBND, o-methylcannabidiol, o-methylcannabinol, o-propylcannabinol, and o-pentylcannabinol are not present in the composition obtained by extraction of hemp *cannabis* biomass using hexane extraction as described in Example 10 (a typical procedure in the art) rather than the thermal treatment described herein. The absence of the components in the hexane extract was confirmed using the same UHPLC-HRMS/MS procedure as disclosed in Example 8. Therefore, the presence of these components is unique to the thermal treatment of hemp *Cannabis* under the conditions of the method embodiments disclosed herein.

In some embodiments, a method of any one of the method embodiments disclosed herein can be used to obtain a composition of compounds from medical *Cannabis*. The composition obtained from medical *Cannabis* comprises cannabinol (CBN), Δ9-tetrahydrocannabinol (Δ9THC), and at least one compound selected from o-methylcannabinol, o-propylcannabinol, and o-pentylcannabinol. o-Methylcannabinol, o-propylcannabinol, and o-pentylcannabinol are formed from CBN under the conditions of the methods described herein. The alkylated o-methylcannabinol, o-propylcannabinol, and o-pentylcannabinol have been identified in the composition obtained from hemp *Cannabis* (see Tables 3 and 4 in Example 8). Since the composition obtained from medical *Cannabis* contains over 20 times more CBN (the precursor of the o-methylcannabinol, o-propylcannabinol, and o-pentylcannabinol) compared to the composition obtained from hemp *Cannabis* (see Table 2, Example 8, and Table 6, Example 9), o-methylcannabinol, o-propylcannabinol, and o-pentylcannabinol are expected to be present in the composition obtained from medical *Cannabis*.

In some embodiments, a method of any one of the method embodiments disclosed herein can be used to obtain a composition of compounds from medical *Cannabis*, comprising cannabinol, Δ9-tetrahydrocannabinol and exo-tetrahydrocannabinol. In some embodiments, a method of any one of the method embodiments disclosed herein can be used to obtain a composition of compounds from medical *Cannabis*, comprising cannabinol, Δ9-tetrahydrocannabinol and Δ10-tetrahydrocannabinol. In some embodiments, a method of any one of the method embodiments disclosed herein can be used to obtain a composition of compounds from medical *Cannabis*, comprising cannabinol, Δ9-tetrahydrocannabinol, exo-tetrahydrocannabinol and Δ10-tetrahydrocannabinol.

Exo-tetrahydrocannabinol has been shown to have potent antibacterial activity. Exo-tetrahydrocannabinol is known to interact with CB1R. In drug discrimination trials, exo-tetrahydrocannabinol performed similarly to THC, but at a lower potency, indicating partial agonist activity. In a more detailed animal study, exo-tetrahydrocannabinol by itself behaved like an agonist and in combination enhanced the Δ9-THC response, modifying it in a species-specific manner. The presence of exo-tetrahydrocannabinol differentiates the therapeutic profile of the compositions described herein in comparison to traditional cannabinoid-containing compositions that are designed to minimize the presence of exo-tetrahydrocannabinol.

Δ10-Tetrahydrocannabinol, also called Δ3-tetrahydrocannabinol is known to interact with CB1R.

The rare cannabinoids such as CBND, o-methylcannabidiol (omCBD), o-methylcannabinol (omCBN), o-propylcannabinol (oprCBN), and o-pentylcannabinol (opeCBN), are known to have pharmacological effects. For example, o-methylcannabidiol has been shown as a selective and potent 15-lipoxygenase (15-LOX) inhibition. Through inhibition of 15-LOX, o-methylcannabidiol prevents formation of oxidized low-density lipoprotein. 15-LOX inhibitors are potential therapeutics for atherosclerosis by reducing LDL oxidation. Further, addition of alkyl substituents to CBN (such as in o-methylcannabinol, o-propylcannabinol, and o-pentylcannabinol) is known to vastly increase its potency at both the CB1 and the CB2 receptors in brain synaptosomal samples and in over-expression model in COS-7 cell lines. These alkylated cannabinoids (e.g., o-methylcannabidiol, o-methylcannabinol, o-propylcannabinol, and o-pentylcannabinol), have increased lipophilicity compared to the parent unalkylated cannabinoids due to the replacement of the polar alcohol group with a non-polar alkoxy substituent. Therefore, these compounds have improved solubility in the plasma membrane, resulting in changes in the membrane fluidity. The membrane provides conformational and/or mechanistic stability to the endocannabinoid system (ECS) targets that are necessary for their activity. There is extensive evidence of specific orientation and stabilization of phospholipids by different cannabinoids depending on molecular structure. This change in membrane fluidity has been directly related to the effects of the cannabinoids, which makes more lipophilic cannabinoids, such as the alkylated CBN and CBD derivatives particularly attractive candidates as pharmaceuticals.

Pharmacological activity of CBND, o-methylcannabidiol, o-methylcannabinol, o-propylcannabinol, and o-pentylcannabinol was further evaluated using molecular docking. Molecular docking is an in silico method that predicts the affinity of a ligand to a protein based upon the total energy of the bound ligand-protein complex. The calculations were performed according to the method described in Example 12. Molecular docking of the cannabinoids with the following receptors and enzymes was assessed.

Cannabinoid Receptor 1 (CB1R). The CB1R is the most abundant of all the G protein-coupled receptors (GPCRs) in the central nervous system and is also expressed in many other tissue types. CB1R plays a critical role in mammalian homeostasis specifically in inflammation and metabolism. The CB1R is a therapeutic target for neurodevelopmental disorders, epilepsy, Parkinson's disease, Huntington's disease, Alzheimer's disease, anxiety, stroke, neuropathic pain, inflammation, hypophagia, insulin regulation, cachexia, and hypertension.

The crystal structure of human CB1R was obtained from RCSB PDB (ID: 5TGZ). The flavodoxin stabilizer was removed along with other stabilizing molecules co-crystallized with the protein. Results from the best pose as determined by 1) ΔG and 2) distance from binding pocket as determined by the "switch" residue that controls the recruitment of G-protein complex W356 (nitrogen atom) were evaluated.

Cannabinoid Receptor 2 (CB2R). The CB2 receptor has a different expression distribution in the body compared to CB1R—it is mainly localized in immune system cells. For this reason, it has been an attractive endocannabinoid target that would avoid negative psychoactive side effects. The CB2R is a therapeutic target for rheumatoid arthritis, autism, multiple sclerosis, atherosclerosis, and inflammatory pain.

The crystal structure of human CB2R was obtained from RCSB PDB (ID: 5ZTY). The endolysin stabilizer was removed along with other stabilizing molecules co-crystallized with the protein. Results from the best pose as determined by 1) ΔG and 2) distance from binding pocket as determined by the "switch" residues W258 (homologous to CB1R) were evaluated.

Monoacylglycerol Lipase (MGL). In an effort to avoid psychoactive effects of cannabinoid receptors, the metabolic enzyme targets 2-arachidonylglycerol (2-AG) and anandamide (arachidonoylethanolamide, AEA) are of interest. MGL is the primary metabolic enzyme of 2-AG and is membrane-proximal in pre-synaptic neurons (same as the receptors). Inhibiting MGL increases 2-AG and has therapeutic potential for inflammation, anxiety and mood disorders, neuropathic pain, Alzheimer's disease, Parkinson's disease, and multiple sclerosis.

The crystal structure of human MGL was obtained from RCSB PDB (ID: 5ZUN). The water molecules and bound ligand were removed from the structure. Results from the best pose as determined by 1) ΔG and 2) distance from binding pocket as determined by the catalytic serine residue S122 were evaluated.

Alpha/Beta Hydrolase Domain 6 (ABHD6). ABHD6 is one of the most recent additions to the endocannabinoid system (ECS) and is a highly promiscuous lipid hydrolase. ABHD6 breaks down between 4-40% of available 2-AG depending on cell/tissue type and is tethered to the membrane on post synaptic neurons. There is some evidence that ABHD6 is localized in the endoplasmic reticulum and regulates AMPA and NMDA receptor subunit assembly. ABHD6 is a therapeutic target for all the same indications as MGL. Additionally, mouse knock out models show ABHD6 is a critical metabolic regulator, completely preventing the onset of diabetes and obesity.

A homology model of human ABHD6 was generated using YASARA's "hm_build" macro; briefly, the template protein most homologous to ABHD6 (structural genomics putative lipase PDB: 4OPM) was used to generate 25 models, the model with the best overall Z-score was hybridized with the other 24 models to give one final model. The model was evaluated using PROCHECK and 98.9% of residues were within the allowable range of phi-psy dihedral angle. Results from the best pose as determined by 1) ΔG and 2) distance from binding pocket as determined by the catalytic serine residue S148 (oxygen atom) were evaluated.

The results of the molecular docking studies for CBND, o-methylcannabidiol (omCBD), o-methylcannabinol (omCBN), o-propylcannabinol (oprCBN), and o-pentylcannabinol (opeCBN) are summarized below:

| Ligand | CB1R | CB2R | MGL | ABHD6 |
|---|---|---|---|---|
| omCBD | Neutral antagonist | Neutral antagonist | Active | Active |
| CBND | Agonist | Neutral antagonist | Active | Active |
| omCBN | Partial agonist | Neutral antagonist | Active | Active |
| oprCBN | Neutral antagonist | — | Active | Active |
| opeCBN | Neutral antagonist | — | Active | Active |

The obtained data for the receptors and enzymes demonstrates the pharmacological effects of the rare cannabinoids.

CB1R.

CBD is known to show neutral antagonist activity at nanomolar concentrations, blocking endogenous ligand (2-AG) interaction without favoring either activated or inactivated state of the receptor. omCBD, oprCBN, and opeCBN docked with a higher stability (greater $\Delta G$) than CBD, indicative of higher binding affinity, in the same binding region outside the active binding site. Presence of these compounds may stabilize the outer domains, modifying helical coupling in a comparable manner to CBD, but with greater binding affinity and increased potency.

CB2R.

THC is known to exhibit partial agonist activity at nanomolar concentrations, and CBD is known to show neutral antagonist activity at nanomolar concentrations. CBND and omCBN both docked in a conformation more similar to CBD than THC with the lipophilic pentyl group facing toward the "toggle switch" residues, which makes these cannabinoids more likely to display neutral antagonist activity. CBND and omCBN both bind with slightly less stability (smaller $\Delta G$) than CBD, but greater stability compared to THC. They will likely have nanomolar potency.

omCBD is likely to bind at nanomolar concentrations, however, its binding pose was further outside the pocket than any known pharmacological interactions. As its structure is similar to CBD, the most reasonable assumption would be that omCBD exhibits neutral antagonist activity.

MGL.

omCBD, omCBN, oprCBN, and opeCBN all docked with MGL with high stability very close to the active serine residue and are, therefore, likely inhibitors of the enzyme.

CBND docked further out of the active site but is positioned along the access site of the lid domain and the membrane. Mutational analysis of chimeric MGL-ABHD6 proteins with swapped lid domains indicates the lid domain determines binding pocket size and regulates substrate specificity. Even though CBND is positioned further away from the active site, it is still likely to block access of the endogenous ligand and act as an inhibitor with high potency.

ABHD6.

omCBN docked with greater stability (larger $\Delta G$) than 2-AG, the endogenous ligand, and in very close proximity to the active site. It is highly likely to be a potent inhibitor.

CBND and oprCBN both docked with slightly greater stability than THC or CBD in close proximity to the active site and are likely to inhibit ABHD6.

opeCBN docked with greater stability than 2-AG, but in a position further away from the active site. However, the docking pose is located in the pore between the lid-domain and blocks access of 2-AG to the active site; therefore, opeCBN is likely to be a potent inhibitor.

Additionally, rare cannabinoids and other components of the compositions obtained by method of any one of the method embodiments disclosed herein contribute to the "entourage effect", which is known to produce unique therapeutic profiles that are not accessible with purified THC or CBD. The entourage effect is ascribed to the synergistic activities of phytocannabinoids and terpenes present in *Cannabis*. The term was first used to describe synergies observed with the endogenous cannabinoids 2-AG, AEA, and their linoleoyl, palmitoyl, and oleoyl homologs; it was later ascribed to *Cannabis* when similar synergies between secondary metabolites were observed. The rare cannabinoids present in the hemp and medical extracts contribute to the overall therapeutic effect and potency of the formulation. The inclusion of rare cannabinoids that are not present in traditional extractions has been demonstrated to reduce minimum therapeutic dose threshold, reduce negative side effects, and modify overall therapeutic effects profiles in comparison to other orally administered *Cannabis* products made with traditional extraction methods. Examples 17 and 20 show that oral ingestion and smoking of hemp *Cannabis* distillate provides stronger and longer lasting positive effects compared to consumption of pure CBD isolate at the same or higher dose. Specifically, Example 20 demonstrates that orally ingested CBD isolate is at least 10 times less potent compared to the orally ingested hemp *Cannabis* distillate. These observations are in agreement with the expected entourage effect from the synergy of cannabinoids such as CBD, CBN, $\Delta$9-THC, rare cannabinoids present in hemp *Cannabis* distillate.

In some embodiments, the present disclosure relates to a composition prepared by a method according to the embodiments described herein, comprising cannabidiol, cannabinodiol, and at least one compound selected from o-methylcannabidiol, o-methylcannabinol, o-propylcannabinol, and o-pentylcannabinol. In some embodiments, the composition comprises from about 10 wt. % to about 70 wt. % cannabidiol and from about 1 wt. % to about 20 wt. % cannabinodiol. For example, the composition can independently comprise from about 15 wt. % to about 65 wt. %, from about 20 wt. % to about 60 wt. %, from about 25 wt. % to about 55 wt. %, from about 30 wt. % to about 50 wt. %, or from about 35 wt. % to about 45 wt. % of cannabidiol, and from about 2 wt. % to about 19 wt. %, from about 3 wt. % to about 18 wt. %, from about 4 wt. % to about 17 wt. %, from about 5 wt. % to about 16 wt. %, from about 6 wt. % to about 15 wt. %, from about 7 wt. % to about 14 wt. %, from about 8 wt. % to about 13 wt. %, or from about 9 wt. % to about 12 wt. % of cannabinodiol.

In some embodiments, the composition comprises from about 20 wt. % to about 60 wt. % cannabidiol and from about 1 wt. % to about 5 wt. % cannabinodiol. For example, the composition can independently comprise from about 25 wt. % to about 55 wt. %, from about 30 wt. % to about 50 wt. %, or from about 35 wt. % to about 45 wt. % cannabidiol, and from about 1 wt. % to about 2 wt. %, from about 1.5 wt. % to about 3 wt. %, or from about 1 wt. % to about 3.5 wt. % cannabinodiol.

In some embodiments, the composition comprises about 22 wt. % cannabidiol. In some embodiments, the composition comprises about 56 wt. % cannabidiol. In some embodiments, the composition comprises about 25 wt. %, about 30 wt. %, about 35 wt. %, about 40 wt. %, about 45 wt. % about 50 wt. %, about 55 wt. %, about 60 wt. %, about 65 wt. %, about 70 wt. %, about 75 wt. %, or about 80 wt. % cannabidiol.

In some embodiments, the composition comprises about 1 wt. %, about 2 wt. %, about 3 wt. %, about 4 wt. %, about 5 wt. %, about 6 wt. %, about 7 wt. %, about 8 wt. %, about 9 wt. %, or about 10 wt. % cannabinodiol.

In some embodiments, the composition comprises at least 50 wt. % cannabidiol and at least 3 wt. % cannabinodiol. For example, the composition independently comprises at least 55 wt. %, at least 60 wt. %, at least 65 wt. %, at least 70 wt. %, or at least 75 wt. % cannabidiol, and at least 3 wt. %, at least 3.5 wt. %, at least 4 wt. %, at least 4.5 wt. %, at least 5 wt. %, at least 5.5 wt. %, at least 6 wt. %, at least 7 wt. %, at least 8 wt. %, at least 9 wt. %, or at least 10 wt. % cannabinodiol.

In some embodiments, the composition comprises at least 20 wt. % cannabidiol and at least 1 wt. % cannabinodiol. For example, the composition independently comprises at least 25 wt. %, at least 30 wt. %, at least 35 wt. %, at least 40 wt. %, or at least 45 wt. % cannabidiol, and at least 1.5 wt. %, at least 2 wt. %, or at least 2.5 wt. % cannabinodiol.

In some embodiments, the present disclosure relates a composition prepared by a method according to the embodiments described herein, comprising Δ9-tetrahydrocannabinol, cannabinol, and at least one compound selected from o-methylcannabinol, o-propylcannabinol, and o-pentylcannabinol.

In some embodiments, the composition comprises from about 1.0 wt. % to about 15 wt. % Δ9-tetrahydrocannabinol and from about 5 wt. % to about 50 wt. % cannabinol. For example, the composition can independently comprise from about 2 wt. % to about 14 wt. %, from about 3 wt. % to about 13 wt. %, from about 4 wt. % to about 12 wt. %, from about 5 wt. % to about 11 wt. %, from about 6 wt. % to about 10 wt. %, or from about 7 wt. % to about 9 wt. % Δ9-tetrahydrocannabinol, and from about 7.5 wt. % to about 45 wt. %, from about 10 wt. % to about 40 wt. %, from about 15 wt. % to about 35 wt. %, or from about 20 wt. % to about 30 wt. % cannabinol.

In some embodiments, the composition comprises from about 5 wt. % to about 10 wt. % Δ9-tetrahydrocannabinol and from about 5 wt. % to about 30 wt. % cannabinol. For example, the composition can independently comprise from about 5.5 wt. % to about 9.5 wt. %, from about 6 wt. % to about 9 wt. %, or from about 7 wt. % to about 8 wt. % Δ9-tetrahydrocannabinol, and from about 7.5 wt. % to about 25 wt. %, from about 10 wt. % to about 20 wt. %, or from about 12.5 wt. % to about 15 wt. % cannabinol.

In some embodiments, the composition comprises about 10 wt. % Δ9-tetrahydrocannabinol. In some embodiments, the composition comprises about 6 wt. % Δ9-tetrahydrocannabinol. In some embodiments, the composition comprises about 5 wt. %, about 6 wt. %, about 7 wt. %, about 8 wt. %, about 9 wt. % about 10 wt. %, about 11 wt. %, about 12 wt. %, about 13 wt. %, about 14 wt. %, about 15 wt. %, about 16 wt. %, about 17 wt. %, about 18 wt. %, about 19 wt. %, or about 20 wt. % Δ9-tetrahydrocannabinol.

In some embodiments, the composition comprises about 19 wt. % cannabinol. In some embodiments, the composition comprises about 28 wt. % cannabinol. In some embodiments, the composition comprises about 15 wt. %, about 17 wt. %, about 19 wt. %, about 22 wt. %, about 24 wt. % about 26 wt. %, about 28 wt. %, about 30 wt. %, about 32 wt. %, about 34 wt. %, about 36 wt. %, about 38 wt. %, about 40 wt. %, about 45 wt. %, or about 50 wt. % cannabinol.

In some embodiments, the composition comprises at least 1 wt. % Δ9-tetrahydrocannabinol and at least 20 wt. % cannabinol. For example, the composition independently comprises at least 2 wt. %, at least 3 wt. %, at least 4 wt. %, at least 5 wt. %, at least 6 wt. %, at least 7 wt. %, at least 8 wt. %, at least 9 wt. %, at least 10 wt. %, at least 11 wt. %, at least 12 wt. %, at least 13 wt. %, at least 14 wt. %, at least 15 wt. %, at least 16 wt. %, at least 17 wt. %, at least 18 wt. %, at least 19 wt. %, or at least 20 wt. % Δ9-tetrahydrocannabinol, and at least 25 wt. %, at least 30 wt. %, at least 35 wt. %, at least 40 wt. %, at least 45 wt. %, or at least 50 wt. % cannabinol.

In some embodiments, the composition comprises at least 0.1 wt. % Δ9-tetrahydrocannabinol and at least 10 wt. % cannabinol. For example, the composition independently comprises at least 0.2 wt. %, at least 0.3 wt. %, at least 0.4 wt. %, at least 0.5 wt. %, at least 0.6 wt. %, at least 0.7 wt. %, at least 0.8 wt. %, or at least 0.9 wt. % Δ9-tetrahydrocannabinol, and at least 11 wt. %, at least 12 wt. %, at least 13 wt. %, at least 14 wt. %, at least 15 wt. %, at least 16 wt. %, at least 17 wt. %, at least 18 wt. %, or at least 19 wt. % cannabinol.

In some embodiments, the present disclosure relates to a liquid or solid composition comprising cannabidiol, cannabinodiol, and at least one compound selected from o-methylcannabidiol, o-methylcannabinol, o-propylcannabinol, and o-pentylcannabinol.

In some embodiments, the liquid or solid composition comprises from about 10 wt. % to about 70 wt. % cannabidiol and from about 1 wt. % to about 20 wt. % cannabinodiol. For example, the liquid or solid composition can independently comprise from about 15 wt. % to about 65 wt. %, from about 20 wt. % to about 60 wt. %, from about 25 wt. % to about 55 wt. % from about 30 wt. % to about 50 wt. % or from about 35 wt. % to about 45 wt. % of cannabidiol, and from about 2 wt. % to about 19 wt. %, from about 3 wt. % to about 18 wt. %, from about 4 wt. % to about 17 wt. %, from about 5 wt. % to about 16 wt. %, from about 6 wt. % to about 15 wt. %, from about 7 wt. % to about 14 wt. %, from about 8 wt. % to about 13 wt. %, or from about 9 wt. % to about 12 wt. % cannabinodiol.

In some embodiments, the liquid or solid composition comprises from about 20 wt. % to about 60 wt. % cannabidiol and from about 1 wt. % to about 5 wt. % cannabinodiol. For example, the liquid or solid composition can independently comprise from about 25 wt. % to about 55 wt. %, from about 30 wt. % to about 50 wt. %, or from about 35 wt. % to about 45 wt. % of cannabidiol, and from about 1 wt. % to about 2 wt. %, from about 1.5 wt. % to about 3 wt. %, or from about 1 wt. % to about 3.5 wt. % cannabinodiol.

In some embodiments, the liquid or solid composition comprises about 22 wt. % cannabidiol. In some embodiments, the liquid or solid composition comprises about 56 wt. % cannabidiol. In some embodiments, liquid or solid composition comprises about 25 wt. %, about 30 wt. %, about 35 wt. %, about 40 wt. %, about 45 wt. %, about 50 wt. %, about 55 wt. % about 60 wt. %, about 65%, about 70%, about 75%, or about 80 wt. % cannabidiol.

In some embodiments, the liquid or solid composition comprises about 1 wt. %, about 2 wt. %, about 3 wt. %, about 4 wt. %, about 5 wt. %, about 6 wt. %, about 7 wt. %, about 8 wt. %, about 9 wt. %, or about 10 wt. % cannabinodiol.

In some embodiments, the liquid or solid composition comprises at least 50 wt. % cannabidiol and at least 3 wt. % cannabinodiol. For example, the liquid or solid composition independently comprises at least 55 wt. %, at least 60 wt. %, at least 65 wt. %, at least 70 wt. %, or at least 75 wt. % cannabidiol, and at least 3 wt. %, at least 3.5 wt. %, at least 4 wt. %, at least 4.5 wt. %, at least 5 wt. %, at least 5.5 wt. %, at least 6 wt. %, at least 7 wt. %, at least 8 wt. %, at least 9 wt. %, or at least 10 wt. % cannabinodiol.

In some embodiments, the liquid or solid composition comprises at least 20 wt. % cannabidiol and at least 1 wt. % cannabinodiol. For example, the liquid or solid composition independently comprises at least 25 wt. %, at least 30 wt. %, at least 35 wt. %, at least 40 wt. %, or at least 45 wt. % cannabidiol, and at least 1.5 wt. %, at least 2 wt. %, or at least 2.5 wt. % cannabinodiol.

In some embodiments, the present disclosure relates to a liquid or solid composition, comprising Δ9-tetrahydrocannabinol, cannabinol, and at least one compound selected from o-methylcannabinol, o-propylcannabinol, and o-pentylcannabinol.

In some embodiments, the liquid or solid composition comprises from about 1.0 wt. % to about 15 wt. % Δ9-tetrahydrocannabinol and from about 5 wt. % to about 50 wt. % cannabinol. For example, the liquid or solid composition can independently comprise from about 2 wt. % to about 14 wt. %, from about 3 wt. % to about 13 wt. %, from about 4 wt. % to about 12 wt. %, from about 5 wt. % to about 11 wt. %, from about 6 wt. % to about 10 wt. %, or from about 7 wt. % to about 9 wt. % Δ9-tetrahydrocannabinol, and from about 7.5 wt. % to about 45 wt. %, from about 10 wt. % to about 40 wt. %, from about 15 wt. % to about 35 wt. % or from about 20 wt. % to about 30 wt. % cannabinol.

In some embodiments, the liquid or solid composition comprises from about 5 wt. % to about 10 wt. % Δ9-tetrahydrocannabinol and from about 5 wt. % to about 30 wt. % cannabinol. For example, the liquid or solid composition can independently comprise from about 5.5 wt. % to about 9.5 wt. %, from about 6 wt. % to about 9 wt. %, or from about 7 wt. % to about 8 wt. % Δ9-tetrahydrocannabinol, and from about 7.5 wt. % to about 25 wt. %, from about 10 wt. % to about 20 wt. %, or from about 12.5 wt. % to about 15 wt. % cannabinol.

In some embodiments, the liquid or solid composition comprises about 10 wt. % Δ9-tetrahydrocannabinol. In some embodiments, the liquid or solid composition comprises about 6 wt. % Δ9-tetrahydrocannabinol. In some embodiments, the liquid or solid composition comprises about 5 wt. %, about 6 wt. %, about 7 wt. %, about 8 wt. %, about 9 wt. % about 10 wt. %, about 11 wt. % about 12 wt. %, about 13 wt. %, about 14 wt. %, about 15 wt. %, about 16 wt. %, about 17 wt. %, about 18 wt. %, about 19 wt. %, or about 20 wt. % Δ9-tetrahydrocannabinol.

In some embodiments, the liquid or solid composition comprises about 19 wt. % cannabinol. In some embodiments, the liquid or solid composition comprises about 28 wt. % cannabinol. In some embodiments, the liquid or solid composition comprises about 15 wt. %, about 17 wt. %, about 19 wt. %, about 22 wt. %, about 24 wt. %, about 26 wt. %, about 28 wt. % about 30 wt. %, about 32 wt. %, about 34 wt. %, about 36 wt. %, about 38 wt. %, about 40 wt. %, about 45 wt. %, or about 50 wt. % cannabinol.

In some embodiments, the liquid or solid composition comprises at least 1 wt. % Δ9-tetrahydrocannabinol and at least 20 wt. % cannabinol. For example, the liquid or solid composition independently comprises at least 2 wt. %, at least 3 wt. %, at least 4 wt. %, at least 5 wt. %, at least 6 wt. %, at least 7 wt. %, at least 8 wt. %, at least 9 wt. %, at least 10 wt. %, at least 11 wt. %, at least 12 wt. %, at least 13 wt. %, at least 14 wt. %, at least 15 wt. %, at least 16 wt. %, at least 17 wt. %, at least 18 wt. %, at least 19 wt. %, or at least 20 wt. % Δ9-tetrahydrocannabinol, and at least 25 wt. %, at least 30 wt. %, at least 35 wt. %, at least 40 wt. %, at least 45 wt. %, or at least 50 wt. % cannabinol.

In some embodiments, the liquid or solid composition comprises at least 0.1 wt. % Δ9-tetrahydrocannabinol and at least 10 wt. % cannabinol. For example, the liquid or solid composition independently comprises at least 0.2 wt. %, at least 0.3 wt. %, at least 0.4 wt. %, at least 0.5 wt. %, at least 0.6 wt. %, at least 0.7 wt. %, at least 0.8 wt. %, or at least 0.9 wt. % Δ9-tetrahydrocannabinol, and at least 11 wt. %, at least 12 wt. %, at least 13 wt. %, at least 14 wt. %, at least 15 wt. %, at least 16 wt. %, at least 17 wt. %, at least 18 wt. %, or at least 19 wt. % cannabinol.

In some embodiments, the at least one compound selected from o-methylcannabidiol, o-methylcannabinol, o-propylcannabinol, and o-pentylcannabinol is present in an amount from about 0.05 wt. % to about 1 wt. %. For example, the at least one compound selected from o-methylcannabidiol, o-methylcannabinol, o-propylcannabinol, and o-pentylcannabinol is present in an amount from about 0.1 wt. % to about 0.9 wt. %, from about 0.2 wt. % to about 0.8 wt. %, from about 0.3 wt. % to about 0.7 wt. %, or from about 0.4 wt. % to about 0.6 wt. %.

In some embodiments, the at least one compound selected from o-methylcannabidiol, o-methylcannabinol, o-propylcannabinol, and o-pentylcannabinol is present in an amount from 0.1 wt. % to 0.5 wt. %. For example, the at least one compound selected from o-methylcannabidiol, o-methylcannabinol, o-propylcannabinol, and o-pentylcannabinol is present in an amount from about 0.15 wt. % to about 0.45 wt. %, from about 0.2 wt. % to about 0.4 wt. %, or from about 0.25 wt. % to about 0.35 wt. %.

In some embodiments, the at least one compound selected from, o-methylcannabinol, o-propylcannabinol, and o-pentylcannabinol is present in an amount from about 0.05 wt. % to about 1 wt. %. For example, the at least one compound selected from, o-methylcannabinol, o-propylcannabinol, and o-pentylcannabinol is present in an amount from about 0.1 wt. % to about 0.9 wt. %, from about 0.2 wt. % to about 0.8 wt. %, from about 0.3 wt. % to about 0.7 wt. %, or from about 0.4 wt. % to about 0.6 wt. %.

In some embodiments, the at least one compound selected from o-methylcannabinol, o-propylcannabinol, and o-pentylcannabinol is present in an amount from 0.1 wt. % to 0.5 wt. %.

For example, the at least one compound selected from o-methylcannabinol, o-propylcannabinol, and o-pentylcannabinol is present in an amount from about 0.15 wt. % to about 0.45 wt. %, from about 0.2 wt. % to about 0.4 wt. %, or from about 0.25 wt. % to about 0.35 wt. %.

In some embodiments, the present disclosure relates to a liquid or solid composition, comprising cannabinol, Δ9-tetrahydrocannabinol and exo-tetrahydrocannabinol, wherein the cannabinol is present in the composition from about 5 wt. % to about 50 wt. %, the Δ9-tetrahydrocannabinol is present in the composition from about 1 wt. % to about 15 wt. %, and the exo-tetrahydrocannabinol is present in the composition from about 1 wt. % to about 5 wt. %. For example, the liquid or solid composition can independently comprise from about 2 wt. % to about 14 wt. %, from about 3 wt. % to about 13 wt. %, from about 4 wt. % to about 12 wt. %, from about 5 wt. % to about 11 wt. %, from about 6 wt. % to about 10 wt. %, or from about 7 wt. % to about 9 wt. % Δ9-tetrahydrocannabinol; from about 7.5 wt. % to about 45 wt. %, from about 10 wt. % to about 40 wt. %, from about 15 wt. % to about 35 wt. %, or from about 20 wt. % to about 30 wt. % cannabinol; and from about 1 wt. % to about 5 wt. %, from about 1.5 wt. % to about 4.5 wt. %, from about 2 wt. % to about 4 wt. %, or from about 2.5 wt. % to about 3.5 wt. % of exo-tetrahydrocannabinol.

In some embodiments, the cannabinol is present in the composition from about 5 wt. % to about 30 wt. %, the Δ9-tetrahydrocannabinol is present in the composition from about 5 wt. % to about 10 wt. %, and the exo-tetrahydrocannabinol is present in the composition from about 1.5 wt. % to about 3 wt. %. For example, the liquid or solid composition can independently comprise from about 5.5 wt. % to about 9.5 wt. %, from about 6 wt. % to about 9 wt. %, or from about 7 wt. % to about 8 wt. % Δ9-tetrahydrocannabinol; from about 7.5 wt. % to about 25 wt. %, from about 10 wt. % to about 20 wt. %, or from about 12.5 wt. % to about 15 wt. % cannabinol; and from about 1.7 wt. % to about 2.8 wt. %, from about 1.9 wt. % to about 2.6 wt. %, or from about 2.1 wt. % to about 2.4 wt. % exo-tetrahydrocannabinol.

In some embodiments, the liquid or solid composition comprises about 10 wt. % Δ9-tetrahydrocannabinol. In some embodiments, the liquid or solid composition comprises about 6 wt. % Δ9-tetrahydrocannabinol. In some embodiments, the liquid or solid composition comprises about 5 wt. %, about 6 wt. %, about 7 wt. %, about 8 wt. %, about 9 wt. % about 10 wt. %, about 11 wt. % about 12 wt. %, about 13 wt. %, about 14 wt. %, about 15 wt. %, about 16 wt. %, about 17 wt. %, about 18 wt. %, about 19 wt. %, or about 20 wt. % Δ9-tetrahydrocannabinol.

In some embodiments, the liquid or solid composition comprises about 19 wt. % cannabinol. In some embodiments, the liquid or solid composition comprises about 28 wt. % cannabinol. In some embodiments, the liquid or solid composition comprises about 15 wt. %, about 17 wt. %, about 19 wt. %, about 22 wt. %, about 24 wt. %, about 26 wt. %, about 28 wt. % about 30 wt. %, about 32 wt. %, about 34 wt. %, about 36 wt. %, about 38 wt. %, about 40 wt. %, about 45 wt. %, or about 50 wt. % cannabinol.

In some embodiments, the liquid or solid composition comprises about 2.3 wt. % exo-tetrahydrocannabinol. In some embodiments, the liquid or solid composition comprises about 1.0 wt. %, about 1.2 wt. %, about 1.4 wt. %, about 1.6 wt. %, about 1.8 wt. % about 2.0 wt. % about 2.2 wt. % about 2.4 wt. %, about 2.6 wt. %, about 2.8 wt. %, about 3.0 wt. %, about 3.2 wt. %, about 3.4 wt. % about 3.6 wt. % about 3.8 wt. %, about 4.0 wt. %, about 4.2 wt. %, about 4.4 wt. % about 4.6 wt. % about 4.8 wt. %, or about 5.0 wt. % exo-tetrahydrocannabinol.

In some embodiments, the present disclosure relates to a liquid or solid composition, comprising cannabinol, Δ9-tetrahydrocannabinol, and Δ10-tetrahydrocannabinol, wherein the cannabinol is present in the composition from about 5 wt. % to about 50 wt. %, the Δ9-tetrahydrocannabinol is present in the composition from about 1 wt. % to about 15 wt. %, and the Δ10-tetrahydrocannabinol is present in the composition from about 1 wt. % to about 5 wt. %. For example, the liquid or solid composition can independently comprise from about 2 wt. % to about 14 wt. %, from about 3 wt. % to about 13 wt. %, from about 4 wt. % to about 12 wt. %, from about 5 wt. % to about 11 wt. %, from about 6 wt. % to about 10 wt. %, or from about 7 wt. % to about 9 wt. % Δ9-tetrahydrocannabinol; from about 7.5 wt. % to about 45 wt. %, from about 10 wt. % to about 40 wt. %, from about 15 wt. % to about 35 wt. % or from about 20 wt. % to about 30 wt. % cannabinol; and from about 1 wt. % to about 5 wt. %, from about 1.5 wt. % to about 4.5 wt. %, from about 2 wt. % to about 4 wt. %, or from about 2.5 wt. % to about 3.5 wt. % of Δ10-tetrahydrocannabinol.

In some embodiments, the cannabinol is present in the composition from about 5 wt. % to about 30 wt. %, the Δ9-tetrahydrocannabinol is present in the composition from about 5 wt. % to about 10 wt. %, and the Δ10-tetrahydrocannabinol is present in the composition from about 2 wt. % to about 4 wt. %. For example, the liquid or solid composition can independently comprise from about 5.5 wt. % to about 9.5 wt. %, from about 6 wt. % to about 9 wt. %, or from about 7 wt. % to about 8 wt. % Δ9-tetrahydrocannabinol; from about 7.5 wt. % to about 25 wt. %, from about 10 wt. % to about 20 wt. %, or from about 12.5 wt. % to about 15 wt. % cannabinol; and from about 2.2 wt. % to about 3.8 wt. %, from about 2.4 wt. % to about 3.6 wt. %, from about 2.6 wt. % to about 3.4 wt. %, or from about 2.8 wt. % to about 3.2 wt. % of Δ10-tetrahydrocannabinol.

In some embodiments, the liquid or solid composition comprises about 10 wt. % Δ9-tetrahydrocannabinol. In some embodiments, the liquid or solid composition comprises about 6 wt. % Δ9-tetrahydrocannabinol. In some embodiments, the liquid or solid composition comprises about 5 wt. %, about 6 wt. %, about 7 wt. %, about 8 wt. %, about 9 wt. % about 10 wt. %, about 11 wt. % about 12 wt. %, about 13 wt. %, about 14 wt. %, about 15 wt. %, about 16 wt. %, about 17 wt. %, about 18 wt. %, about 19 wt. %, or about 20 wt. % Δ9-tetrahydrocannabinol.

In some embodiments, the liquid or solid composition comprises about 19 wt. % cannabinol. In some embodiments, the liquid or solid composition comprises about 28 wt. % cannabinol. In some embodiments, the liquid or solid composition comprises about 15 wt. %, about 17 wt. %, about 19 wt. %, about 22 wt. %, about 24 wt. %, about 26 wt. %, about 28 wt. % about 30 wt. %, about 32 wt. %, about 34 wt. %, about 36 wt. %, about 38 wt. %, about 40 wt. %, about 45 wt. %, or about 50 wt. % cannabinol.

In some embodiments, the liquid or solid composition comprises about 3 wt. % Δ10-tetrahydrocannabinol. In some embodiments, the liquid or solid composition comprises about 1.0 wt. %, about 1.2 wt. %, about 1.4 wt. %, about 1.6 wt. %, about 1.8 wt. % about 2.0 wt. % about 2.2 wt. % about 2.4 wt. %, about 2.6 wt. %, about 2.8 wt. %, about 3.0 wt. %, about 3.2 wt. %, about 3.4 wt. % about 3.6 wt. % about 3.8 wt. %, about 4.0 wt. %, about 4.2 wt. %, about 4.4 wt. % about 4.6 wt. % about 4.8 wt. %, or about 5.0 wt. % Δ10-tetrahydrocannabinol.

In some embodiments, the present disclosure relates to a liquid or solid composition, comprising cannabinol, Δ9-tetrahydrocannabinol, exo-tetrahydrocannabinol and Δ10-tetrahydrocannabinol, wherein the percentages present in the composition are the same as described about for liquid or solid compositions containing cannabinol, Δ9-tetrahydrocannabinol and only one of exo-tetrahydrocannabinol and Δ10-tetrahydrocannabinol.

In some embodiments, the composition further comprises a diluent. Suitable diluents include oils. In some instances, the diluent (e.g., oil) can increase the bioavailability of compounds and compositions prepared by the method embodiments described herein. Examples of diluents include, but are not limited to, olive oil, fractionated coconut MCT (medium chain triglycerides) oil, avocado oil, hemp seed oil, and other similar oils.

The present disclosure relates in part to a method of obtaining compounds from plant or fungus material by thermally treating the plant or fungus material, for example, by heating the plant or fungus material, which results in the formation of volatile compounds in a form of gaseous composition.

The plant or fungus material can be heated by pyrolysis. Pyrolysis is a process of heating a material at elevated temperature, typically in the absence of oxygen, such as under vacuum or under inert atmosphere, to decompose organic materials therein. Generally, a plant or fungus material is heated in a low oxygen or oxygen-free environment (such as partial vacuum or inert atmosphere) to a desired temperature (typically sufficient to release and/or form various gaseous volatile pyrolysis products). For exemplary means by which pyrolysis can be conducted and exemplary conditions for pyrolysis, see for example, U.S. Pat. No. 4,596,259 and US Pat. Appl. Publ. No. 2011/034712, which are incorporated herein by reference in their entirety.

The plant or fungus material can be heated in the presence of oxygen, for example, in the presence of air. For example, the plant or fungus material is heated in an enclosure which has a gas intake opening, which allows air or other oxygen-containing gas mixture to flow into the enclosure, and a gas outlet, connected through the rest of the apparatus to a vacuum source. Alternatively, the plant or fungus material is heated in a sealed enclosure in the presence of air. The plant or fungus material can be heated under atmospheric pressure, partial vacuum, or pressure higher than atmospheric pressure. The plant or fungus material can be heated to or exposed to a temperature from about 50° C. to about 1000° C., for example, to a temperature from about 70° C. to about 800° C., to a temperature from about 90° C. to about 700° C., to a temperature from about 120° C. to about 600° C., or to a temperature from about 200° C. to about 500° C. For example, the plant or fungus material can be heated to or exposed to about 50° C., about 60° C., about 70° C., about 80° C., about 90° C., about 100° C., about 110° C., about 120° C., about 130° C., about 140° C., about 150° C., about 160° C., about 170° C., about 180° C., about 190° C., about 200° C., about 210° C., about 220° C., about 230° C., about 240° C., about 250° C., about 260° C., about 270° C., about 280° C., about 290° C., about 300° C., about 310° C., about 320° C., about 330° C., about 340° C., about 350° C., about 360° C., about 370° C., about 380° C., about 390° C., about 400° C., about 410° C., about 420° C., about 430° C., about 440° C., about 450° C., about 460° C., about 470° C., about 480° C., about 490° C., about 500° C., about 510° C., about 520° C., about 530° C., about 540° C., about 550° C., about 560° C., about 570° C., about 580° C., about 590° C., about 600° C., about 650° C., about 700° C., about 750° C., about 800° C., about 850° C., about 900° C., about 950° C., or about 1000° C.

The plant or fungus material can be heated from a period of time from about 1 minute to about 10 hours. In some embodiments, the plant or fungus material is heated for 1 minute, for 2 minutes, for 3 minutes, for 4 minutes, for 5 minutes, for 6 minutes, for 7 minutes, for 8 minutes, for 9 minutes, for 10 minutes, for 11 minutes, for 12 minutes, for 13 minutes, for 14 minutes, for 15 minutes, for 16 minutes, for 17 minutes, for 18 minutes, for 19 minutes, for 20 minutes, for 25 minutes, for 30 minutes, for 35 minutes, for 40 minutes, for 45 minutes, for 50 minutes, for 55 minutes, for 1 hours, for 1.25 hours, for 1.5 hours, 1.75 hours, for 2 hours, for 2.25 hours, for 2.5 hours, for 2.75 hours, for 3 hours, for 3.25 hours, for 3.5 hours, for 3.75 hours, for 4 hours, for 4.25 hours, for 4.5 hours, for 4.75 hours, for 5 hours, for 5.5 hours, for 6 hours, for 6.5 hours, for 7 hours, for 8 hours, for 8.5 hours, for 9 hours, for 9.5 hours, or for 10 hours.

The plant or fungus material can be heated under a reduced pressure, for example, the enclosure can be under a reduced pressure. For example, the plant or fungus material can be heated under pressure from about 0.1 Torr to about 250 Torr. In some embodiments, the plant or fungus material is heated under a reduced pressure of about 0.1 Torr, about 0.2 Torr, 0.3 Torr, about 0.5 Torr, about 0.6 Torr, about 0.7 Torr, about 0.8 Torr, about 0.9 Torr, about 1 Torr, about 5 Torr, about 10 Torr, about 20 Torr, about 30 Torr, about 40 Torr, about 50 Torr, about 60 Torr, about 70 Torr, about 80 Torr, about 90 Torr, about 100 Torr, about 110 Torr, about 120 Torr, about 130 Torr, about 140 Torr, about 150 Torr, about 160 Torr, about 170 Torr, about 180 Torr, about 190 Torr, about 200 Torr, about 210 Torr, about 220 Torr, about 230 Torr, about 240 Torr, or about 250 Torr.

The enclosure can comprise a heat source. The heat source can be an oven, a convection oven, a microwave energy source, an electron beam irradiation source, an infrared heating source, a radiofrequency heating source, a conduction heating source, a radiation source, or an open flame source.

The gaseous composition resulting from the heating of the plant or fungus material can be contained within the enclosure under variable or static pressure. For example, the plant or fungus material can be heated in a sealed enclosure at a predetermined temperature for a predetermined period of time. In some embodiments, the enclosure is then unsealed, for example, by opening a valve, placing the gaseous composition in contact with the rest of the apparatus. In some embodiments, the enclosure can then be resealed, and the plant or fungus material can be heated again at a predetermined temperature for a predetermined period of time. The cycle comprising heating the plant or fungus material in a sealed enclosure followed by exposing the resulting gaseous composition to the rest of the apparatus can be repeated multiple times.

Alternatively, the plant or fungus material can be heated at a predetermined temperature for a predetermined period of time in an enclosure that is connected to the affinity medium, and vacuum is applied to the affinity medium to continuously pull a flow of gaseous composition from the enclosure through the affinity medium. In this case the enclosure can only be open to the gas outlet connecting it to the affinity medium. Alternatively, the enclosure can additionally be equipped with a gas inlet, providing a flow of air, oxygen, or an inert or reducing gas (for example, nitrogen, a nitrogen/hydrogen mixture, or other inert or non-oxidizing gases or gas mixtures).

Prior to contacting the affinity medium, the gaseous composition can be filtered through one or more porous membranes. The porous membranes are designed to remove components of the gaseous composition, such as solid particles, that are larger than 5-50 μm, preferably larger than 20 μm. The porous membrane can be a metal filter, such as stainless steel wire or aluminum wire filter, or a polymer filter, such as a Nylon® filter. The porosity of the filter can be, for example, 325 mesh, 400 mesh, 450 mesh, 500 mesh, 635 mesh, 1200 mesh, or 2400 mesh. Several porous membranes or same or different porosity can be used to filter the particulate components from the gaseous composition prior to contacting the affinity medium.

The porous membrane can be placed directly before the affinity medium in the flow of the gaseous composition. In some embodiments, two porous membranes can be placed on the opposite sides of the affinity medium, providing filtration of the gaseous composition and physical containment of the affinity medium. Alternatively, a porous membrane can encapsulate the affinity medium. Alternatively or additionally, one or more porous membranes can be placed in the flow path of the gaseous composition out of contact with the affinity medium.

The gaseous composition can be purified prior to contacting the affinity medium by passing through one or more cleaning media. A cleaning medium can be a liquid, for example, a solution comprising water, NaCl, KCl, $MgSO_4$, $NaHCO_3$, $K_2CO_3$, LiCl, $Na_2CO_3$, $H_3PO_4$, HCl, LiOH, KOH, NaOH, detergent, purified protein, recombinant protein, or mixtures thereof. The cleaning medium can also be a solution comprising water, methanol, ethanol, propanol, isopropanol, acetonitrile, or mixtures thereof. The liquid can comprise one or more salt, acid, or base, such as NaCl, KCl, $MgSO_4$, $NaHCO_3$, $K_2CO_3$, LiCl, $Na_2CO_3$, $H_3PO_4$, HCl, LiOH, KOH, NaOH. The cleaning medium can comprise one or more detergent, purified protein, or recombinant protein. The cleaning medium can comprise a buffer, for example, a citric buffer, a phosphate buffer, an acetate buffer, or a borate buffer. The cleaning medium can have a pH from about 0 to about 14. For example, the cleaning medium can have pH about 0, about 1, about 2, about 3, about 4, about 5, about 6, about 7, about 8, about 9, about 10, about 11, about 12, about 13, or about 14.

In some embodiments, the cleaning medium can be heated to a temperature from about 30° C. to about 70° C. For example, the cleaning medium can be heated to about 30° C., about 35° C., about 40° C., about 45° C., about 50° C., about 55° C., about 60° C., about 65° C., or about 70° C. In some embodiments, the cleaning medium can be cooled to a temperature from about 15° C. to about 5° C. For example, the cleaning medium can be cooled to about 15° C., about 10° C., or about 5° C.

The cleaning medium can be contained in a bubbler. The gas intake of the bubbler can be directly or indirectly connected to the enclosure used for heating the plant or fungus material. The gas outlet of the bubbler can be directly or indirectly connected to the affinity medium. The gaseous composition can pass through the cleaning medium prior to passing through a porous membrane, after passing through a porous membrane, or the bubbler can be positioned between two or more porous membranes in the flow path of the gaseous composition. Multiple bubblers with same or different cleaning media can be positioned in the flow path of the gaseous composition prior to the affinity medium.

The plant or fungus material can be heated in a vessel, for example, a metal, glass or ceramic vessel. The enclosure can consist of the vessel, or can comprise the vessel and other elements, such as the one or more porous membranes and one or more cleaning media.

In some embodiments, the gaseous composition contacts the affinity medium. In certain embodiments, the gaseous composition passes through the affinity medium. The volatile compounds in the gaseous composition having affinity for the affinity medium are retained on the affinity medium.

The affinity medium can comprise a lipophilic affinity medium, preferentially associating or binding with lipophilic compounds. The lipophilic affinity medium can comprise materials known in the art, such as stationary media for reverse-phase chromatography separation. The affinity medium can comprise a core material, such as silica, alumina, mixed metal oxide, or a polymer covalently functionalized with a hydrocarbon group. The term "hydrocarbon" as used herein is defined to include alkyl groups and aryl groups, having from 1 to 100 carbons. Alkyl groups can be selected from straight, branched, or cyclic alkyls. Aryl groups can be selected from monocyclic, bicyclic, and tricyclic aromatic hydrocarbon groups including phenyl, naphthyl, and the like. Alkyl and aryl groups can be optionally substituted with functional groups such as —OH, —CN, $—NH_2$, $—NO_2$, ketone, ester, ether, alkoxy- or siloxy groups. For example, the lipophilic affinity medium can comprise silica, alumina, mixed metal oxide, or a polymer, covalently functionalized with non-polar substituents, such as $C_{2-24}$ alkyl, $C_{6-12}$ aryl, $C_{2-24}$ alkyl($C_{6-12}$ aryl), tri($C_{1-12}$ di($C_{1-12}$ alkyl)silyl($C_{2-24}$ alkyl) groups. In some embodiments, the lipophilic affinity medium comprises a core material functionalized with $C_2$, $C_8$, or $C_{18}$ alkyl groups, phenyl groups, —CN groups, or $C_2$-$C_5$ alkyl groups substituted with —CN. Examples of lipophilic affinity media are disclosed, for example, in U.S. Pat. Nos. 6,258,264, 9,724,622, and U.S. Pat. Appl. Pub. No. US2003/0102260, each of which is incorporated herein by reference in its entirety. The following materials can be used, for example, as affinity media: C18-reversed phase silica gel (Millipore Sigma, Catalog number 60757); SiliaSphere PC Spherical Silica Gel, C18 Polymeric, 40-75 μm, 100 Å (SiliCycle, catalog number S33230E); and C18 Silica Gel (Octadecyl Phase) (Sorbtech, catalog number 63546).

Upon contact of the gaseous composition with the lipophilic affinity medium, the lipophilic molecules remain contained within the lipophilic affinity medium, while the hydrophilic molecules pass through the lipophilic affinity medium with the rest of the gaseous composition, without getting retained.

An affinity medium can comprise a hydrophilic affinity medium, preferentially associating or binding with hydrophilic molecules. The hydrophilic affinity medium can comprise materials known in the art, such as stationary media for normal-phase chromatography separation. For example, a hydrophilic affinity medium can comprise silica, alumina, mixed metal oxide, or a polymer which can be optionally covalently functionalized with polar substituents, such as $—NH_2$, $—C_6H_5SO_3H$, ($C_{1-12}$ alkyl)($C_6F_5$), diol, silanol, or zwitterion.

In some embodiments, an affinity medium can selectively bind or associate with particular molecules or classes of molecules through ionic interactions, host-guest interactions, hydrogen bonding, Van der Waals forces, or immobilized metal ion interactions. For example, an affinity medium comprising a molecularly imprinted polymer (MIP) can selectively bind specific molecules due to the presence of the binding sites in the MIP that are designed to have high affinity, selectivity, and specificity for those molecules.

MIPs are known in the art. MIPs are polymeric matrices obtained using molecular imprinting technology, which is a technique employed in designing artificial receptors with a predetermined selectivity and specificity for a given analyte. MIPs are robust molecular recognition elements able to mimic natural recognition entities, such as antibodies and biological receptors, useful to separate and analyze complicated samples such as biological fluids and environmental samples. The main advantages of MIPs are their high selectivity and affinity for the target molecule used in the imprinting procedure. Imprinted polymers have higher physical robustness, strength, resistance to elevated temperature and pressure, and inertness towards acids, bases, metal ions and organic solvents compared to biological systems such as proteins and nucleic acids.

Molecular imprinting is a synthetic technique providing highly cross-linked polymers capable of selective molecular recognition. During molecular imprinting polymerization of a monomer occurs in the presence of the target molecule (template), which is incorporated in the polymer matrix. The process starts with dissolution of template, functional monomer, cross-linking agent, and initiator in a porogenic solvent. Functional monomers are chosen to interact with the template molecule since the formation of a stable template-monomer complex is fundamental for the success of molecular recognition. Monomers are positioned spatially around the template, and the position is fixed by copolymerization with cross-linking monomers. The polymer obtained is a porous matrix possessing microcavities with a three-dimensional structure complementary to that of the template. The removal of the template molecules from the polymer, for example, by extraction with a solvent, leaves binding sites that are complementary in shape to the template. Consequently, the resulting polymer recognizes and binds selectively with the template molecules. The binding sites can show different characteristics, depending on the interactions established during the polymerization.

An affinity medium can comprise a zeolite, a Metal-Organic Framework (MOF), or a Covalent Organic Framework (COF). Zeolites, MOFs, and COFs are known in the art as porous materials capable of selectively absorbing and/or binding molecules with specific spatial or electronic characteristics. Zeolites are microporous, aluminosilicate minerals commonly used as commercial adsorbents. MOFs are a class of porous polymeric material, consisting of metal ions linked together by organic bridging ligands. COFs are crystalline porous polymeric materials consisting of covalently bound organic fragments bonds that usually have rigid structures, exceptional thermal stabilities (to temperatures up to 600° C.), have low densities, and are generally stable in water.

An affinity medium can be non-porous. Typically, the affinity medium comprises pores. In such an affinity medium, lowering pressure within the affinity medium lowers gas pressure within the pores in gaseous communication with the vacuum source. The average pore size of the affinity medium can be from about 10,000 Å to about 50 Å. In some embodiments, the average pore size of the affinity medium is about 10,000 Å, about 5000 Å, about 1000 Å, about 900 Å, about 800 Å, about 700 Å, about 600 Å, about 500 Å, about 400 Å, about 300 Å, about 200 Å, about 190 Å, about 180 Å, about 170 Å, about 160 Å, about 150 Å, about 140 Å, about 130 Å, about 120 Å, about 110 Å, about 100 Å, about 90 Å, about 80 Å, about 70 Å, about 60 Å, or about 50 Å. In certain embodiments, the average pore of the affinity medium is from about 200 Å to about 90 Å. In some embodiments the average pore size of the affinity medium is about 100 Å.

The affinity medium can comprise a monolithic phase, for example, a continuous polymeric phase. Alternatively or additionally, the affinity medium can comprise a plurality of particles, such as polymer, silica, or alumina particles. In some embodiments, some or all of the particles of the affinity medium can be porous. In certain embodiments, the particles of the affinity medium are non-porous.

The affinity medium can be a monolithic porous material. An affinity medium can comprise layers of affinity media with same or different porosity characteristics. For example, an affinity medium can comprise several layers of porous media, wherein each subsequent layer possessing smaller average pore size than the previous one. An affinity medium can comprise one or more layers of different or same monolithic porous material and one or more layers of porous or non-porous particles.

The gaseous composition can pass through the same affinity medium one or multiple times. Additionally, or alternatively, the gaseous composition can pass through one or more affinity media. If the gaseous composition passes through multiple affinity media, the affinity media can be the of same or different composition such as the nature of their chemical affinity (for example, hydrophilic, lipophilic, or exhibiting affinity for a specific class of molecules) or in terms of the presence and average size of pores. The multiple affinity media can be contacting each other or can be separated in space.

The affinity medium can be of various sizes and dimensions. In embodiments, the affinity medium has an aspect ratio of about 5 or less (e.g., (length to width ratio), wherein the longer dimension of the affinity medium corresponds to the flow path of the gaseous composition. For example, the affinity medium can have a cylindrical shape, wherein the length of the cylinder is no more than five times the diameter of the cross-section of the cylinder.

The gaseous composition is drawn through the affinity medium by a vacuum source directly or indirectly connected to the affinity medium. The vacuum source applies reduced pressure to the affinity medium (typically, pores of the affinity medium), directly or indirectly, which draws the gaseous composition from the enclosure through the affinity medium. For example, the applied reduced pressure can be from about 0.1 Torr to about 250 Torr. In some embodiments, the vacuum can be about 0.1 Torr, about 0.2 Torr, 0.3 Torr, about 0.5 Torr, about 0.6 Torr, about 0.7 Torr, about 0.8 Torr, about 0.9 Torr, about 1 Torr, about 5 Torr, about 10 Torr, about 20 Torr, about 30 Torr, about 40 Torr, about 50 Torr, about 60 Torr, about 70 Torr, about 80 Torr, about 90 Torr, about 100 Torr, about 110 Torr, about 120 Torr, about 130 Torr, about 140 Torr, about 150 Torr, about 160 Torr, about 170 Torr, about 180 Torr, about 190 Torr, about 200 Torr, about 210 Torr, about 220 Torr, about 230 Torr, about 240 Torr, or about 250 Torr.

A vacuum source can be a vacuum pump. A vacuum pump can be a positive displacement pump, a kinetic pump, such as a diffusion pump or a turbomolecular pump, or an entrapment pump, such as a cryopump. Different types of vacuum pumps for creating specific ranges of reduced pressure are known in the art.

The affinity medium that has been contacted with the gaseous composition can be washed using a washing solution or a washing bath to remove the undesired components of the gaseous composition that were retained on the affinity medium. The affinity medium can be immersed in the washing solution, or the washing solution can permeate through the affinity medium under applied pressure or due to the force of gravity, eluting the undesired components. The volume of the washing solution can be from about 5 to about 100 times the volume of the affinity medium. For example, the volume of the washing solution can be about 5, about 6, about 7, about 8, about 9, about 10, about 15, about 20, about 25, about 30, about 35, about 40, about 45, about 50, about 55, about 60, about 65, about 70, about 75, about 80, about 85, about 90, about 95, or about 100 larger than the volume of the affinity media.

The washing solution can comprise a solvent selected from water, methanol, ethanol, propanol, isopropanol, or acetonitrile. Additionally, the washing solution can comprise one or more salt, acid, or base, such as NaCl, KCl, $MgSO_4$, $NaHCO_3$, $K_2CO_3$, LiCl, $Na_2CO_3$, $H_3PO_4$, HCl, LiOH, KOH, or NaOH. The washing solution can also comprise a detergent, a purified protein, or a recombinant protein. The washing solution can comprise a buffer. Buffers are known in the art, and can include, for example, a citric buffer, a phosphate buffer, an acetate buffer, or a borate buffer. The washing solution can have pH from about 0 to about 14. For example, the washing solution can have pH about 0, about 1, about 2, about 3, about 4, about 5, about 6, about 7, about 8, about 9, about 10, about 11, about 12, about 13, or about 14.

In some embodiments, the washing solution can be heated to a temperature from about 30° C. to about 70° C. For example, the washing solution can be heated to about 30° C., about 35° C., about 40° C., about 45° C., about 50° C., about 55° C., about 60° C., about 65° C., or about 70° C. In some embodiments, the washing solution can be cooled to a temperature from about 15° C. to about 5° C. For example, the washing solution can be cooled to about 15° C., about 10° C., or about 5° C.

The affinity medium can be washed in multiple washing solutions. The multiple washing solutions can be the of same or different composition. For example, the affinity medium can be washed by flowing the first washing solution through the affinity medium, followed by immersion of the affinity medium in the second washing solution. Alternatively or additionally, the affinity medium can be soaked in a series of washing solutions, and/or eluted with a series of elution solutions.

The desired compounds can be separated from the affinity medium by contacting the affinity medium with an elution solution. The affinity medium can be immersed in the elution solution, or the elution solution can permeate through the affinity medium, for example, under applied pressure or due to the force of gravity. Contacting of the affinity medium with the elution solution provides an elution mixture which contains the desired compounds. The elution solution can comprise a solvent. The solvent can be selected from methanol, ethanol, a methanol/water mixture, an ethanol/water mixture, pentane, hexane, heptane, cyclohexane, acetone, tetrahydrofuran, ethyl acetate, diethyl ether, or a mixture thereof.

Different fractions of the desired compounds can be separated from an affinity medium by contacting the affinity medium with different elution solutions. An affinity medium can be repeatedly contacted with an elution solution of the same or different compositions.

The elution solution can be heated to a temperature from about 25° C. to about 50° C. For example, the elution solution can be heated to about 25° C., about 30° C., about 35° C., about 40° C., about 45° C., or about 50° C.

The elution solution can be cooled to a temperature from about 15° C. to about 5° C. For example, the elution solution can be cooled to about 15° C., about 10° C., or about 5° C., The desired compounds can be isolated from the elution mixture by removal of the solvent or solvents. For example, the solvent or solvents can be removed by evaporation. Solvent or solvents evaporation can be performed at ambient temperature, or a temperature higher than ambient, or a temperature lower than ambient. Evaporation of the solvent or solvents can be performed under ambient pressure or under reduced pressure.

In some embodiments, the solvent or solvents can be removed by lyophilization.

The compounds can be isolated from the elution mixture by column chromatography. The elution mixture can be loaded on the column directly as it was obtained from the affinity medium, or it can be chemically treated or concentrated prior to the chromatographic separation. In some embodiments, the affinity medium can be attached to the chromatographic column, and the elution mixture resulting from passing of the elution solution through the affinity medium can be directly deposited on the chromatographic column. The desired compounds can be then subjected to chromatographic separation according to methods known in the art.

The elution mixture can also be separated by fractionation by solubility. The elution mixture can be contacted with fractionation solutions, for example, by vigorous mixing followed by spontaneous phase separation. The components of the elution mixture can be transferred into different fractionation solutions based on their relative solubility in the contacting solutions. The desired compounds can be further isolated by removing the volatile components of the fractionation solution by evaporation or lyophilisation.

In some embodiments, the method further comprises condensing a first fraction of the gaseous composition via adiabatic expansion before the gaseous composition contacts the affinity medium. For example, the gaseous composition can exit the enclosure through a connector of variable diameter, e.g., a connector containing a section of a first diameter and a section of a second diameter, where the section of a first diameter is proximal to the enclosure. If the second diameter is larger than the first diameter, the gaseous composition can expand adiabatically upon entering the section of the second diameter, resulting in rapid decrease of the temperature of the gaseous composition and triggering condensation of a fraction of the gaseous composition inside the connector.

The ratio of the first diameter to the second diameter can be varied to obtain different amounts of the first fraction. The first fraction can then be collected by disconnecting the connection the enclosure and/or the affinity filter and allowing the first fraction to flow out of the connection into an appropriate receptacle. Heating the connection reduces viscosity of the first fraction and can be used to facilitate the isolation. The first fraction can also be solubilized in the connection with a small amount of solvent, such as ethanol, to facilitate removal.

In some embodiments, the present invention relates to an apparatus for obtaining compounds from a plant or fungus material, comprising a) an enclosure configured for thermal treatment of the plant or fungus material and for enclosing a gaseous composition resulting from the thermal treatment;

b) an affinity medium;

c) a porous membrane positioned such that the gaseous composition contacts the porous membrane before contacting the affinity medium; and d) a vacuum source configured to lower pressure within the affinity medium.

Figure 2:
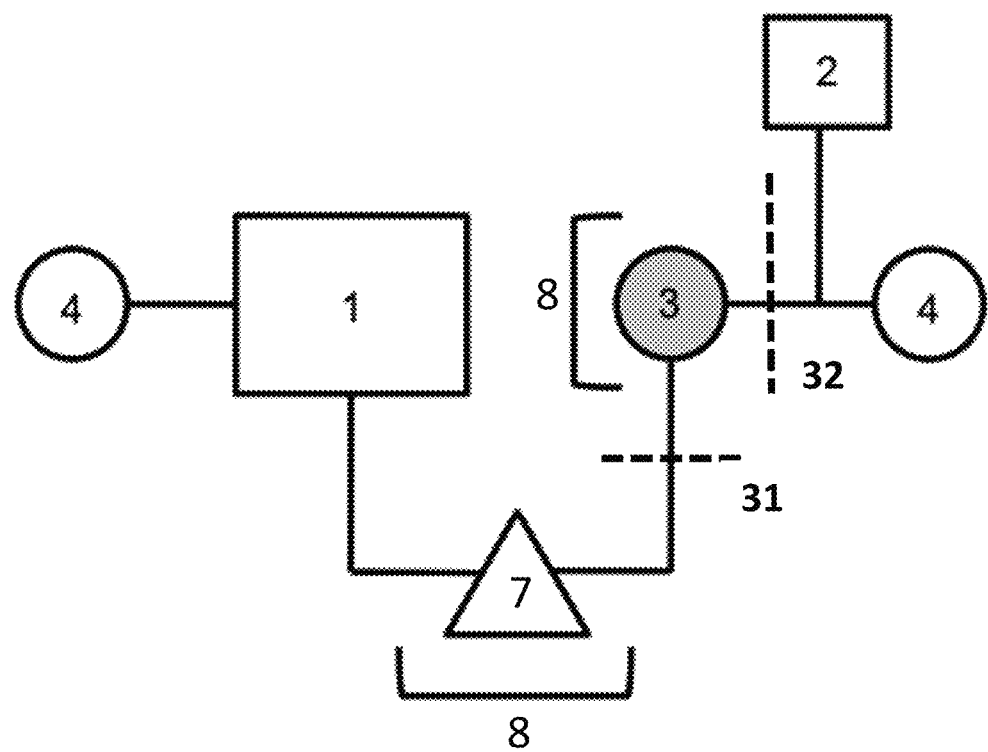
FIG. 2 is a schematic representation of the apparatus for obtaining compounds from a plant or fungus material with additional elements (as compared to FIG. 1) (1—enclosure for thermal treatment of the plant or fungus material; 2—vacuum source; 3—affinity medium; 31—optional porous membrane; 32—optional structural support for the affinity medium which can be a porous membrane; 4—optional exhaust filter; 7—cleaning medium; 8—heating/cooling elements).

The apparatus can additionally comprise further elements, such as exhaust filters, cleaning media such as bubblers, porous membranes, and heating or cooling elements. A simplified schematic representation of an apparatus equipped with additional elements is shown in FIGS. 1 and 2.

The elements of the apparatus, such as the enclosure, the vessel comprised within the enclosure, the cleaning media, the porous membranes, the affinity media, and the vacuum source, can be connected by connectors, such as tubes or pipes, that allow the gaseous composition to flow between the different elements of the apparatus. The connectors can be made of metal, such as steel, stainless steel, or aluminum, or of glass, ceramic materials, or polymers.

The cannabidiol containing compositions described herein, can be used, for example, for treating spasticity, anorexia, nausea, pain, tobacco addiction, acne, fibromyalgia, anxiety, inflammation, schizophrenia or insomnia.

Definitions

As used herein, "plant material" refers to a whole plant, plant part (e.g. bark, wood, leaves, stems, roots, flowers, fruits, trichomes, seeds, berries or parts thereof). Whole plant or plant parts can be raw or dried. Whole plant or plant parts can be ground into a powder. "Plant material" additionally refers to plant exudate, plant wax, plant extract, plant resin, plant distillate, plant extract concentrate, or a mixture thereof. In certain instances, plant material refers to a plant material of *Cannabis sativa* or *Mitragyna speciose* (Kratom).

As used herein, "fungus material" refers to a whole fungus, fungus part (e.g. cap, ring, volva, stem, mycelium, or parts thereof). Whole fungus or fungus parts can be raw or dried. Whole fungus or fungus parts can be ground into a powder. "Fungus material" additionally refers to fungus exudate, fungus extract, fungus resin, fungus distillate, fungus extract concentrate, or a mixture thereof. In certain instances, fungus material refers to a fungus material of *Hericium erinaceus*.

As used herein, the term "*Cannabis sativa*" refers to the wild type *Cannabis sativa* and also variants thereof, including *cannabis* chemovars which naturally contain different amounts of the individual cannabinoids, *Cannabis sativa* subspecies indica, including the variants var. indica and var. kafiristanica, *Cannabis* indica and also plants which are the result of genetic crosses, self-crosses or hybrids thereof. The term "*Cannabis* plant material" is to be interpreted accordingly as encompassing plant material derived from one or more *cannabis* plants.

As used herein, "hemp *Cannabis*" or "hemp" refers to a *Cannabis sativa* plant or plant material containing less than 0.3% of the combined amount of Δ9-tetrahydrocannabinol (Δ9THC) and tetrahydrocannabinolic acid (THCA).

As used herein, "medical *Cannabis*" refers to a *Cannabis sativa* plant containing more than 0.3% of the combined amount of Δ9-tetrahydrocannabinol (Δ9THC) and tetrahydrocannabinolic acid (THCA).

As used herein, unless otherwise noted, THC refers to Δ9-tetrahydrocannabinol (Δ9THC).

As used herein, the term "retention time" refers to the retention times as determined using the method of Example 2. Further, as used herein in the context of cannabidiol containing compositions or cannabidiol derivatives, the term "relative retention time" of a given peak (or respective given compound) $RRT_{peak}$ refers to the retention time of the given peak $RT_{peak}$ relative to the retention time of cannabidiol $RT_{CBD}$, that is, $RRT_{peak}=RT_{peak}/RT_{CBD}$.

As used herein, the term "affinity medium" refers to a medium, such as a porous or non-porous material, a liquid, or a plurality of particles, which displays greater affinity for non-covalent physical association or binding to selected molecules relative to other molecules in a sample. An affinity medium can be a lipophilic affinity medium, preferentially associating or binding with lipophilic molecules. Alternatively, an affinity medium can be a hydrophilic affinity medium, preferentially associating or binding with hydrophilic molecules. In some embodiments, an affinity medium can selectively bind or associate with particular molecules or classes of molecules through ionic interactions, host-guest interactions, hydrogen bonding, Van der Waals forces, or immobilized metal ion interactions. For example, an affinity medium comprising a molecularly imprinted polymer (MIP) can selectively bind specific molecules due to the presence of the binding sites in the MIP that are designed to have high affinity, selectivity, and specificity for those molecules. The affinity medium can comprise zeolites, MOFs, or COFs.

The term "alkyl," as used herein, means a saturated, straight-chain or branched aliphatic group. In one aspect, an alkyl group contains 1-20 or 6-18 carbon atoms, for example, 2, 8, or 18 carbon atoms. Alkyl includes, but is not limited to, methyl, ethyl, propyl, iso-propyl, n-butyl, sec-butyl, t-butyl, and the like.

The term "aryl," alone or in combination, as used herein, means a carbocyclic aromatic system containing one or more rings, which may be attached together in a pendent manner or may be fused. In particular embodiments, aryl is one, two or three rings. In one aspect, the aryl has five to twelve ring atoms. The term "aryl" encompasses aromatic radicals such as phenyl, naphthyl, tetrahydronaphthyl, indanyl, biphenyl, phenanthryl, anthryl and acenaphthyl. An "aryl" group can have 1 to 5 substituents, such as alkyl, hydroxyl, halo, haloalkyl, nitro, cyano, alkoxy, aminoalkyl, and the like.

The term "haloalkyl," as used herein, means an aliphatic group which is substituted with one or more halogen atoms. In some embodiments, haloalkyl refers to a perhalogenated aliphatic group. In some embodiments, haloalkyl refers to an alkyl group which is substituted with one or more halogen atoms. Exemplary haloalkyl groups include —$CF_3$, —$CCl_3$, —$CF_2CH_3$, —$CH_2CF_3$, —$CH_2(CF_3)_2$, —$CF_2(CF_3)_2$, and the like.

The terms "amine" and "amino" are art-recognized and refer to both unsubstituted and substituted amines and salts thereof, e.g., a moiety that can be represented by

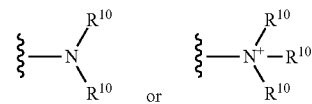

wherein each $R^{10}$ independently represents a hydrogen or a hydrocarbyl group, or two $R^{10}$ are taken together with the N atom to which they are attached complete a heterocycle having from 4 to 8 atoms in the ring structure. The term "aminoalkyl", as used herein, refers to an alkyl group substituted with an amino group.

The term "alkoxy", as used herein, refers to an alkyl radical attached through an oxygen linking atom. For example, "($C_1$-$C_4$)-alkoxy" includes methoxy, ethoxy, propoxy, and butoxy.

The term "silanol", as used herein, refers to compounds or radicals having —$Si(R^{20})_2OH$, wherein each $R^{20}$ independently represents —OH, alkyl, aryl, alkoxy, or syloxy group.

The term "siloxy", as used herein, refers to a —$OSi(R^{30})_3$, wherein each $R^{30}$ independently represents alkyl, aryl, or alkoxy group.

Unless specifically stated as "unsubstituted," references to chemical moieties herein are understood to include substituted variants. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. Substituents can include any substituents described herein, for example, an alkyl, a halogen, a hydroxyl, a carbonyl (such as a carboxyl, an alkoxycarbonyl, a formyl, or an acyl), a thiocarbonyl (such as a thioester, a thioacetate, or a thioformate), an alkoxy, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that substituents can themselves be substituted, if appropriate.

As used herein, the term "subject" and "patient" may be used interchangeably, and means a mammal in need of treatment, e.g., companion animals (e.g., dogs, cats, and the like), farm animals (e.g., cows, pigs, horses, sheep, goats and the like) and laboratory animals (e.g., rats, mice, guinea pigs and the like). Typically, the subject is a human in need of treatment.

As used herein, the term "treating" or 'treatment" refers to obtaining desired pharmacological and/or physiological effect. The effect can be prophylactic or therapeutic, which includes achieving, partially or substantially, one or more of the following results: partially or totally reducing the extent of the disease, disorder or syndrome; ameliorating or improving a clinical symptom or indicator associated with the disease, disorder or syndrome; delaying, inhibiting or decreasing the likelihood of the progression of the disease, disorder or syndrome; or partially or totally delaying, inhibiting or reducing the likelihood of the onset or development of disease, disorder or syndrome.

As used herein, "effective amount" means that amount of a composition that elicits the desired biological response in a subject. Such response includes alleviation of the symptoms of the disease, disorder or syndrome being treated.

As used herein, "pharmaceutically acceptable carrier" means compounds and compositions that are of sufficient purity and quality for use in the formulation of a composition described herein and that, when appropriately administered to an animal or human, do not produce an adverse reaction.

As used herein in the context of retention times and relative retention times, "about" refers to the values in a ±1% range of the given retention time or relative retention time. For example, a relative retention time of about 0.677 refers to the relative retention time (and including) 0.677-1%, the relative retention time (and including) 0.677+1%, and all retention times inbetween.

As used herein in the context of temperatures, "about" refers to the temperatures in a ±5° C. range of the given temperature. For example, a temperature of about 100° C. refers to the temperature (and including) 95° C., the temperature (and including) 105° C., and all temperatures inbetween these two temperatures.

As used herein in the context of the amount of cannabidiol derivative in the compositions relative to cannabidiol in the composition, "about" refers to the amounts in a ±0.2% range of the percentage. For example, a percentage of about 2% refers to the percentage (and including) 1.8%, the percentage (and including) 2.2%, and all percentages inbetween.

In all other contexts, the term "about" refers to a ±5% range of the given value (including the range endpoints).

As used herein, a "cannabidiol derivative" refers to a compound which is a chemical derivative of cannabidiol formed by thermal treatment (e.g., pyrolysis) of cannabidiol. Typically, cannabidiol derivatives result from oxidation, isomerization and/or transformation of cannabidiol due to thermal treatment.

As used herein, a "tetrahydrocannabinol derivative" refers to a compound which is a chemical derivative of tetrahyrdocannabinol formed by thermal treatment (e.g., pyrolysis) of tetrahyrdocannabinol. Typically, tetrahydrocannabinol derivatives result from oxidation, isomerization and/or transformation of tetrahydrocannabinol due to thermal treatment.

EXAMPLES

Abbreviations

2-AG 2-arachidonylglycerol
AEA anandamide
Δ9THC Δ9-tetrahydrocannabinol
Δ10THC Δ10-tetrahydrocannabinol
exo-THC exo-tetrahydrocannabinol
CBD cannabidiol
CBND cannabinodiol
omCBD o-methylcannabidiol
CBN cannabinol
omCBN o-methylcannabinol
oprCBN o-propylcannabinol
opeCBN o-pentylcannabinol
ECS endocannabinoid system
HPLC high performance liquid chromatography
UHPLC-HRMS/MS ultra-high-performance liquid chromatography-high resolution mass spectrometry/mass spectrometry
TOF time of flight
HCD hemp *Cannabis* distillate
MCD medical *Cannabis* distillate
CB1 or CBR1 cannabinoid receptor 1
CB2 or CBR2 cannabinoid receptor 2
MGL monoacylglycerol lipase
ABHD6 alpha/beta hydrolase domain 6

Example 1. Extraction and Partial Purification of CBD from *Cannabis* Saliva Flower

Figure 4:
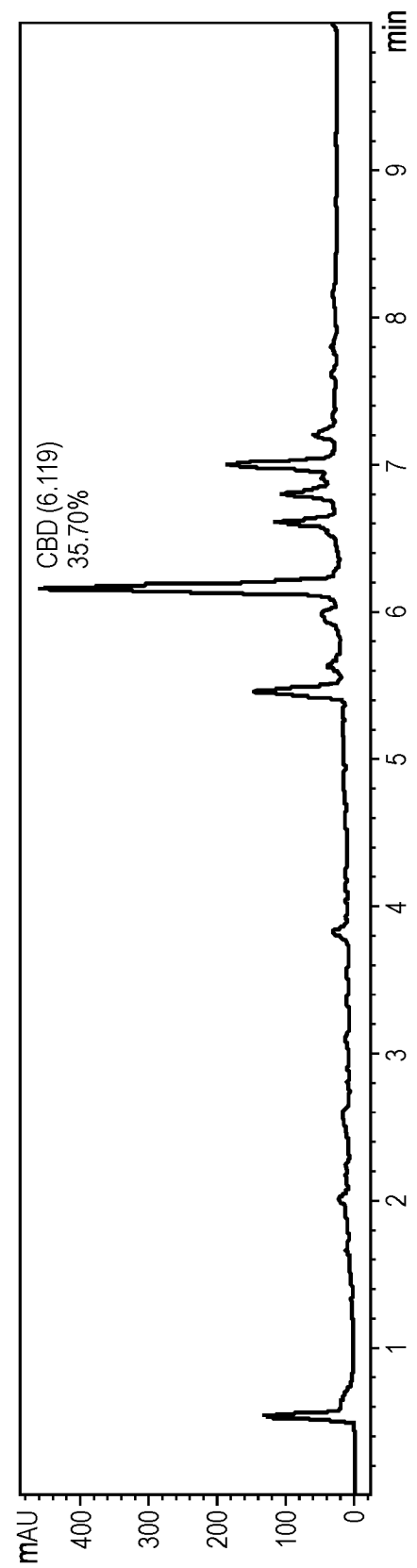
FIG. 4 is an HPLC trace of compounds obtained from hemp using thermal treatment at 150° C. to 175° C., showing a CBD peak (35.7% of the total peak area) with retention time 6.119 min.

*Cannabis sativa* (hemp) flower was cut into small particles about 2-5 mm in diameter. The ground flower was placed into a heating chamber equipped with a gas inlet and gas outlet. The heating chamber was sealed and allowed to reach a temperature between 150-175° C. The vacuum pump connected to the heating chamber through the affinity medium was turned on and the gas inlet and outlet of the heating chamber were opened, allowing air to flow into the heating chamber and then through the affinity medium. The air was allowed to flow through the chamber and the affinity filter for 4 hours at constant temperature. The affinity filter consisted of three filter layers—the first layer, a 635 (20 micron) stainless steel mesh filter (i.e., an example of a porous membrane described herein), the second filter layer, an affinity medium including capture material functionalized for affinity to the desired products (i.e., cannabidiol and cannabidiol derivatives), and a third layer, a further 635 (20 micron) mesh stainless steel filter. The third layer was used here for structural support of the affinity medium. The functionalized capture material consisted of C18-functionalized silica in spherical form; 30-40 μm diameter; 90 Å pore size. After 4 hours, the vacuum pump was turned off, the affinity medium was removed and washed with an acidic aqueous solution (deionized $H_2O$+0.1% phosphoric acid). The affinity medium was then immersed in ethanol, resulting in the elution of the desired compounds from the affinity medium into ethanol. The HPLC trace of the obtained composition determined using the method of Example 2 is shown in FIG. 4.

Example 2. HPLC Analysis

Figure 3:
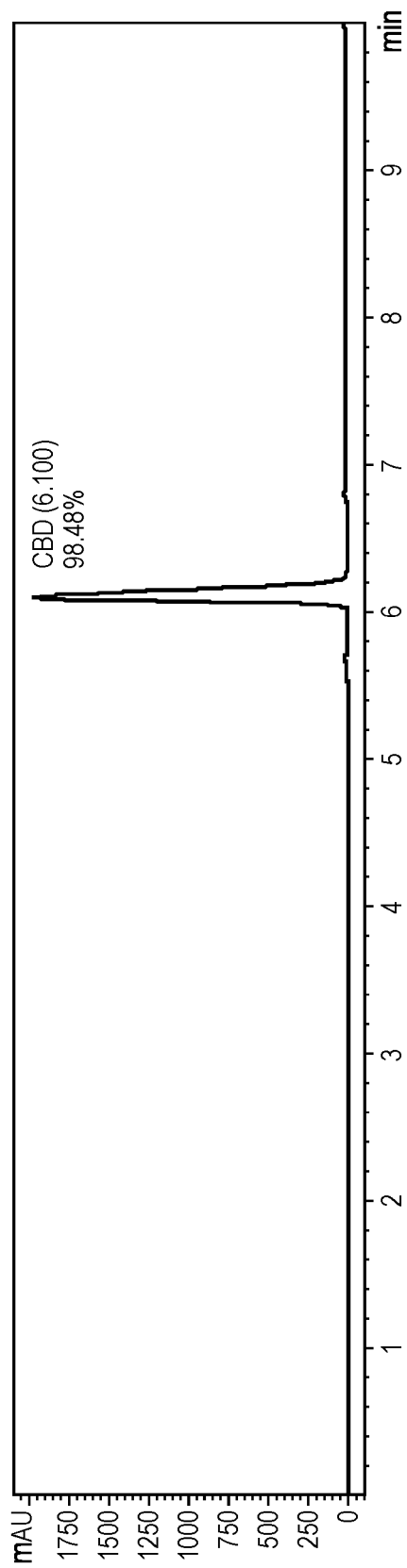
FIG. 3 is an HPLC trace of pure CBD (EcoGen Laboratories, >98% pure).

Samples of multiple dilutions of the compounds obtained by methods disclosed herein were centrifuged at maximum speed for 10 min. A 20 μL aliquot of the resulting supernatant was injected into an Agilent HP 1200 HPLC system for analysis. A gradient elution profile of 100% mobile phase B (deionized $H_2O$ with 0.1% phosphoric acid) to 100% mobile phase A (acetonitrile) was employed for the mixture separation on a Zorbax Eclipse XDB-C18 reverse-phase column (4.6×50 mm, 3 μm, Agilent Technologies, Santa Clara, Calif.) at a 1 mL/min flow rate. CBD eluted at 6.14 min with less than 0.05 min standard deviation in retention time (see FIG. 3). A calibration was performed in order to quantify analytes could be quantified.

Example 3. Extraction, Partial Transformation and Partial Purification of CBD from *Cannabis Sativa* Flower at 300-320° C.

Figure 5:
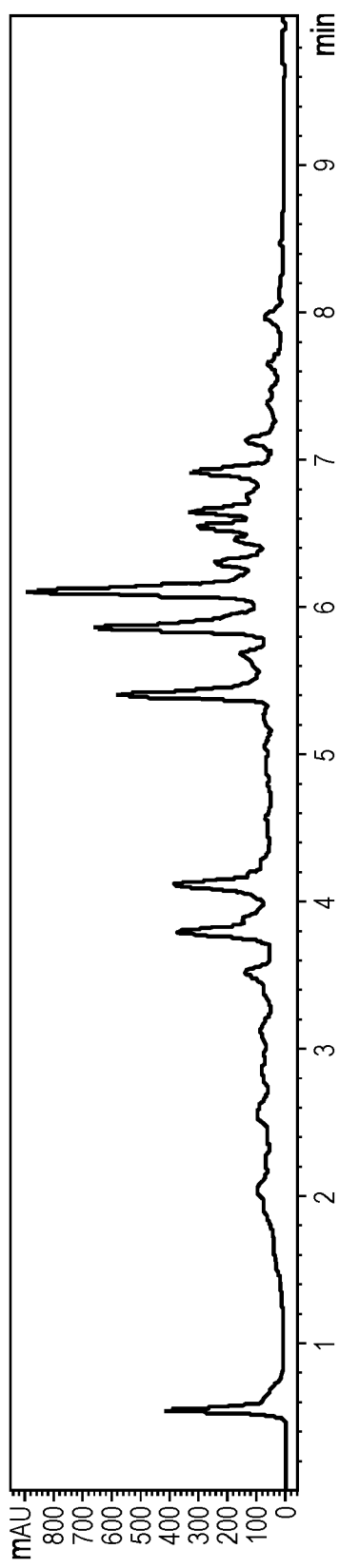
FIG. 5 is an HPLC trace of compounds obtained from hemp using thermal treatment at 300° C. to 320° C.

*Cannabis sativa* (hemp) flower was cut into small particles about 2-5 mm in diameter. The ground flower was placed into a heating chamber equipped with a gas inlet and gas outlet. The heating chamber was sealed and allowed to reach a temperature between 300-320° C. The vacuum pump connected to the heating chamber through the affinity medium was turned on and the gas inlet and outlet of the heating chamber were opened, allowing air to flow into the heating chamber and then through the affinity medium. The air was allowed to flow through the chamber and the affinity filter for 0.25 hours at constant temperature. The affinity filter consisted of three filter layers—a first layer, a 635 (20 micron) stainless steel mesh filter (i.e., an example of a porous membrane described herein), the second layer, an affinity medium including capture material functionalized for affinity to the desired products (i.e., cannabidiol and cannabidiol derivatives), and a third layer, a further 635 (20 micron) mesh stainless steel filter. The third layer was used here for structural support of the affinity medium. The functionalized capture material consisted of C18-functionalized silica in spherical form; 30-40 μm diameter; 90 Å pore size. After 0.25 hours, the vacuum pump was turned off, the capture filter was removed and washed with pure deionized $H_2O$. The affinity medium was then immersed in ethanol, resulting in the elution of the desired compounds from the affinity medium into ethanol. The HPLC trace of the obtained composition determined using the method of Example 2 is shown in FIG. 5.

Example 4. Extraction, Partial Transformation and Partial Purification of CBD from *Cannabis sativa* Flower at 400-420° C.

Figure 6:
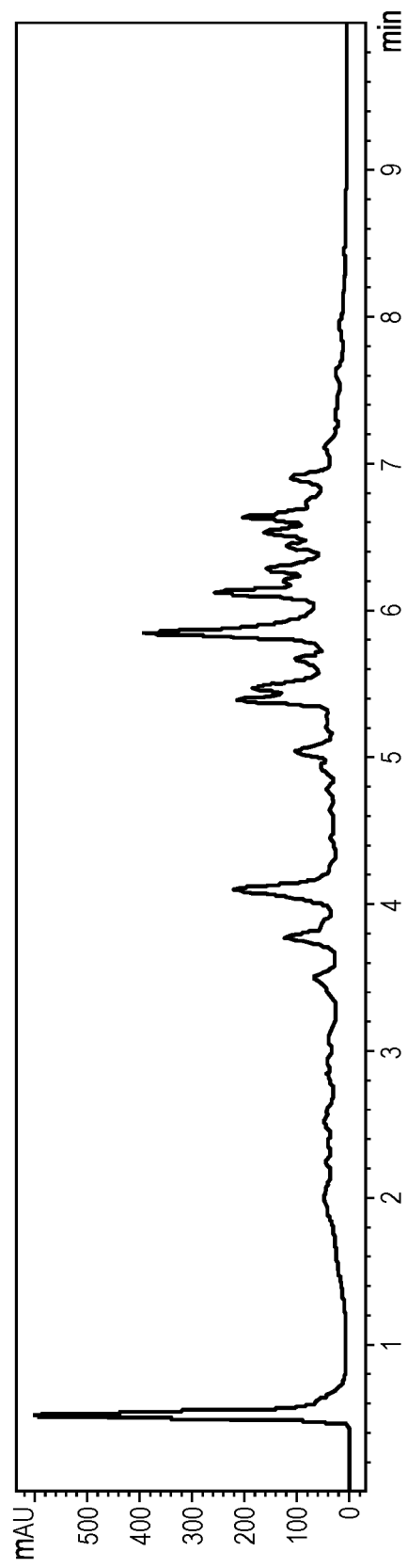
FIG. 6 is an HPLC trace of compounds obtained from hemp using thermal treatment at 400° C. to 420° C.

*Cannabis sativa* (hemp) flower was cut into small particles about 2-5 mm in diameter. The ground flower was placed into a heating chamber equipped with a gas inlet and gas outlet. The heating chamber was sealed and allowed to reach a temperature between 400-420° C. The vacuum pump connected to the heating chamber through the affinity medium was turned on and the gas inlet and outlet of the heating chamber were opened, allowing air to flow into the heating chamber and then through the affinity medium. The air was allowed to flow through the chamber and the affinity filter for 0.20 hours at constant temperature. The affinity filter consisted of three filter layers—the first layer, a 635 (20 micron) stainless steel mesh filter (i.e., an example of a porous membrane described herein), the second filter layer, an affinity medium including capture material functionalized for affinity to the desired products (i.e., cannabidiol and cannabidiol derivatives), and a third layer, a further 635 (20 micron) mesh stainless steel filter. The third layer was used here for structural support of the affinity medium. The functionalized capture material consisted of C18-functionalized silica in spherical form; 30-40 μm diameter; 90 Å pore size. After 0.20 hours, the vacuum pump was turned off, the capture filter was removed and washed with pure deionized $H_2O$. The affinity medium was then immersed in ethanol, resulting in the elution of the desired compounds from the affinity medium into ethanol. The HPLC trace of the obtained composition determined using the method of Example 2 is shown in FIG. 6.

Example 5. Extraction, Partial Transformation and Partial Purification of CBD from *Cannabis sativa* Flower at Greater than 500° C.

Figure 7:
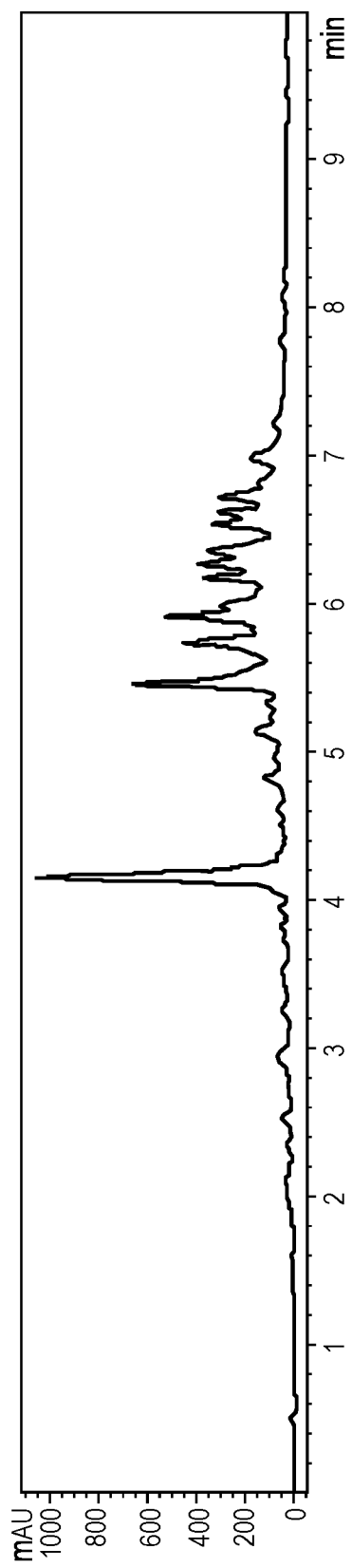
FIG. 7 is an HPLC trace of compounds obtained from hemp using thermal treatment at about 538° C.

*Cannabis sativa* (hemp) flower was cut into small particles about 2-5 mm in diameter. The ground flower was placed into a heating chamber equipped with a gas inlet and gas outlet. The heating chamber was sealed and allowed to reach a temperature greater than 500° C. The vacuum pump connected to the heating chamber through the affinity medium was turned on and the gas inlet and outlet of the heating chamber were opened, allowing air to flow into the heating chamber and then through the affinity medium. The air was allowed to flow through the chamber and the affinity filter for 0.10 hours at constant temperature. The affinity filter consisted of three filter layers—the first layer, a 635 (20 micron) stainless steel mesh filter (i.e., an example of a porous membrane described herein), the second layer, an affinity medium including capture material functionalized for affinity to the desired products (i.e., cannabidiol and cannabidiol derivatives), and the third layer, a further 635 (20 micron) mesh stainless steel filter. The third layer was used here for structural support of the affinity medium. The functionalized capture material consisted of C18-functionalized silica in spherical form; 30-40 μm diameter; 90 Å pore size. After 0.10 hours, the vacuum pump was turned off, the affinity medium was removed and washed with a basic aqueous solution (deionized $H_2O$+0.1% NaOH). The affinity medium was then immersed in ethanol, resulting in the elution of the desired compounds from the affinity medium into ethanol. The HPLC trace of the obtained composition determined using the method of Example 2 is shown in FIG. 7.

With regard to the compositions of Examples 1, and 3-5, it has been found that at least the peaks with the below retention times are present in each of the respective HPLC traces. Additionally, it has been confirmed that these peaks originate from the CBD in isolate form. These peaks are not present in traditional solvent-based extracts. It has further been found that heating to higher temperatures changes the proportion of peaks relative to the cannabidiol.

| Retention Time (mins) ± SD | Relative Retention Time (relative to the retention time of CBD) | Notes |
|---|---|---|
| 4.13 ± 0.03 | 0.677 ± 0.005 | Always present |
| 5.44 ± 0.03 | 0.891 ± 0.005 | Always present |
| 5.80 ± 0.05 | 0.951 ± 0.008 | Higher temperatures (>300° C.) |
| 6.63 ± 0.02 | 1.087 ± 0.003 | Always present |
| 6.78 ± 0.04 | 1.111 ± 0.007 | Always present |

The peak at retention time 5.44±0.03 min corresponds to CBND, and the peak at retention time 6.78±0.04 corresponds to Δ9THC.

Example 6. Extraction and Partial Purification of Compounds from *Hericium erinaceus*

Figure 8:
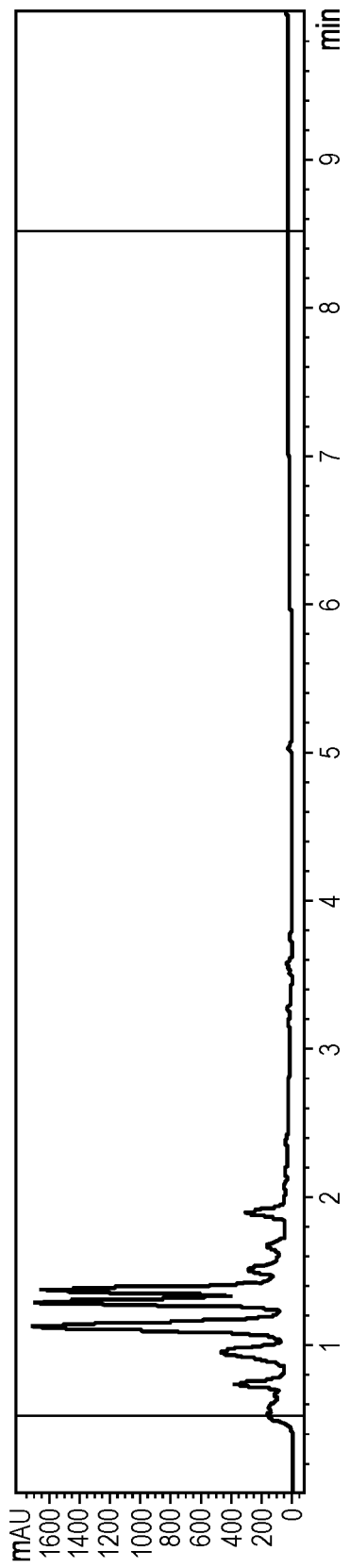
FIG. 8 is an HPLC trace of compounds obtained from *Hericium erinaceus* using thermal treatment at between 200° C. to 215° C.

*Hericium erinaceus* (Lion's mane mushrooms) fruiting bodies were ground into small particles about 2-5 mm in diameter. The ground fruiting bodies were placed into a heating chamber equipped with a gas inlet and gas outlet. The heating chamber was sealed and allowed to reach between 200-215° C. The vacuum pump connected to the heating chamber through the affinity medium was turned on and the gas inlet and outlet of the heating chamber were opened, allowing air to flow into the heating chamber and then through the affinity medium. The air was allowed to flow through the chamber and the affinity filter for 0.25 hours at constant temperature. The affinity filter consisted of three filter layers—the first layer, a 635 (20 micron) stainless steel mesh filter (i.e., an example of a porous membrane described herein), the second layer, an affinity medium including capture material functionalized for affinity to the desired products, and the third layer, a further 635 (20 micron) mesh stainless steel filter. The third layer was used here for structural support of the affinity medium. The functionalized capture material consisted of C18-functionalized silica in spherical form; 30-40 μm diameter; 90 Å pore size. After 0.25 hours, the vacuum pump was turned off, the affinity medium was removed. The affinity medium was then immersed in deionized water and ethanol (50% v/v), resulting in the elution of the desired compounds from the affinity medium into the water/ethanol mixture. The HPLC trace of the obtained composition determined using the method of Example 2 is shown in FIG. 8.

Example 7. Extraction and Partial Purification of Metabolites from *Mitragyna speciosa*

Figure 9:
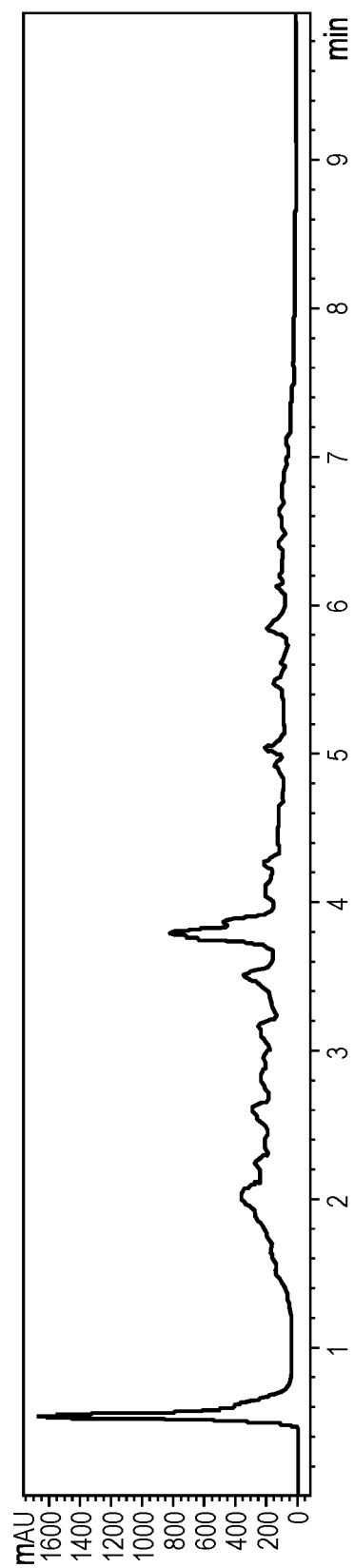
FIG. 9 is an HPLC trace of compounds obtained from *Mitragyna speciosa* using thermal treatment at about 500° C.

*Mitragyna speciosa* (Kratom) leaves were ground into small particles about 2-5 mm in diameter. The ground leaves were placed into a heating chamber equipped with a gas inlet and gas outlet. The heating chamber was sealed and allowed to reach 500° C. The vacuum pump connected to the heating chamber through the affinity medium was turned on and the gas inlet and outlet of the heating chamber were opened, allowing air to flow into the heating chamber and then through the affinity medium. The air was allowed to flow through the chamber and the affinity filter for 0.25 hours at constant temperature. The affinity filter consisted of three filter layers—the first layer, a 635 (20 micron) stainless steel mesh filter (i.e., an example of a porous membrane described herein), the second layer, an affinity medium including capture material functionalized for affinity to the desired products, and the third layer, a further 635 (20 micron) mesh stainless steel filter. The third layer was used here for structural support of the affinity medium. The functionalized capture material consisted of C18-functionalized silica in spherical form; 30-40 μm diameter; 90 Å pore size. After 0.25 hours, the vacuum pump was turned off, the affinity medium was removed. The affinity medium was then immersed in ethanol, resulting in the elution of the desired compounds from the affinity medium into ethanol. The HPLC trace of the obtained composition is shown in FIG. 9.

Example 8. Isolation and Analysis of Cannabinoid-Containing Composition from Hemp *Cannabis*

Dried flower and biomass from hemp *Cannabis* (12% CBD w/w, Twin Arch Farms, NY USA) was ground in a stainless steel blender to fine particle size of less than 5 mm, then approximately 110 g of the ground material was weighed onto four trays for final total weight of 435 g. The trays were placed in a pre-heated vacuum oven (Across International, NJ USA) at 213° C. (425° F.) at atmospheric pressure with both vacuum and inlet ports completely open. The filter system was attached to the oven at the vacuum port at a 90° angle from the port, facing upwards. The affinity filter consisted of three filter layers—the first layer, a 635 (20 micron) stainless steel mesh filter, the second layer, an affinity medium including capture material functionalized for affinity to the desired products, and the third layer, a further 635 (20 micron) mesh stainless steel filter. The third layer was used here for structural support of the affinity medium (polymeric spherical silica gel functionalized with C18, 40-75 μm particle sizes, 100 Å pore size, SiliCycle QC, CAN). The opposing end of the filter system was attached to the vacuum pump. The vacuum pump attached inline to the system was turned on at full power. The system was allowed to run for 1 hr at steady state with the flow rate of air 1.04 L/s before turning off the vacuum pump and oven.

The filter system was detached from the vacuum pump and the oven. 50 mL of ethanol was added to the connection pipe attached to the vacuum port of the oven to solubilize the first fraction collected by adiabatic condensation. The first fraction was collected by removing the connection pipe and allowing the solubilized extract to flow into a glass beaker. The filter system was attached to a 1.5 L filter flask and diaphragm pump. 200 mL of ethanol were added to the filter system while it was closed, manually mixed, then incubated for 10 min at room temperature before being vacuumed into the filter flask. This process was repeated once more with 200 mL and one final time with 100 mL of ethanol. The resulting eluted fractions were added to the first fraction in a 1 L glass round bottom flask. The ethanol was removed by rotary evaporation providing 77 g of the affinity fraction.

The affinity fraction and the first fraction were combined to form a hemp *Cannabis* extract, and the hemp *Cannabis* extract was analyzed using reverse phase HPLC employing a mixture of cannabinoid standards for calibration (HPLC column: Accucore C18 2.6 μm 150×4.6 mm—Thermo Scientific; mobile phases: acetonitrile+0.1% formic acid, 5 mM ammonium formate+0.1% formic acid in water). Concentrations of selected cannabinoids are shown in Table 1; not all cannabinoids were detectable due to lack of the corresponding standards.

| Analyte | Cannabinoid | Conc. (weight %) | Conc. (mg/g) | LOQ (weight %) | LOD (weight %) |
|---|---|---|---|---|---|
| CBDVA | Cannabidivarinic acid | ND | ND | 0.10% | 0.00% |
| CBDV | Cannabidivarin | 0.1% | 1.40 | 0.10% | 0.00% |
| CBDA | Cannabidiolic acid | ND | ND | 0.10% | 0.02% |
| CBGA | Cannabigerolic acid | ND | ND | 0.10% | 0.03% |
| CBG | Cannabigerol | 0.2% | 1.65 | 0.10% | 0.03% |
| CBD | Cannabidiol | 22.4% | 224.11 | 0.10% | 0.01% |

| Analyte | Cannabinoid | Conc. (weight %) | Conc. (mg/g) | LOQ (weight %) | LOD (weight %) |
|---|---|---|---|---|---|
| THCV | Tetrahydrocannabivarin | 0.1% | 1.06 | 0.10% | 0.01% |
| THCVA | Tetrahydrocannabivarinic acid | 0.1% | 1.02 | 0.10% | 0.01% |
| CBN | Cannabinol | 1.6% | 16.07 | 0.10% | 0.01% |
| CBNA | Cannabinolic acid | 0.2% | 1.67 | 0.10% | 0.01% |
| Δ9THC | Δ9-Tetrahydrocannabinol | 0.7% | 7.29 | 0.10% | 0.10% |
| Δ8THC | Δ8-Tetrahydrocannabinol | 0.3% | 2.63 | 0.10% | 0.01% |
| CBL | Cannabicyclol | 0.2% | 2.31 | 0.10% | 0.01% |
| CBC | Cannabichromene | 0.6% | 6.21 | 0.10% | 0.01% |
| THCA | Tetrahydrocannabinolic acid | ND | ND | 0.10% | 0.02% |
| CBCA | Cannabichromenic acid | ND | ND | 0.50% | 0.03% |
| CBLA | Cannabicyclolic acid | ND | ND | 0.10% | 0.01% |

Note:
ND = Not Detected;
LOQ = Limit of Quantitation;
LOD = Limit of Detection

The hemp *Cannabis* extract can be further purified by vacuum distillation. 78.2 g of the hemp *Cannabis* extract was placed into a 1 L 2-neck round bottom boiling flask. The distillation process was performed using a short path distillation unit under 0.05-0.2 mmHg vacuum. The boiling flask was heated by an electric heating jacket. The condenser jacket was initially kept at room temperature while distillation was carried out at 100° C., 125° C., 150° C., 175° C., and 200° C. The condensate collected at the boiling temperatures under 200° C. was discarded. The condenser jacket temperature was increased to 30° C., while distillation was carried out at 210° C., 240° C., and 270° C. The collected condensate was heated to 30° C. on a hot plate, manually mixed until homogenous, then moved to a glass storage container using a heat gun, providing 31.5 g of HCD.

The HCD was analyzed using reverse phase HPLC (HPLC column: Accucore C18 2.6 μm 150×4.6 mm—Thermo Scientific; mobile phases: acetonitrile+0.1% formic acid, 5 mM ammonium formate+0.1% formic acid in water), employing a mixture of cannabinoid standards for calibration; not all cannabinoids were detectable due to lack of the corresponding standards. Results of the analysis are shown in Table 2.

Additionally, CBND was isolated from HCD by the following methods:

Flash Chromatography
1. Weighed 2 g of HCD into a 20 mL scintillation vial
2. Fully dissolved HCD in 10 mL of hexanes or chloroform in low heat water bath with sonication cycle of ON/OFF of 10 s/10 s while simultaneously pipetting the mixture in and out to help the dissolution. In some cases the resulting chloroform solution was washed with saturated aqueous NaHCO$_3$.
3. Loaded the obtained HCD solution on an equilibrated 12 g flash chromatography cartridge (RediSep Rf Disposable Flash columns, 12 gram).
4. Attached cartridge to a second 12 g cartridge (24 g total) and ran in Yamazen W-PREP 2XY Flash Chromatography System:
a. Equilibration:
   i. Flow Rate: 30 mL/min
   ii. Time: 6 min
   iii. Solvents: 100% Hexane
b. Run:
   i. Flow Rate: 35 mL/min
   ii. Wavelength: 254 nm
   iii. Solvents: Ethyl Acetate (A), Hexane (B) 0-10 min: 0% B 10-30 min: 0→100% B 30-35 min: 100% B

TABLE 2

Concentrations of selected cannabinoids in hemp *Cannabis* distillate.

| Analyte | Cannabinoid | Conc. (weight %) | Conc. (mg/g) | LOQ (weight %) | LOD (weight %) |
|---|---|---|---|---|---|
| CBDVA | Cannabidivarinic acid | ND | ND | 0.10% | 0.01% |
| CBDV | Cannabidivarin | 0.4% | 3.75 | 0.10% | 0.01% |
| CBDA | Cannabidiolic acid | ND | ND | 0.10% | 0.02% |
| CBGA | Cannabigerolic acid | ND | ND | 0.10% | 0.03% |
| CBG | Cannabigerol | 0.4% | 3.51 | 0.10% | 0.03% |
| CBD | Cannabidiol | 55.9% | 558.92 | 0.10% | 0.01% |
| THCV | Tetrahydrocannabivarin | 0.3% | 2.75 | 0.10% | 0.01% |
| THCVA | Tetrahydrocannabivarinic acid | 0.2% | 1.51 | 0.10% | 0.01% |
| CBN | Cannabinol | 1.3% | 12.94 | 0.10% | 0.01% |
| CBNA | Cannabinolic acid | 0.2% | 2.37 | 0.10% | 0.01% |
| Δ9THC | Δ9-Tetrahydrocannabinol | 1.6% | 15.97 | 0.10% | 0.01% |
| Δ8THC | Δ8-Tetrahydrocannabinol | 0.3% | 3.37 | 0.10% | 0.01% |
| CBL | Cannabicyclol | 0.6% | 6.06 | 0.10% | 0.01% |
| CBC | Cannabichromene | 1.0% | 10.01 | 0.10% | 0.01% |
| THCA | Tetrahydrocannabinolic acid | ND | ND | 0.10% | 0.01% |
| CBCA | Cannabichromenic acid | ND | ND | 0.50% | 0.02% |
| CBLA | Cannabicyclolic acid | ND | ND | 0.10% | 0.01% |

Note:
ND = Not Detected;
LOQ = Limit of Quantitation;
LOD = Limit of Detection

Reverse-Phase C18 Gravity Chromatography

A glass column (20 mm diameter×300 mm length) was filled to 60% with spherical silica functionalized with polymeric C18 particle size 40-70 μm and pore size of 100 A, a small layer of sea sand was added to the top. The column was equilibrated with 300 mL 50% acetonitrile (ACN) 50% water ($H_2O$) or about 3 column volumes. The HCD sample was dissolved in chloroform then added to the top of the column. Eluted with 200 mL 50/50 ACN/$H_2O$, then 100 mL 90/10 ACN/$H_2O$, then 300 mL 100% ACN. Fractions were collected manually, concentrated, and assessed by in-tact mass spectrometry and HPLC retention time.

The flash chromatography isolation provided the following amounts of CBND:
24 mg of CBND isolated from 2.51 g of HCD (1.0%);
59 mg of CBND isolated from 3.12 g of HCD (1.9%);
70 mg isolated from 3.51 g hemp of HCD (2.0%).

Isolation by reverse-phase C18 gravity chromatography provided 40 mg of CBND isolated from 1.14 g of HCD (3.5%).

Figure 12:
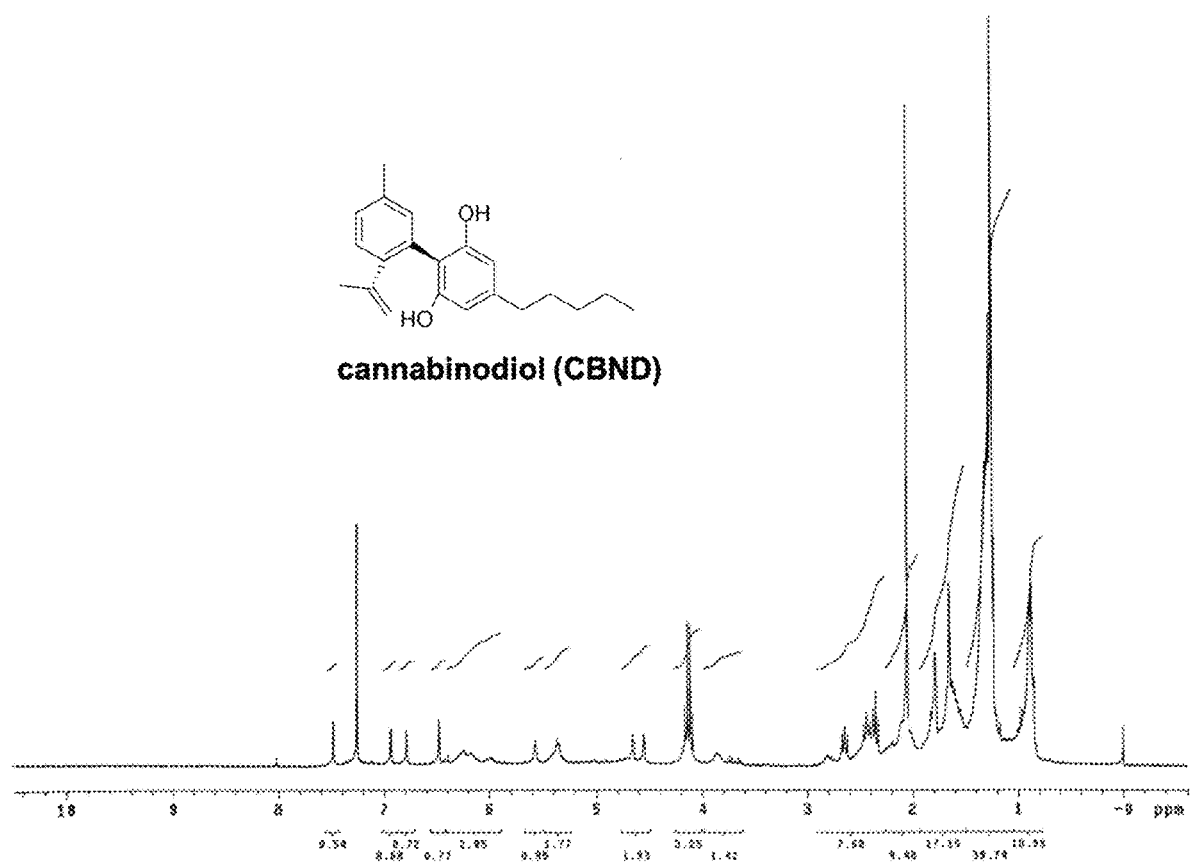
FIG. 12 is a $^1$H NMR spectrum of cannabinodiol (CBND).
Figure 13:
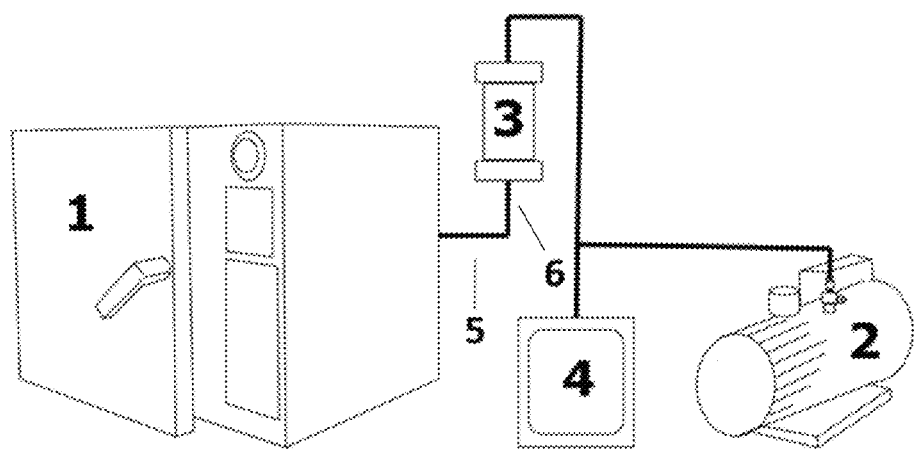
FIG. 13 is a schematic representation of the apparatus for obtaining compounds from a plant or fungus material (1—enclosure (e.g., vacuum oven) for thermal treatment of the plant or fungus material; 2—vacuum source; 3—affinity medium; 4—optional exhaust filter; 5 and 6—tubing or pipes connecting the enclosure to the affinity medium).
Figure 14:
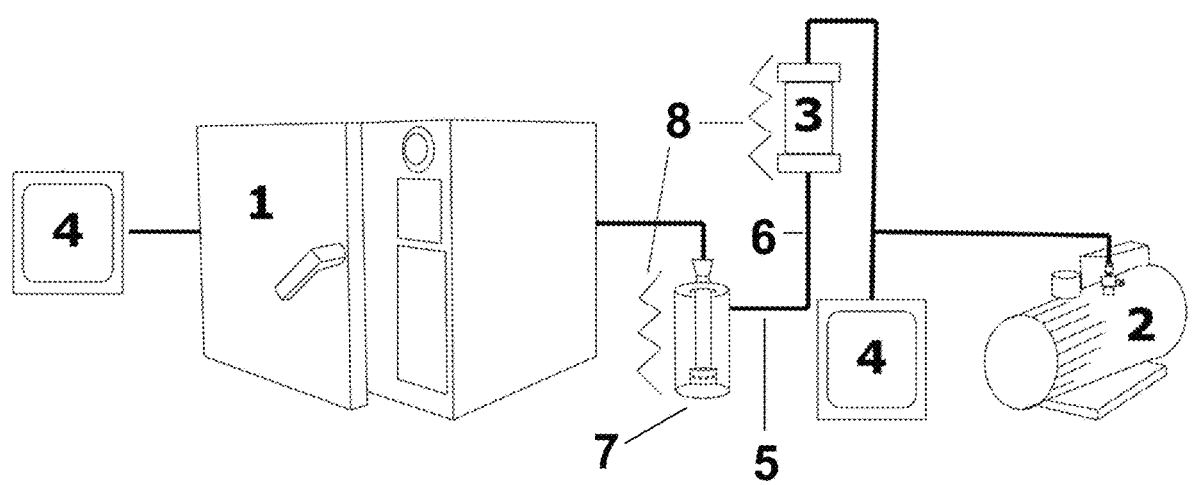
FIG. 14 is a schematic representation of the apparatus for obtaining compounds from a plant or fungus material with additional elements (as compared to FIG. 13) (1—enclosure for thermal treatment of the plant or fungus material; 2—vacuum source; 3—affinity medium; 4—optional exhaust filter; 5 and 6—tubing or pipes connecting the enclosure to the affinity medium; 7—cleaning medium; 8—heating/cooling elements).
Figure 15:
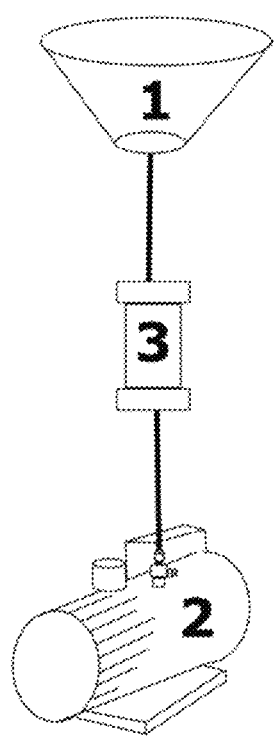
FIG. 15 is a schematic representation of the apparatus for obtaining compounds from a plant or fungus material (1—vessel for thermal treatment of the plant or fungus material; 2—vacuum source; 3—affinity medium).

The identity of the isolated CBND was further confirmed by $^1$H NMR (see FIG. 12).

Figure 10:
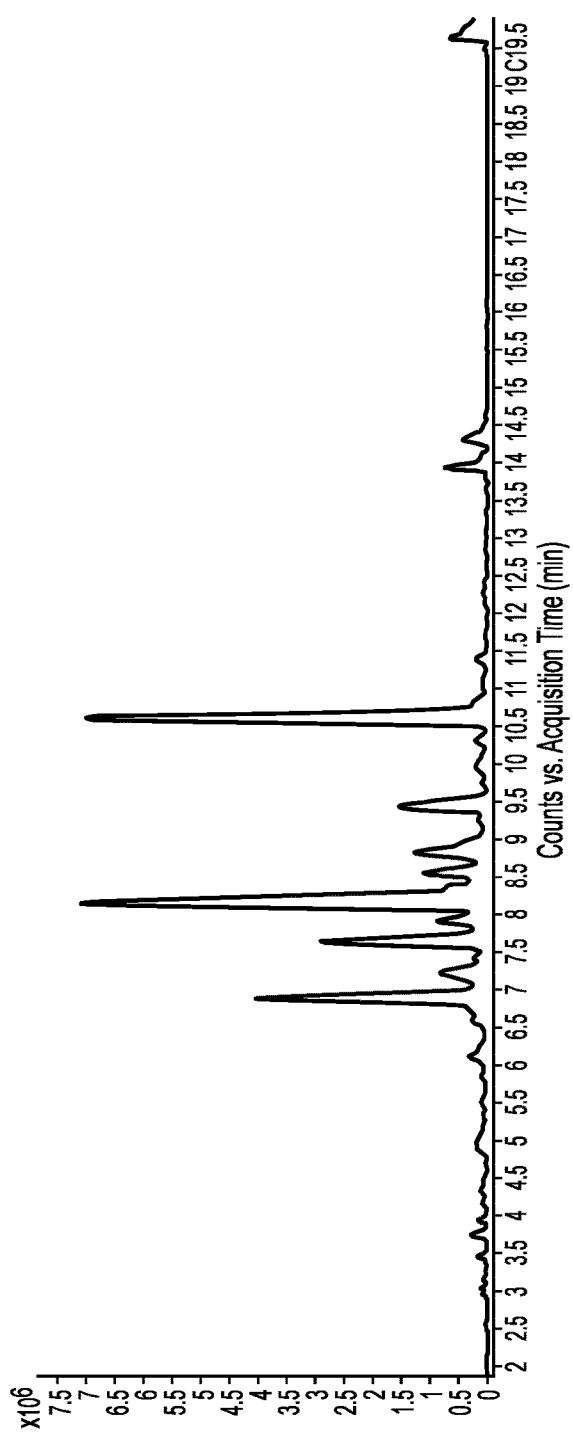
FIG. 10 is a UHPLC-HRMS/MS (ultra-high-performance liquid chromatography-high resolution mass spectrometry/mass spectrometry) total compound chromatogram in 10× diluted hemp *Cannabis* distillate in ESI+.
Figure 11:
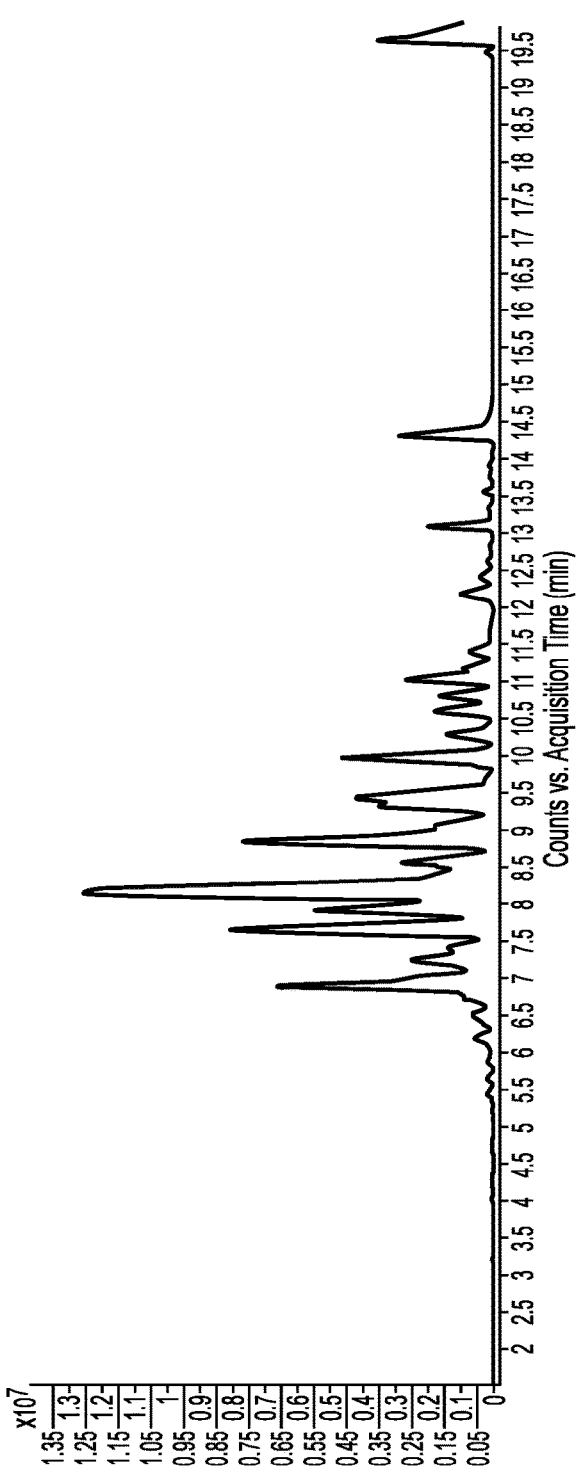
FIG. 11 is a UHPLC-HRMS/MS total compound chromatogram in 10× diluted hemp *Cannabis* distillate in ESI−.

HCD was further analyzed for the presence of rare cannabinoids. Targeted screening of 243 phytocannabinoids which molecular spectral information was performed using UHPLC-HRMS/MS(Q-TOF) method. In the ESI+ionization mode, 24 compounds (unique combination of exact mass and retention time (RT)) were detected; in the ESI-ionization mode, 54 compounds (unique combination of exact mass and retention time) were detected. The results of the UHPLC-MS/MS analysis are shown in FIGS. 10, 11, and Tables 3 and 4.

TABLE 3

Compounds in hemp Cannabis distillate as determined by UHPLC-HRMS/MS extracted ion chromatogram of 54 compounds with unique combination of exact mass and RT detected in ESI+.

| Compound number | Measured exact mass* (neutral, monoisotopical) | Estimated elemental formula** | RT*** (min) | Tentative identity (name of possible compounds)**** | Peak area |
|---|---|---|---|---|---|
| 1 | 342.2553 | C23 H34 O2 | 5.62 | (−)-trans-delta9-tetrahydrocannabiphorol/cannabidiphorol | 1.0E+05 |
| 2 | 330.2201 | C21 H30 O3 | 6.89 | 8'-Hydroxyisocannabichromene/cannabielsoin/abnormal cannabigeroquinol/10alpha-hydroxy trans delta-8-tetrahydrocannabinol/10 beta-hydroxy trans delta-8-tetrahydrocannabinol/8 alpha-hydroxy-delta9-trans-tetrahydrocannabinol/8 beta-hydroxy-delta9-trans-tetrahydrocannabinol/tetrahydrocannabinol epoxide/hydroxy delta9,11-hexahydrocannabinol | 4.7E+08 |
| 3 | 372.2297 | C23 H32 O4 | 7.43 | (+/−)-4-Acetoxycannabichromene/acetyl cannabigeroquinol/7,8-dehydro-10-O-ethylcannabitriol | 9.5E+05 |
| 4 | 330.2202 | C21 H30 O3 | 7.64 | 8'-Hydroxyisocannabichromene/cannabielsoin/abnormal cannabigeroquinol/10alpha-hydroxy trans delta-8-tetra hydrocannabinol/10 beta-hydroxy trans delta-8-tetrahydrocannabinol/8 alpha-hydroxy-delta 9-trans-tetrahydrocannabinol/8 beta-hydroxy-delta9-trans tetrahydrocannabinol/tetrahydrocannabinol epoxide/hydroxy delta9,11-hexahydrocannabinol | 8.1E+08 |
| 5 | 300.2094 | C21 H30 O3 | 7.64 | 8'-Hydroxyisocannabichromene/cannabielsoin/abnormal cannabigeroquinol/10alpha-hydroxy trans delta-8-tetrahydrocannabinol/10 beta-hydroxy trans delta-8-tetrahydrocannabinol/8 alpha-hydroxy-delta9-trans-tetrahydrocannabinol/8 beta-hydroxy-delta9-trans-tetrahydrocannabinol/tetrahydrocannabinol epoxide/hydroxy delta9,11-hexahydrocannabinol | 8.1E+08 |
| 6 | 332.199 | C20 H28 O2 | 7.70 | delta-9-Tetrahydrocannabinol-C4/norCannabidiol | 2.9E+06 |
| 7 | 332.2346 | C20 H28 O4 | 8.05 | Cannabichromanone/cannabigerovarinic acid | 2.6E+06 |
| 8 | 258.1619 | C21 H32 O3 | 8.13 | rac-6'-Epoxycannabigerol(2'S*.3'R*)/rac-6'-epoxycannabigerol(2'R*.3'R*)/(−)-7-Hydroxycannabichromane | 4.0E+05 |
| 9 | 346.2143 | C17 H22 O2 | 8.14 | Cannabidiorcol/delta-9-trans-tetrahydrocannabiorcol/cannabiorcitran/cannabiorcicyclol/cannabiorcichromene | 3.1E+06 |

TABLE 3-continued

Compounds in hemp Cannabis distillate as determined by UHPLC-HRMS/MS extracted ion chromatogram of 54 compounds with unique combination of exact mass and RT detected in ESI+.

| Compound number | Measured exact mass* (neutral, monoisotopical) | Estimated elemental formula** | RT*** (min) | Tentative identity (name of possible compounds)**** | Peak area |
|---|---|---|---|---|---|
| 10 | 372.231 | C21 H30 O4 | 8.75 | Trans-10-ethoxy-9-hydroxy-delta6a(10a)-tetrahydrocannabivarin-C3/cannabimovone/(+)-(9S.10S)-trans-cannabitriol/(−)-(9R.10R)-trans-cannabitriol/(9S.10R)-cis-cannabitriol/(9R.10S)-cis-cannabitriol/ethoxy-cannabitriolvarin/isocannabitriol(8.9-dihydroxy-delta-6a(10a)-tetrahydrocannabinol) | 4.8E+05 |
| 11 | 300.2088 | C23 H32 O4 | 8.77 | (+/−)-4-Acetoxycannabichromene/acetyl cannabigeroquinol/7.8-dehydro-10-O-ethylcannabitriol | 7.2E+06 |
| 12 | 286.1934 | C20 H28 O2 | 8.92 | delta-9-Tetrahydrocannabinol-C4/norCannabidiol | 1.3E+07 |
| 13 | 314.2246 | C19 H26 O2 | 9.17 | delta7-Trans-Isotetrahydrocannabivarin-C3/(1aS.3aR.8bR.8cR)-cannabicyclovarin/cannabivarichromene/2-methyl-2-(4-methyl-2-pentenyl)-7-propyl-2H-1-benzopyran-5-ol/delta7-1.2-cis-(1R.3R.6S)-isotetrahydrocannabivarin-C3/delta7-1.2-cis-(1S. 3S.6R)-Isotetrahydrocannabivarin-C3/delta9-cis-Tetrahydrocannabidivarin | 1.6E+06 |
| 14 | C20 H28 O2 | 300.2091 | 9.91 | delta-9-Tetrahydrocannabinol-C4/norCannabidiol | 1.3E+06 |
| 15 | C21 H28 O4 | 344.1985 | 10.30 | 10-Hydroxy-9-oxo-delta-8-tetrahydrocannabinol/delta-9-tetrahydrocannabinolic acid-C4 A/delta-9-tetrahydrocannabinolic acid-C4 B | 6.3E+05 |
| 16 | C22 H34 O2 | 330.2562 | 10.32 | O-Methylcannabigerol | 3.2E+06 |
| 17 | C17 H22 O2 | 258.1622 | 10.61 | Cannabidiorcol/delta-9-trans-tetrahydrocannabiorcol/cannabiorcitran/cannabiorcicyclol/cannabiorcichromene | 1.4E+06 |
| 18 | C21 H30 O2 | 314.2254 | 10.62 | (1aS.3aR.8bR.8cR)-Cannabicyclol/cannabicitran/(−)-delta9-cis-(6aS.10aR)-delta9-tetrahydrocannabinol/(â¨)-delta7-trans-(1R.3R.6R)-isoletrahydrocannabinol-C5/cannabigeroquinone | 1.3E+09 |
| 19 | C19 H20 O3 | 296.1412 | 10.86 | Trans-arachidin-2/arachidin-3/radulanin A/chiricanine B | 1.5E+05 |
| 20 | C21 H30 O3 | 330.2195 | 11.10 | 8'-Hydroxyisocannabichromene/cannabielsoin/abnormal cannabigeroquinol/10alpha-hydroxy trans delta-8-tetrahydrocannabinol/10 beta-hydroxy trans delta-8-tetrahydrocannabinol/8 alpha-hydroxy-delta9-trans-tetrahydrocannabinol/8 beta-hydroxy-delta9-trans-tetrahydrocannabinol/tetrahydrocannabinol epoxide/hydroxy delta9.11-hexahydrocannabinol | 5.1E+05 |
| 21 | C23 H34 O2 | 342.2557 | 11.92 | (−)-trans-Î"9-tetrahydrocannabiphorol/cannabidiphorol | 5.7E+05 |
| 22 | C24 H28 O2 | 348.2086 | 12.23 | Amorphastylbol/machaeridiol A/perrotteninen(e)/machaeriol A | 4.4E+05 |
| 23 | C22 H32 O2 | 328.2399 | 12.30 | O-Methylcannabidiol | 1.3E+06 |
| 24 | C43 H60 O4 | 640.4494 | 13.20 | Cannabisol | 2.4E+05 |

*Mass error compared the theoretical exact mass <5 ppm
**Match of isotopic pattern confirmed
***Retention time
****Tentative identification of compounds based on available scientific articles (Hanuš et al. 2016, Mechoulam 2002)

TABLE 4

Compounds in hemp Cannabis distillate as determined by UHPLC-HRMS/MS extracted ion chromatogram of 54 compounds with unique combination of exact mass and RT detected in ESI-.

| Compound number | Measured exact mass* (neutral, monoisotopical) | Estimated elemental formula** | RT*** (min) | Tentative identity (name of possible compounds)**** | Peak area |
|---|---|---|---|---|---|
| 1 | 302.1880 | C19 H26 O3 | 6.09 | C3-Cannabielsoin | 2.9E+06 |
| 2 | 288.2085 | C19 H28 O2 | 6.18 | Cannabigerovarin | 4.5E+05 |
| 3 | 348.2295 | C21 H32 O4 | 6.18 | Cannabiripsol | 5.8E+05 |
| 4 | 332.2351 | C21 H32 O3 | 6.38 | rac-6'-Epoxycannabigerol(2'S*.3'R*)/rac-6'-epoxycannabigerol(2'R*.3'R*)/(−)-7-Hydroxycannabichromane | 3.9E+06 |
| 5 | 288.2091 | C19 H28 O2 | 6.42 | Cannabigerovarin | 1.5E+06 |
| 6 | 258.1623 | C17 H22 O2 | 6.54 | Cannabidiorcol/delta-9-trans-tetrahydrocannabiorcol/cannabiorcitran/cannabiorcicyclol/cannabiorcichromene | 9.5E+06 |
| 7 | 374.2445 | C23 H34 O4 | 6.68 | (−)-(9R.10R)-trans-10-O-Ethylcannabitriol/5-acetyl-4-hydroxycannabigerol/acetyl abnormal cannabigeroquinol/cannabigerolic acid monomethylether | 8.7E+05 |
| 8 | 304.1680 | C18 H24 O4 | 6.69 | Cannabichromanone-C3 | 6.1E+06 |
| 9 | 330.2202 | C21 H30 O3 | 6.74 | 8'-Hydroxyisocannabichromene/cannabielsoin/abnormal cannabigeroquinol/10alpha-hydroxy trans delta-8-tetrahydrocannabinol/10 beta-hydroxy trans delta-8-tetrahydrocannabinol/8 alpha-hydroxy-delta9-trans-tetrahydrocannabinol/8 beta-hydroxy-delta9-trans-tetrahydrocannabinol/tetrahydrocannabinol epoxide/hydroxy delta9.11-hexahydrocannabinol | 1.5E+07 |
| 10 | 332.1989 | C20 H28 O4 | 6.76 | Cannabichromanone/cannabigerovarinic acid | 3.3E+06 |
| 11 | 330.2199 | C21 H30 O3 | 6.88 | 8'-Hydroxyisocannabichromene/cannabielsoin/abnormal cannabigeroquinol/10alpha-hydroxy trans delta-8-tetrahydrocannabinol/10 beta-hydroxy trans delta-8-tetrahydrocannabinol/8 alpha-hydroxy-delta9-trans-tetrahydrocannabinol/8 beta-hydroxy-delta9-trans-tetrahydrocannabinol/tetrahydrocannabinol epoxide/hydroxy delta9.11-hexahydrocannabinol | 7.3E+08 |
| 12 | 348.2292 | C21 H32 O4 | 6.99 | Cannabiripsol | 1.1E+06 |
| 13 | 360.1939 | C21 H28 O5 | 7.08 | Cannabichromanone-C | 5.6E+06 |
| 14 | 332.2355 | C21 H32 O3 | 7.15 | rac-6'-Epoxycannabigerol(2'S*.3'R*)/rac-6'-epoxycannabigerol(2'R*.3'R*)/(−)-7-Hydroxycannabichromane | 2.4E+07 |
| 15 | 296.1411 | C19 H20 O3 | 7.21 | Trans-arachidin-2/arachidin-3/radulanin A/chiricanine B | 1.7E+06 |
| 16 | 316.2394 | C21 H32 O2 | 7.27 | Cannabinerol/abnormal cannabigerol/hexahydrocannabinol | 4.9E+05 |
| 17 | 332.2351 | C21 H32 O3 | 7.33 | rac-6'-Epoxycannabigerol(2'S*.3'R*)/rac-6'-epoxycannabigerol(2'R*.3'R*)/(−)-7-Hydroxycannabichromane | 9.5E+05 |
| 18 | 324.2086 | C22 H28 O2 | 7.39 | o-methylcannabinol | 4.1E+07 |
| 19 | 314.2249 | C21 H30 O2 | 7.40 | (1aS.3aR.8bR.8cR)-Cannabicyclol/cannabicitran/(−)-delta9-cis-(6aS.10aR)-delta9-tetrahydrocannabinol/(ã¨)-delta7-trans-(1R.3R.6R)-isotetrahydrocannabinol-C5/cannabigeroquinone | 3.5E+07 |

TABLE 4-continued

Compounds in hemp Cannabis distillate as determined by UHPLC-HRMS/MS extracted ion chromatogram of 54 compounds with unique combination of exact mass and RT detected in ESI-.

| Compound number | Measured exact mass* (neutral, monoisotopical) | Estimated elemental formula** | RT*** (min) | Tentative identity (name of possible compounds)**** | Peak area |
|---|---|---|---|---|---|
| 20 | 300.2094 | C20 H28 O2 | 7.70 | delta-9-Tetrahydrocannabinol-C4/norCannabidiol | 7.5E+06 |
| 21 | 282.1620 | C19 H22 O2 | 7.73 | Cannabinodivarin/cannabivarin/demethyldecarboxyamorfrutin A/63b/63c | 3.8E+06 |
| 22 | 366.2193 | C24 H30 O3 | 7.76 | Hydroxy helicannabigenol/55 | 1.1E+07 |
| 23 | 330.2203 | C21 H30 O3 | 7.92 | 8'-Hydroxyisocannabichromene/cannabielsoin/abnormal cannabigeroquinol/10alpha-hydroxy trans delta-8-tetrahydrocannabinol/10 beta-hydroxy trans delta-8-tetrahydrocannabinol/8 alpha-hydroxy-delta9-trans-tetrahydrocannabinol/8 beta-hydroxy-delta9-trans-tetrahydrocannabinol/tetrahydrocannabinol epoxide/hydroxy delta9.11-hexahydrocannabinol | 6.2E+08 |
| 24 | 360.1935 | C21 H28 O5 | 7.93 | Cannabichromanone-C | 1.2E+06 |
| 25 | 308.1777 | C21 H24 O2 | 8.00 | Dehydrocannabifuran | 3.3E+06 |
| 26 | 352.2399 | C24 H32 O2 | 8.08 | O-Propylcannabinol | 1.3E+06 |
| 27 | 346.2134 | C21 H30 O4 | 8.17 | Trans-10-ethoxy-9-hydroxy-delta6a(10a)-tetrahydrocannabivarin-C3/cannabimovone/(+)-(9S.10S)-trans-cannabitriol/(−)-(9R.10R)-trans-cannabitriol/(9S.10R)-cis-cannabitriol/(9R.10S)-cis-cannabitriol/ethoxy-cannabitriolvarin/isocannabitriol (8.9-dihydroxy-delta-6a(10a)-tetrahydrocannabinol) | 3.8E+07 |
| 28 | 332.2352 | C21 H32 O3 | 8.43 | rac-6'-Epoxycannabigerol(2'S*.3'R*)/rac-6'-epoxycannabigerol(2'R*.3'R*)/(−)-7-Hydroxycannabichromane | 3.9E+06 |
| 29 | 374.2454 | C23 H34 O4 | 8.67 | (−)-(9R.10R)-trans-10-O-Ethylcannabitriol/5-acetyl-4-hydroxycannabigerol/acetyl abnormal cannabigeroquinol/cannabigerolic acid monomethylether | 8.9E+05 |
| 30 | 286.1929 | C19 H26 O2 | 8.75 | delta7-Trans-Isotetrahydrocannabivarin-C3/(1aS.3aR.8bR.8cR)-cannabicyclovarin/cannabivarichromene/2-methyl-2-(4-methyl-2-pentenyl)-7-propyl-2H-1-benzopyran-5-ol/delta7-1.2-cis-(1R.3R.6S)-isotetrahydrocannabivarin-C3/delta7-1.2-cis-(1S.3S.6R)-Isotetrahydrocannabivarin-C3/delta9-cis-Tetrahydrocannabidivarin | 1.9E+06 |
| 31 | 280.1464 | C19 H20 O2 | 8.83 | Chiricanin A/araphyn-1/63k/68 | 3.2E+06 |
| 32 | 296.1776 | C20 H24 O2 | 8.86 | Cannabinol-C4/decarboxyamorfrutin A/82 | 1.3E+07 |
| 33 | 268.1461 | C18 H20 O2 | 8.89 | Cannabinol-C2/56a/63a | 8.4E+07 |
| 34 | 300.2083 | C20 H28 O2 | 8.91 | delta-9-Tetrahydrocannabinol-C4/norCannabidiol | 8.0E+06 |
| 35 | 380.2710 | C26 H36 O2 | 8.93 | O-Pentylcannabinol | 7.1E+05 |
| 36 | 316.2392 | C21 H32 O2 | 8.94 | Cannabinerol/abnormal cannabigerol/hexahydrocannabinol | 4.5E+06 |
| 37 | 284.1410 | C18 H20 O3 | 9.04 | 63h | 1.4E+06 |
| 38 | 342.2194 | C22 H30 O3 | 9.07 | Ferruginene C/2-formyl-delta9-trans-tetrahydrocannabinol | 1.2E+08 |
| 39 | 328.2039 | C21 H28 O3 | 9.10 | Cannabichromanone-D/cannabicoumaronone/10-oxo-delta-6a(10a)-tetrahydrocannabinol/8-Oxo-delta9-trans-tetrahydrocannabinol/9.10-Anhydrocannabitriol/anhydrocannabimovone | 7.3E+07 |
| 40 | 308.1778 | C21 H24 O2 | 9.21 | Dehydrocannabifuran | 6.5E+06 |
| 41 | 342.2549 | C23 H34 O2 | 9.21 | (−)-trans-Δ"9-tetrahydrocannabiphorol/cannabidiphorol | 3.4E+06 |

TABLE 4-continued

Compounds in hemp Cannabis distillate as determined by UHPLC-HRMS/MS extracted ion chromatogram of 54 compounds with unique combination of exact mass and RT detected in ESI-.

| Compound number | Measured exact mass* (neutral, monoisotopical) | Estimated elemental formula** | RT*** (min) | Tentative identity (name of possible compounds)**** | Peak area |
|---|---|---|---|---|---|
| 42 | 330.2550 | C22 H34 O2 | 9.40 | O-Methylcannabigerol | 3.2E+06 |
| 43 | 282.1618 | C19 H22 O2 | 9.51 | Cannabinodivarin/cannabivarin/demethyldecarboxyamorfrutin A/63b/63c | 2.3E+06 |
| 44 | 330.2193 | C21 H30 O3 | 9.61 | 8'-Hydroxyisocannabichromene/cannabielsoin/abnormal cannabigeroquinol/10alpha-hydroxy trans delta-8-tetrahydrocannabinol/10 beta-hydroxy trans delta-8-tetrahydrocannabinol/8 alpha-hydroxy-delta9-trans-tetrahydrocannabinol/8 beta-hydroxy-delta9-trans-tetrahydrocannabinol/tetrahydrocannabinol epoxide/hydroxy delta9.11-hexahydrocannabinol | 5.6E+05 |
| 45 | 342.2186 | C22 H30 O3 | 9.98 | Ferruginene C/2-formyl-delta9-trans-tetrahydrocannabinol | 5.3E+06 |
| 46 | 310.1938 | C21 H26 O2 | 10.23 | Cannabinodiol/cannabifuran | 1.2E+07 |
| 47 | 352.2394 | C24 H32 O2 | 10.55 | O-Propylcannabinol | 4.4E+06 |
| 48 | 268.1463 | C18 H20 O2 | 10.61 | Cannabinol-C2/56a/63a | 1.5E+06 |
| 49 | 310.1936 | C21 H26 O2 | 10.81 | Cannabinodiol/cannabifuran | 1.6E+08 |
| 50 | 308.1779 | C21 H24 O2 | 11.41 | Dehydrocannabifuran | 6.6E+07 |
| 51 | 640.4484 | C43 H60 O4 | 12.14 | Cannabisol | 2.4E+07 |
| 52 | 342.2182 | C22 H30 O3 | 13.18 | Ferruginene C/2-formyl-delta9-trans-tetrahydrocannabinol | 4.0E+05 |
| 53 | 268.1464 | C18 H20 O2 | 13.27 | Cannabinol-C2/56a/63a | 8.5E+05 |
| 54 | 640.4481 | C43 H60 O4 | 13.32 | Cannabisol | 6.6E+05 |

*Mass error compared the theoretical exact mass < 5 ppm
**Match of isotopic pattern confirmed
***Retention time
****Tentative identification of compounds based on available scientific articles (Hanuš et al. 2016, Mechoulam 2002)

The data in Tables 3 and 4 confirm the presence of rare cannabinoinds in HCD: o-methylcannabidiol is listed in Table 3, compound number 23; o-methylcannabinol is listed in Table 4, compound 18; o-propylcannabinol is listed in Table 4, compound 26; and o-pentylcannabinol is listed in Table 4, compound 35. Compounds in Table 4, lines 46 and 49 are identified as either cannabinodiol (CBND) or its isomer cannabifuran. In addition to this analysis, the presence of CBND was independently confirmed by $^1$H NMR of an isolated fraction (FIG. 12).

Example 9. Isolation and Analysis of Cannabinoid-Containing Composition from Medical *Cannabis*

Procedure I. Dried biomass medical *Cannabis* (5-8% THC w/w, Temescal Wellness, MA USA) was ground in a stainless steel blender to particle size of less than 10 mm, then 498 g of the ground material was loaded onto 5 trays. The trays were placed in a pre-heated vacuum oven (Across International, NJ USA) at 93-148° C. (200-300° F.) at atmospheric pressure with both vacuum and inlet ports completely open. The filter system was attached to the oven at the vacuum port at a 90° angle from the port, facing upwards. The affinity filter consisted of three filter layers—the first layer, a 635 (20 micron) stainless steel mesh filter, the second layer, an affinity medium including capture material functionalized for affinity to the desired products, and the third layer, a further 635 (20 micron) mesh stainless steel filter. The third layer was used here for structural support of the affinity medium (polymeric spherical silica gel functionalized with C18, 40-75 μm particle sizes, 100 Å pore size, SiliCycle QC, CAN). The opposing end of the filter system was attached to the vacuum pump. The vacuum pump attached inline to the system was turned on at full power. The system was allowed to run for 3 hrs at steady state with the flow rate of air 1.04 L/s before turning off the vacuum pump and oven.

The filter system was detached from the vacuum pump and the oven. 50 mL of ethanol was added to the connection pipe attached to the vacuum port of the oven to solubilize the first fraction condensed by adiabatic expansion. The first fraction was collected by removing the connection pipe and allowing the solubilized extract to flow into a glass beaker. The filter system was attached to a 1.5 L filter flask and diaphragm pump. 200 mL of ethanol were added to the filter system while it was closed, manually mixed, then incubated. This process was repeated once more with 200 mL and one final time with 100 mL. The combined eluted fractions were placed in a 1 L glass round bottom flask. Ethanol was removed by rotary evaporation and the resulting affinity fraction was added to the first fraction to give 6 g of medical *Cannabis* extract.

The medical *Cannabis* extract was analyzed using reverse phase HPLC (HPLC column: Accucore C18 2.6 μm 150×4.6 mm—Thermo Scientific; mobile phases: acetonitrile+0.1% formic acid, 5 mM ammonium formate+0.1% formic acid in water), employing a mixture of cannabinoid standards for calibration; not all cannabinoids were detectable due to lack of the corresponding standards. Results of the analysis are shown in Table 5.

TABLE 5

Concentrations of selected cannabinoids in medical Cannabis extract.

| Analyte | Cannabinoid | Conc. (wt. %) | Conc. (mg/g) | LOQ (wt. %) | LOD (wt. %) |
|---|---|---|---|---|---|
| CBDVA | Cannabidivarinic acid | 0.1% | 1.0 | 0.10% | 0.01% |
| CBDV | Cannabidivarin | ND | ND | 0.10% | 0.02% |
| CBDA | Cannabidiolic acid | ND | ND | 0.10% | 0.02% |
| CBGA | Cannabigerolic acid | 0.3% | 3.0 | 0.10% | 0.02% |
| CBG | Cannabigerol | 0.5% | 5.0 | 0.10% | 0.04% |
| CBD | Cannabidiol | 0.4% | 4.0 | 0.10% | 0.03% |
| THCV | Tetrahydrocannabivarin | 0.1% | 1.0 | 0.10% | 0.01% |
| THCVA | Tetrahydrocannabivarinic | ND | ND | 0.10% | 0.03% |
| CBCV | Cannabichromevarin | ND | ND | 0.10% | 0.01% |
| CBN | Cannabinol | 19.2% | 192.0 | 0.10% | 0.01% |
| CBNA | Cannabinolic acid | ND | ND | 0.10% | 0.01% |
| Δ9THC | Δ9-Tetrahydrocannabinol | 9.8% | 98.0 | 0.10% | 0.02% |
| Δ8THC | Δ8-Tetrahydrocannabinol | 0.3% | 3.0 | 0.10% | 0.02% |
| CBL | Cannabicyclol | ND | ND | 0.10% | 0.02% |
| THCA | Tetrahydrocannabinolic acid | ND | ND | 0.10% | 0.01% |
| CBC | Cannabichromene | 0.3% | 3.0 | 0.10% | 0.01% |
| CBCA | Cannabichromenic acid | ND | ND | 0.50% | 0.05% |
| CBLA | Cannabicyclolic acid | ND | ND | 0.10% | 0.01% |
| CBT | Cannabicitran | 0.6% | 6.0 | 0.10% | 0.02% |

Note:
ND = Not Detected;
LOQ = Limit of Quantitation;
LOD = Limit of Detection

Procedure II. Dried biomass from medical *Cannabis* (5-8% THC w/w, Temescal Wellness, MA USA) was ground in a stainless steel blender to particle size of less than 10 mm, then 493 g of the ground material was loaded onto 5 trays. The trays were placed in a pre-heated vacuum oven (Across International, NJ USA) at 213° C. (425° F.) at atmospheric pressure with both vacuum and inlet ports completely open. The filter system was attached to the oven at the vacuum port at a 90° angle from the port, facing upwards. The affinity filter consisted of three filter layers—the first layer, a 635 (20 micron) stainless steel mesh filter, the second layer, an affinity medium including capture material functionalized for affinity to the desired products, and the third layer, a further 635 (20 micron) mesh stainless steel filter. The third layer was used here for structural support of the affinity medium (polymeric spherical silica gel functionalized with C18, 40-75 μm particle sizes, 100 Å pore size, SiliCycle QC, CAN). The opposing end of the filter system was attached to the vacuum pump. The vacuum pump attached inline to the system was turned on at full power. The system was allowed to run for 1 hr at steady state with the flow rate of air 1.04 L/s.

The filter system was detached from the vacuum pump and the oven. The elute was collected and the solvent was removed as described above in Procedure I above, resulting in 47 g of medical *Cannabis* extract.

Medical *Cannabis* extract was loaded into a 1 L round bottom 2-neck round bottom boiling flask. Vacuum distillation was carried out as described in Example 8 to give 13 g of medical *Cannabis* distillate (MCD). The distillate was analyzed using reverse phase HPLC (HPLC column: Accucore C18 2.6 μm 150×4.6 mm—Thermo Scientific; mobile phases: acetonitrile+0.1% formic acid, 5 mM ammonium formate+0.1% formic acid in water), employing a mixture of cannabinoid standards for calibration; not all cannabinoids were detectable due to lack of the corresponding standards. Results of the analysis are shown in Table 6.

TABLE 6

Concentrations of selected cannabinoids in medical Cannabis distillate.

| Analyte | Cannabinoid | Conc. (wt. %) | Conc. (mg/g) | LOQ (wt. %) | LOD (wt. %) |
|---|---|---|---|---|---|
| CBDVA | Cannabidivarinic acid | 0.2% | 2.0 | 0.10% | 0.01% |
| CBDV | Cannabidivarin | ND | ND | 0.10% | 0.02% |
| CBDA | Cannabidiolic acid | ND | ND | 0.10% | 0.02% |
| CBGA | Cannabigerolic acid | 0.4% | 4.0 | 0.10% | 0.02% |
| CBG | Cannabigerol | 0.4% | 4.0 | 0.10% | 0.04% |
| CBD | Cannabidiol | ND | ND | 0.10% | 0.03% |
| THCV | Tetrahydrocannabivarin | ND | ND | 0.10% | 0.01% |
| THCVA | Tetrahydrocannabivarinic acid | ND | ND | 0.10% | 0.03% |
| CBCV | Cannabichromevarin | ND | ND | 0.10% | 0.01% |
| CBN | Cannabinol | 28.5% | 285.0 | 0.10% | 0.01% |
| CBNA | Cannabinolic acid | ND | ND | 0.10% | 0.01% |
| Δ9THC | Δ9-Tetrahydrocannabinol | 6.2% | 62.0 | 0.10% | 0.02% |
| Δ8THC | Δ8-Tetrahydrocannabinol | 1.0% | 10.0 | 0.10% | 0.02% |
| CBL | Cannabicyclol | ND | ND | 0.10% | 0.02% |
| THCA | Tetrahydrocannabinolic acid | ND | ND | 0.10% | 0.01% |

TABLE 6-continued

Concentrations of selected cannabinoids in medical Cannabis distillate.

| Analyte | Cannabinoid | Conc. (wt. %) | Conc. (mg/g) | LOQ (wt. %) | LOD (wt. %) |
|---|---|---|---|---|---|
| CBC | Cannabichromene | ND | ND | 0.10% | 0.01% |
| CBCA | Cannabichromenic acid | ND | ND | 0.50% | 0.05% |
| CBLA | Cannabicyclolic acid | ND | ND | 0.10% | 0.01% |
| CBT | Cannabicitran | 0.5% | 5.0 | 0.10% | 0.02% |

Note:
ND = Not Detected;
LOQ = Limit of Quantitation;
LOD = Limit of Detection

MCD was further analyzed by HPLC-UV by Nova Analytics at Portland, Me. (reverse phase HPLC; HPLC column: Accucore C18 2.6 µm 150×4.6 mm—Thermo Scientific; mobile phases: acetonitrile+0.1% formic acid, 5 mM ammonium formate+0.1% formic acid in water, employing a mixture of cannabinoid standards for calibration; not all cannabinoids were detectable due to lack of the corresponding standards). The following components were detected at concentrations over 2 wt. %: CBN—24.7%; Δ9THC—6.97%; Δ10THC—2.99%; and exo-THC—2.33% (LOD 1250 µg/g; LOQ 6240 µg/g).

Example 10. Extraction of Hemp *Cannabis* Using Hexane

Dried flower and biomass from hemp *Cannabis* (12% CBD w/w, Twin Arch Farms, NY USA) was ground in a stainless steel blender to fine particle size of less than 5 mm, then 215 g of the ground hemp *Cannabis* were placed in a glass bottle. About 2 L of hexane at room temperature was added to the ground hemp *Cannabis*, and the resulting suspension solution was incubated while shaking for 1 hr. The suspension was filtered through 20 µm paper filter and winterized at −20° C. for 1 hr. The hexane was removed through rotary evaporation and the resulting extract was distilled using short path distillation.

The distillation process was performed using a short path distillation unit under full vacuum. The boiling flask was heated by an electric heating jacket. The cooling jacket temperature was initially set to room temperature while distillation was carried out at 100° C., 125° C., 150° C., 175° C., and 200° C. The condensate collected at these temperatures was discarded. The cooling jacket temperature was increased to 30° C. while distillation was carried out at 210° C., 240° C., and 270° C. The collected condensate was heated to 30° C. on a hot plate, manually mixed until homogenous, then moved to a glass storage container using a heat gun.

Example 11. Isolation of Cannabinoid-Containing Compositions from Hemp *Cannabis* Under Different Conditions The process for obtaining hemp *Cannabis* isolate as described in Example 8 was performed while varying a number of parameters: the temperature and pressure of the vacuum oven and the duration of the thermal treatment. The examined conditions are summarized in Table 7.

TABLE 7

Parameters in the process of producing the hemp Cannabis isolate.

| Entry | Temp (° F.) | Pressure (mm Hg) | Time (min) | Starting Material (g) |
|---|---|---|---|---|
| 1 | 250 | 160 | 360 | 120 |
| 2 | 300 | 160 | 120 | 120 |
| 3 | 350 | 160/760 45 min/15 min cycle | 120 | 121 |
| 4 | 375 | 360 | 210 | 229.56 |
| 5 | 375 | 360/760 45 min/15 min cycle | 120 | 455.11 |
| 6 | 400 | 760 | 120 | 228.5 |
| 7 | 400 | 360/760 45 min/15 min cycle | 180 | 435 |
| 8 | 420 | 160/760 35 min/10 min cycle | 90 | 54.38 |
| 9 | 420 | 760 | 60 | 450 |
| 10 | 375,400,425 | 360 | 210 | 216.92 |
| 11 | 400,450,480 | 360 | 210 | 222.01 |

CBD-containing compositions were isolated under all tested conditions. The protocol in entry 9 provided the highest yield of the hemp *Cannabis* isolate, while the protocol in entry 8 yielded hemp *Cannabis* isolate with the highest concentration of CBD. The protocol in entry 6 afforded the best overall combination of the total yield and CBD concentration. Yield of the cannabinoid compounds can vary depending on ambient humidity.

Example 12. Molecular Docking of Cannabinoid Ligands to Endocannabinoid Targets Molecular docking is an in silico method that predicts the affinity of a ligand to a protein based upon the total energy of the bound ligand-protein complex. The molecular docking calculations utilized SwissDock, a modified version of docking software EADock DSS. Briefly, SwissDock generates binding modes/shapes for the ligand while the protein target remains rigid, the energies are estimated using the CHARMM (Chemistry at HARvard Macromolecular Mechanics) forcefield, favorable positions are further adjusted using FACTS (Fast Analytical Continuum Treatment of Solvation) meaning the positions are optimized solvated vs. in a vacuum, and final poses are grouped together in "clusters." All ligands were cleaned, hydrogens added for pH 7.4, and minimized using Universal Force Field.

The data obtained from SwissDock was visualized using UCSF Chimera (1). Clusters were analyzed by two parameters: binding stability (ΔG) and distance from known binding pocket. The distance from the known binding pocket was evaluated by the distance from the closest non-hydrogen atom in the ligand to the reference amino acid residues for each ECS target, respectively.

For CB1R and CB2R receptors the tryptophan residue in the "toggle switch" activation mechanism was used as reference. For CB1R, the reference amino acid residue was W356 (nitrogen atom; TRP 356 NE1). For CB2R, the reference amino acid residue was W258 (nitrogen atom; TRP 258 NE1).

All enzymes evaluated are part of the serine hydrolase superfamily which have highly conserved secondary structure motifs, His-Asp-Ser triads, and an easily identifiable GXSXG catalytic serine motifs. For MGL, the reference amino acid residue was S122 (oxygen atom; SER 122 OG). For FAAH, the reference amino acid residue was S241 (oxygen atom; SER 241 OG). For ABHD6, the reference amino acid residue was S148 (oxygen atom; SER 148 OG).

Example 13. Survey of Volunteers after Consumption of Hemp *Cannabis* Distillate (HCD) and Medical *Cannabis* Distillate (MCD)

Volunteers provided True, False, or Neutral reactions to the following set of statements regarding their experience after consumption of HCD or MCD.

Statements:
1: The experience was different than other edible *Cannabis* products.
2: The distillate made me feel calm.
3: The distillate made me feel sleepy.
4: The distillate made me feel high (psychoactive effect).
5: I liked the taste of the distillate.
6: I would take the distillate again.
7: I found the distillate interesting.

| Statement | True | Neutral | False |
|---|---|---|---|
| 1 | 9 | 1 | 0 |
| 2 | 10 | 0 | 0 |
| 3 | 4 | 2 | 4 |
| 4 | 5 | 3 | 2 |
| 5 | 5 | 1 | 4 |
| 6 | 9 | 1 | 0 |
| 7 | 0 | 0 | 0 |

| Statement | True | Neutral | False |
|---|---|---|---|
| 1 | 10 | 2 | 1 |
| 2 | 11 | 1 | 0 |
| 3 | 6 | 2 | 4 |
| 4 | 7 | 2 | 3 |
| 5 | 5 | 4 | 3 |
| 6 | 12 | 0 | 0 |
| 7 | 12 | 0 | 0 |

Example 14. Human Trial of MCD

MCD prepared according to Procedure II as described in Example 9 was formulated for a human trial. 600 mg of the MCD was weighed into a 100 mL glass beaker. 40 mL of extra virgin olive oil was added and the sample was stirred while heated on a hot plate to 34° C. Once the sample had fully dissolved, it was loaded into 4 separate 15 mL glass dropper bottles, providing four 10 mL samples with concentration of 15 mg/mL of total MCD with the following cannabinoid content:

| Cannabinoid | Weight/Package | Weight/Serving (1 mL) |
|---|---|---|
| CBN | 43.5 mg | 4.35 mg |
| Δ9-THC | 9.3 mg | 0.93 mg |
| Δ8-THC | 1.8 mg | 0.18 mg |
| CBT (Cannabicitran) | 0.75 mg | 75 μg |
| CBG (cannabigerol) | 0.10 mg | 60 μg |

Volunteer participants were selected through immediate connection to the project and represent a population with complicated medical histories. The company-related subgroup of volunteers were observed separately. Neither group was blinded.

Qualitative unprompted reports of effects summarized in Table 8. Suggested dose was 1 mL of a 15 mg/mL solution.

TABLE 8

Effects of administration of MCD.

| Observed Effect | Volunteers (n = 10) | Company-related Volunteers (n = 5) |
|---|---|---|
| Sedative | 1 (10%) | 2 (40%) |
| Improved Sleep | 10 (100%) | 5 (100%) |
| Anxiolytic/Relaxation | 9 (90%) | 5 (100%) |
| Aphrodisiac | 2 (20%) | 1 (20%) |
| Reduced Pain | 1 (10%) | 4 (80%) |
| Vivid dreams | 4 (40%) | 5 (100%) |
| Grogginess | 0 (0%) | 1 (20%) |
| Little to no psychoactive effect | 1 (10%) | 1 (20%) |

The majority of volunteers experienced "deeper" sleep and woke up feeling rested. One volunteer reported 15-20% increased REM sleep through monitoring. Volunteers also reported relaxing and mild sedative effects of the medical *Cannabis* distillate.

The observed effects of MCD are supported by the following pharmacological mechanisms:

Sedative/Improved Sleep: CBN has been shown to double pentobarbital-induced sleeping time in mice. CBN and CBN derivatives (omCBN, oprCBN, opeCBN) are likely to share this effect and may act synergistically, improving efficacy.

Anxiolytic/Relaxation: Enzyme inhibition (specifically MGL) is linked to anxiolytic effects. In the molecular docking studies components of the medical *Cannabis* distillate docked with high indication of inhibition at MGL and ABHD6 (2-AG metabolic enzymes), leading to this effect.

Aphrodisiac: Chocolate is generally regarded as having aphrodisiac properties; this has been attributed to unsaturated N-acylethanolamines that are cannabinoid mimetics, comparable to AEA, and may increase endogenous AEA levels. AEA is a CB1R partial agonist; omCBN was predicted based on molecular docking studies to have partial agonist activity at CB1R.

Reduced Pain: Both endocannabinoids and their metabolites, eicosanoids, are direct signaling factors for inflammation; COX-inhibitor drugs target the arachidonic acid cascade. Additionally, cannabinoids are capable of reducing neuropathic pain by inhibiting neurons that release inflammatory neuropeptides. Enzyme inhibition would lead to larger levels of endogenous cannabinoids that may cause this effect. Synergistic effects would be seen by activating CB1R.

Example 15. Human Trial of HCD as a Mood-Stabilizer and/or Atypical Antipsychotic A 30 y.o assigned female at birth nonbinary volunteer with a history of neuroatypicality and chronic pain was previously treated with a single dose of >0.25 g smoked hemp *Cannabis* (>~20 mg/0.8 mg CBD/THC) per day. The volunteer abstained from any pharmacological agents for 48 hours before the onset of dosing aside from a single dose of caffeine (70-140 mg) each morning. The volunteer ingested 1 mL of the HCD solution (15 mg/mL) every morning and 0.5 mL of the HCD solution (15 mg/mL) at night as needed (0-2 times per week). The volunteer orally ingested HCD solubilized in coconut oil (15 mg/mL) for the first two months of administration, then HCD solubilized in olive oil (15 mg/mL). A minimum therapeutic dose was determined to be 10-30 mg of HCD per day.

The HCD does not have any acute effects nor are there any quantitative metrics to use as direct comparison. Efficacy was determined as subjective perception of baseline inflammation, anxiety, and mood-stabilization over time.

The volunteer reported the following effects:
  The orally ingested HCD was not as effective therapeutically as smoking hemp, but the pharmacokinetic profile was improved for longer duration of action.
  Efficacy was significantly improved in comparison to 50 mg CBD isolate (>98% pure CBD in crystalline form in gel capsules).
  Efficacy was significantly improved in comparison to ~50 mg/0.8 mg CBD/THC from traditionally extracted hemp concentrates taken orally.
  After a 2-week trial period, the volunteer chose to continue using HCD as their primary therapeutic agent.

The observed effects of HCD are supported by the following pharmacological mechanisms:

The serotonin system is the classical pathway of pharmacological intervention for mood stabilization—namely reuptake inhibitors (SSRIs)—that increase levels of serotonin/time of serotonin in the synapse by preventing their reuptake into neighboring neurons. The ECS has been shown to be an upstream regulator of the serotonin system that acts by controlling the polarization of serotonergic neurons. It has been demonstrated to control serotonin release and modulate depressive-like behaviors in rats. Pharmacological modulation of the ECS directly affects serotonin levels and, therefore, may act in a comparable manner to modulating the serotonin system directly. The main ECS target responsible for the psychoactive effects is the CB1R. As shown above, omCBD and CBND bind to the CB1R; this may lead to increased efficacy over traditional hemp extracts containing only CBD which acts as a neutral antagonist at the CB1R. Additionally, as demonstrated above, omCBD, CBND, omCBN, oprCBN, and opeCBN interact MGL and ABHD6, increasing endogenous levels of 2-AG and further activating the ECS. This synergistic effect is most likely the cause of the increased potency.

The benefit of increasing potency is in reduction of the recommended dosage. For mood stabilizing drugs that are taken continuously over prolonged periods of time, decreasing dosage reduces the stress on the body (mainly the liver), and reduces the likelihood of negative side effects.

Example 16. Human Trial of MCD as an Anxiolytic

A 30 y.o. assigned female at birth nonbinary volunteer with a history of neuroatypicality and chronic pain was being previously treated with a single dose of >0.25 g smoked hemp *Cannabis* (>~20 mg/0.8 mg CBD/THC) per day. The volunteer abstained from any pharmacological agents for 48 hours before the onset of dosing aside from a single dose of caffeine (70-140 mg) each morning. The volunteer orally ingested MCD solubilized in extra virgin olive oil (15 mg/mL-See Example 14). The following effect were observed at various doses:

Threshold dose (10 mg):
  Onset-Come Up: 1.75-2 hrs
  Peak-Plateau: 0.5 hr
  Come Down: Undiscernible
  After Effects: None
  Observations: Mild peripheral effects—reduced pain, no significant changes in blood pressure, or body temperature. No psychoactive effects.

Low dose (15 mg):
  Onset-Come Up: 1-2 hrs
  Peak-Plateau: 1 hr
  Come Down: 2 hrs
  After Effects: None
  Observations: Peripheral effects—reduced pain, body load (reminiscent of benzodiazepines or ethanol, but far less intense), reduced systolic blood pressure ($\Delta P=5$ mm Hg, n=3), observable vasodilation, no significant change in body temperature. Mild psychoactive effects—reduced perseverative thoughts, reduced rapid thoughts, reduced general anxiety, improved sleep quality with vivid, memorable dreams.

Moderate dose (30 mg):
  Onset-Come Up: 1-2 hrs
  Peak-Plateau: 2.5 hrs
  Come Down: 2 hrs
  After Effects: Body relaxation/heaviness
  Observations: Peripheral effects—reduced tactile hyperesthesia, reduced pain, body load (reminiscent of benzodiazepines or ethanol, but slightly less intense), reduced systolic blood pressure ($\Delta P=7$ mm Hg, n=3), observable vasodilation, reduced body temperature ($\Delta T=1.7°$ F., n=3). Psychoactive effects—reduced auditory hyperesthesia, mild sedation, reduced perseverative thoughts, reduced rapid thoughts, reduced general anxiety, improved sleep quality with vivid, memorable dreams.
  Note: This was determined to be the maximal dose for the subject as reduced body temperature is a metric of sufficient CB1 agonist activity for a 3 day period.

Multiple Doses (15 mg at 7 am, 15 mg at 12 pm):
  Onset-Come Up: 1-2 hrs
  Peak-Plateau: 7-8 hrs
  Come Down: 2 hrs
  After Effects: Body relaxation/heaviness
  Observations: Same effects profile as low dose with longer plateau. Faster onset time of second dose was observed—this phenomenon is qualitatively documented across many other psychedelic substances, but not well explained.

Example 17. Human Trial of HCD or MCD as a Treatment for Hereditary Neuropathy with Liability to Pressure Palsy (HNPP)

A 30 y.o. male volunteer has a rare genetic disorder, HNPP, resulting in neuropathic pain, muscle weakness, numbness, and loss of fine motor skills. The volunteer previously needed high doses (more than 5 g/day) of medical *Cannabis* to receive beneficial effects, but reduced overall intake when he began taking HCD and MCD. His current dose schedule is 15-30 mg of HCD per day (~7 mg-15 mg CBD) and MCD as needed. He is not taking any other medication. HCD and MCD perform better than the opioids, benzodiazepines, and sedatives that used to be his standard treatment.

HCD

1. Topical administration (~50 mg HCD, ~25 mg CBD): the extract has a slight numbing effect at the application site that is immediately noticeable and fast-acting. In comparison to hexane-extracted distillate prepared from the same starting material as described in Example 10, HCD was faster and more efficacious in reducing local pain.

2. Oral administration (15-30 mg HCD, ~7-15 mg CBD): HICD has a subtle effect that lasts for 2-3 hours and reduces anxiety, pain, and discomfort. In comparison, oral ingestion of the same dose of commercially available CBD isolate (BlueBird Botanicals (CO, USA) and EcoGen Laboratories (CO, USA)) provides no noticeable effect, and is more similar to taking a vitamin or supplement.

3. Smoking/Inhalation at 575-600° F.:
- 25 mg CBD isolate (>98% pure by NMR): pain relief began at 10 minutes, slight decrease in stress and anxiety at 15 minutes, and noticeable body feeling at 30 minutes. The effects began to wear off at 45 minutes, with pain returning at 50 minutes and no noticeable effects at 60 minutes.
- 50 mg HCD (55% CBD): pain relief, mental clarity, and uplifted mood at 10 minutes, increased energy and complete reduction of pain at 20 minutes, absence of anxiety at 45 minutes, effects persisted at 60 minutes and began to wear off at 75 minutes. At 90 minutes there were no mental effects remaining, but the volunteer reported zero anxiety and zero body pain.

MCD

1. At a dose of 15-30 mg MCD (~4.5-9 mg CBN, —1-2 mg THC)
- Relieves pain;
- Reduces stress and anxiety;
- Reduces irritability.

2. At a dose of 70 mg MCD (~20 mg CBN, 5 mg THC)
- Sedative and improves sleep quality;
- Noticeable psychoactive effects.

Example 18. Human Trial of HCD or MCD as a Treatment for Crohn's Disease

A 26 y.o. female volunteer with severe Crohn's disease and who has had over 50 hospital emergency visits since diagnosis in 2015. Treatment with multiple pharmaceutical agents were unsuccessful. She stopped using all pharmaceutical agents in 2018. In August 2020, she began using HCD and MCD. She was able to completely stop a Crohn's disease flare in November 2020 using two consecutive doses of MCD. The HCD and MCD perform better than the biologics, steroids, and antibiotics used to be her standard treatment options.

HCD

1. Oral administration (15 mg HCD, ~7 mg CBD): The effects of HCD administration were felt the day-of and lasted for 2-3 hours. HICD relieved all of the volunteer's common symptoms (joint pain, anxiety, brain fog, irritability, abdominal pain, and nausea). By comparison, the volunteer needs over 50 mg of commercially available CBD isolate on two or more consecutive days to achieve similar results by oral administration.

2. Smoking/Inhalation at 575-600° F.:
- 7 mg CBD Isolate (>98% pure CBD): decreased pain, stress, and anxiety at 15 minutes, noticeable body effects at 30 minutes, effects began to wear off at 45 minutes. No noticeable effects at 60 minutes and return of abdominal pain.
- 15 mg HCD (55% CBD): pain relief and increased energy began at 10 minutes, stomach pain and anxiety eliminated at 20 minutes, effects persisted for 75 minutes. At 90 minutes the effects had worn off, but the volunteer reports residual positive effects.

MCD

At a dose of 15 mg MCD (~4.5 mg CBN, 1 mg THC-See Example 14)
- Reduces gastrointestinal distress;
- Reduces abdominal pain;
- Reduces nausea;
- Reduces anxiety;
- Reduces depression;
- After two consecutive doses the volunteer was able to completely abort the onset of a Crohn's flare and cease taking budesonide, a steroid medication with side effects such as fatigue, vomiting, and joint pains.

Example 19. Human Trial of HCD or MCD as a Treatment for Chronic Migraine

A 30 y.o. assigned female at birth nonbinary volunteer with a history of severe, chronic migraines (over 15 disabling headache days per month). She has had no success with over 40 prescribed medications, and two failed brain surgeries. The volunteer stopped taking all psychopharmaceutical agents in 2015 due to lack of efficacy and negative side effects. Her migraine disability assessment test (MIDAS) score was 21+(Severe Disability) for over 15 years. In October 2019 she began using commercial CBD isolate (BlueBird Botanicals (CO USA), >98% CBD; started at 50 mg/day; titrated up to 250 mg/day), and after two months reported a marked decrease in the number and severity of migraines. In August 2020, the volunteer began taking MCD and HCD. Her current MIDAS score is 9 (Mild Disability) with no other pharmacological intervention. HCD and MCD perform better than the triptans, opioids, anticonvulsants, beta-blockers, calcium-channel blockers, and miscellaneous other agents used to be the volunteer's standard treatments.

HCD

Oral administration (15 mg HCD, —7 mg CBD)
- Reduces anxiety. By comparison, the volunteer needs over 200 mg of commercially available CBD isolate to achieve similar results by oral administration.
- Reduces migraine potential threshold after two consecutive days (fewer migraines). By comparison, the volunteer needs over 200 mg of commercially available CBD isolate to achieve similar results by oral administration.
- Reduces migraine severity after two consecutive days (less migraines). By comparison, the volunteer needs over 200 mg of commercially available CBD isolate to achieve similar results by oral administration.

MCD

At a dose of 15 mg MCD (~4.5 mg CBN, 1 mg THC-See Example 14)
- Improves sleep;
- Reduces migraine potential;
- Therapeutic profile is different (less intense/obvious of an experience), but overall anxiolytic properties similar to 2.5 mg of benzodiazepines Reduces nausea;
- Reduces pain during migraine recovery/progression.

Example 20. Human Trial of HCD or MCD as a Treatment for Autism Spectrum/Schizophrenia Spectrum Disorder A 30 y.o. assigned female at birth nonbinary volunteer with a history of a developmental disorder whose symptoms span both Autism Spectrum Disorder and Schizophrenia Spectrum Disorder. They stopped taking all psychopharmaceutical agents in 2010 after beginning to use medical *Cannabis* daily. Outside of 3 relapses due to over 14+ days without *Cannabis*, they have had no issues managing their symptoms since. Due to decreased symptoms, they are highly functional, fully independent, and no longer meet criteria for their previous diagnoses. In August 2020, they began using the HCD and MCD. They have not missed a single dose of HCD in 5 months; it is their longest span of completely continuous compliance. HCD and MCD perform better than the antipsychotic, antidepressants, benzodiazepines, and sedatives used to be their standard treatment.

HCD

1. Oral administration (15 mg HCD, ~7 mg CBD) for 7 consecutive days:
    Reduces repetitive behaviors;
    Reduces auditory hyperesthesia;
    Reduces tactile hyperesthesia;
    Prevents auditory hallucinations;
    Prevents visual hallucinations;
    Reduces basal anxiety/depression;
    Reduces basal inflammation;

Efficacy for all of the observed effects is higher than what the volunteer experienced upon administration of over 50 mg CBD isolate or over 50 mg CBD from traditional orally administered extracts (CBD isolate containing >98% CBD, sources: Bluebird Botanicals (CO, USA; CBD from traditional orally administered extracts sources: Bluebird Botanicals (CO, USA), high CBD full spectrum from hemp; Howl's Tincture (MA, USA), 20:1 CBD:THC full spectrum from medical *Cannabis*) (for at least 14 consecutive days, which is the period needed to reach the desired therapeutic effects. Doses of 50 mg/day of CBD result in negative side effects, such as forgetfulness/brain fog, apathy, decreased endurance, decreased strength, interrupted sleep routine. Furthermore, the volunteer used high doses of commercially available CBD isolate (400-600 mg) to abort panic attacks and/or break perseverative loops. The volunteer reported a "hangover" observed the next day. By contrast, the volunteer reports only needing 45 mg of HCD (~22.5 mg CBD) to reach the same efficacy. The volunteer estimates that HCD is about 10-fold higher in potency compared to the commercially available CBD isolate.

MCD

At a dose of 15 mg MCD (~4.5 mg CBN, 1 mg THC-See Example 14)
    Improves sleep;
    Reduces perseverative thoughts (which are antecedents of obsessive compulsive behaviors);
    Therapeutic profile is different (less intense/obvious of an experience), but overall anxiolytic properties similar to 2.5 mg of benzodiazepines; reduces nausea.

REFERENCES

1. Bucar F, Wube A, Schmid M. (2013) Natural product isolation—how to get from biological material to pure compounds. Nat Prod Rep. 30(4), 525-545. doi:10.1039/c3np20106f
2. Hanson, J. R. (2003). Natural products: the secondary metabolites. Cambridge: Royal Society of Chemistry.
3. Pennacchio, M., Jefferson, L. V., & Havens-Young, K. (2010). Uses and abuses of plant-derived smoke: its ethnobotany as hallucinogen, perfume, incense, and medicine. New York, N.Y.: Oxford University Press.
4. Vita, Daniela De, et al. (2019). Comparison of Different Methods for the Extraction of Cannabinoids from *Cannabis*. Natural Product Research, (1-7). doi:10.1080/14786419.2019.1601194.

The teachings of all patents, published applications and references cited herein are incorporated by reference in their entirety.

While this invention has been particularly shown and described with references to example embodiments thereof, it will be understood by those skilled in the art that various changes in form and details may be made therein without departing from the scope of the invention encompassed by the appended claims.

What is claimed is:

1. A method for obtaining a mixture of compounds from a plant material, comprising:
    (a) thermally treating the plant material comprising at least one of cannabidiol (CBD) and tetrahydrocannabinol (THC), by heating the plant material to a temperature from about 90° C. to about 700° C., thereby forming a gaseous composition comprising the mixture of compounds;
    (b) contacting the gaseous composition with a lipophilic affinity medium, thereby separating the mixture of compounds from the gaseous composition;
    (c) eluting the mixture of compounds from the lipophilic affinity medium by contacting the lipophilic affinity medium with an elution solution, thereby obtaining an elution mixture comprising the mixture of compounds and the elution solution; and
    (d) removing the elution solution from the elution mixture,
wherein the plant material is selected from raw *Cannabis* biomass, dried *Cannabis* biomass, raw *Cannabis* flower, dried *Cannabis* flower, and *Cannabis* trichomes and further wherein the lipophilic affinity medium comprises pores.

2. The method of claim 1, wherein the plant material is raw *Cannabis sativa* biomass, dried *Cannabis sativa* biomass, raw *Cannabis sativa* flower, dried *Cannabis sativa* flower, or *Cannabis sativa* trichomes.

3. The method of claim 1, wherein the temperature is above about 150° C.

4. The method of claim 1, wherein forming the gaseous composition comprises heating the plant material in a sealed vessel.

5. The method of claim 1, comprising applying reduced pressure from about 250 Torr to about 0.1 Torr to a vessel in which the plant material is being thermally treated.

6. The method of claim 1, wherein
    the lipophilic affinity medium comprises particles;
    the particles comprise a core and a plurality of lipophilic groups; and
    each lipophilic group of the plurality of lipophilic groups is attached to the core.

7. The method of claim 6, wherein each lipophilic group of the plurality of lipophilic groups independently comprises $C_{2-24}$ alkyl, $C_{6-12}$ aryl, $C_{2-24}$ alkyl($C_{6-12}$ aryl), tri($C_{1-12}$ alkyl) silyl, or di($C_{1-12}$ alkyl)silyl($C_{2-24}$ alkyl).

8. The method of claim 1, wherein the gaseous composition contacts at least one porous membrane prior to contacting the lipophilic affinity medium.

9. The method of claim 8, wherein each porous membrane comprises pores, wherein the size of the pores of each porous membrane is independently from about 5 μm to about 50 μm.

10. The method of claim 6, wherein the core comprises silica, a polymer, or a combination thereof.

11. The method of claim 1, wherein the elution solution comprises a solvent, wherein the solvent is methanol, ethanol, a methanol/water mixture, an ethanol/water mixture, pentane, hexane, heptane, cyclohexane, acetone, tetrahydrofuran, ethyl acetate, diethyl ether, or mixtures thereof.

12. The method of claim 1, wherein the elution solution solvent is removed by evaporation or lyophilization.

13. The method of claim 1, further comprising separating the elution mixture by chromatography or fractionation by solubility.

14. A method for obtaining a mixture of compounds from a plant material, comprising:
 (a) thermally treating the plant material comprising at least one of cannabidiol (CBD) and tetrahydrocannabinol (THC), by heating the plant material to a temperature from about 90° C. to about 700° C., thereby forming a gaseous composition comprising the mixture of compounds;
 (b) adiabatically expanding the gaseous composition, thereby producing a first fraction of the compounds and creating a remainder of the gaseous composition;
 (c) contacting the remainder of the gaseous composition with a lipophilic affinity medium, thereby separating the mixture of compounds from the remainder of the gaseous composition;
 (d) eluting the mixture of compounds from the lipophilic affinity medium, by contacting the lipophilic affinity medium with an elution solution, thereby obtaining an elution mixture comprising the mixture of compounds and the elution solution; and
 (e) removing the elution solution from the elution mixture,
 wherein the plant material is selected from raw *Cannabis* biomass, dried *Cannabis* biomass, raw *Cannabis* flower, dried *Cannabis* flower, and *Cannabis* trichomes.

15. The method of claim 14, wherein the volume of the gaseous composition is increased by about 100 fold to about 1000 fold as compared to the volume prior to adiabatically expanding.

16. The method of claim 14, wherein the lipophilic affinity medium comprises pores.

17. The method of claim 14, wherein the gaseous composition contacts at least one porous membrane prior to contacting the lipophilic affinity medium.

18. A method for obtaining a mixture of compounds from a plant material, comprising:
 (a) thermally treating the plant material comprising at least one of cannabidiol (CBD) and tetrahydrocannabinol (THC), by heating the plant material to a temperature from about 90° C. to about 700° C., thereby forming a gaseous composition comprising the mixture of compounds;
 (b) contacting the gaseous composition with a lipophilic affinity medium, thereby separating the mixture of compounds from the gaseous composition;
 (c) eluting the mixture of compounds from the lipophilic affinity medium by contacting the lipophilic affinity medium with an elution solution, thereby obtaining an elution mixture comprising the mixture of compounds and the elution solution; and
 (d) removing the elution solution from the elution mixture,
 wherein the plant material is selected from raw *Cannabis* biomass, dried *Cannabis* biomass, raw *Cannabis* flower, dried *Cannabis* flower, and *Cannabis* trichomes and
 further wherein
  the lipophilic affinity medium comprises particles;
  the particles comprise a core and a plurality of lipophilic groups; and
  each lipophilic group of the plurality of lipophilic groups is attached to the core.

19. The method of claim 18, wherein forming the gaseous composition comprises heating the plant material in a sealed vessel.

20. The method of claim 18, comprising applying reduced pressure from about 250 Torr to about 0.1 Torr to a vessel in which the plant material is being thermally treated.

21. The method of claim 18, wherein the lipophilic affinity medium comprises pores.

22. The method of claim 18, wherein the gaseous composition contacts at least one porous membrane prior to contacting the lipophilic affinity medium.

23. The method of claim 18, wherein the core comprises silica, a polymer, or a combination thereof.

24. The method of claim 18, wherein the elution solution comprises a solvent, wherein the solvent is methanol, ethanol, a methanol/water mixture, an ethanol/water mixture, pentane, hexane, heptane, cyclohexane, acetone, tetrahydrofuran, ethyl acetate, diethyl ether, or mixtures thereof.

25. A method for obtaining a mixture of compounds from a plant material, comprising:
 (a) thermally treating the plant material comprising at least one of cannabidiol (CBD) and tetrahydrocannabinol (THC), by heating the plant material to a temperature from about 90° C. to about 700° C., thereby forming a gaseous composition comprising the mixture of compounds;
 (b) contacting the gaseous composition with a lipophilic affinity medium, thereby separating the mixture of compounds from the gaseous composition;
 (c) eluting the mixture of compounds from the lipophilic affinity medium by contacting the lipophilic affinity medium with an elution solution, thereby obtaining an elution mixture comprising the mixture of compounds and the elution solution; and
 (d) removing the elution solution from the elution mixture,
 wherein the plant material is selected from raw *Cannabis* biomass, dried *Cannabis* biomass, raw *Cannabis* flower, dried *Cannabis* flower, and *Cannabis* trichomes and
 further wherein the gaseous composition contacts at least one porous membrane prior to contacting the lipophilic affinity medium.

26. The method of 25, wherein forming the gaseous composition comprises heating the plant material in a sealed vessel.

27. The method of 25, comprising applying reduced pressure from about 250 Torr to about 0.1 Torr to a vessel in which the plant material is being thermally treated.

28. The method of 25, wherein:
 the lipophilic affinity medium comprises particles;
 the particles comprise a core and a plurality of lipophilic groups; and
 each lipophilic group of the plurality of lipophilic groups is attached to the core.

29. The method of 25, wherein the lipophilic affinity medium comprises pores.

30. The method of 25, wherein the elution solution comprises a solvent, wherein the solvent is methanol, ethanol, a methanol/water mixture, an ethanol/water mixture, pentane, hexane, heptane, cyclohexane, acetone, tetrahydrofuran, ethyl acetate, diethyl ether, or mixtures thereof.

* * * * *